(12) United States Patent
Segev et al.

(10) Patent No.: US 12,322,164 B2
(45) Date of Patent: Jun. 3, 2025

(54) UI FOR HEAD MOUNTED DISPLAY SYSTEM

(71) Applicant: BEYEONICS SURGICAL LTD., Haifa (IL)

(72) Inventors: Eran Segev, Haifa (IL); Shahaf Zommer, Haifa (IL); Yaara Solomon, Haifa (IL); Ron Schneider, Haifa (IL); Rani Ben-Yishai, Haifa (IL)

(73) Assignee: BEYEONICS SURGICAL LTD., Haifa (IL)

( * ) Notice: Subject to any disclaimer, the term of this patent is extended or adjusted under 35 U.S.C. 154(b) by 0 days.

(21) Appl. No.: 18/637,356

(22) Filed: Apr. 16, 2024

(65) Prior Publication Data
US 2024/0265688 A1    Aug. 8, 2024

Related U.S. Application Data

(63) Continuation of application No. 17/288,455, filed as application No. PCT/IL2019/051155 on Oct. 27, 2019, now Pat. No. 11,989,930.
(Continued)

(51) Int. Cl.
*G06V 10/80* (2022.01)
*A61B 34/00* (2016.01)
(Continued)

(52) U.S. Cl.
CPC ............ *G06V 10/806* (2022.01); *A61B 34/25* (2016.02); *A61B 90/37* (2016.02);
(Continued)

(58) Field of Classification Search
CPC ....... A61B 34/25; A61B 34/30; A61B 90/361; A61B 90/37; A61B 2017/00203;
(Continued)

(56) References Cited

U.S. PATENT DOCUMENTS

| 5,781,165 A | 7/1998 | Tabata |
| 5,977,935 A | 11/1999 | Yasukawa et al. |

(Continued)

FOREIGN PATENT DOCUMENTS

| JP | H095666 A | 1/1997 |
| JP | 2015192697 A | 11/2015 |

(Continued)

*Primary Examiner* — Mihir K Rayan
(74) *Attorney, Agent, or Firm* — Merchant & Gould P.C.

(57) ABSTRACT

A UI for a HMD system includes a HMD configured to be worn by a surgeon. A tracker is configured to track head gestures by the surgeon. A footswitch is configured to detect foot motion inputs by the surgeon. A computer couples to the HMD, the tracker, and the footswitch. A user interface includes the HMD, tracker, and footswitch. The use interface is configured to: provide to the computer the head gesture in association with the foot motion input, and display an image relating to a surgical procedure on the HMD. The computer is configured to: apply the head gesture received in association with the foot motion input to perform a first action on the HMD system when the HMD system is in a first system mode, and perform a second action on the HMD system when the HMD system is in a second system mode.

20 Claims, 58 Drawing Sheets

Related U.S. Application Data

(60) Provisional application No. 62/925,269, filed on Oct. 24, 2019, provisional application No. 62/857,834, filed on Jun. 6, 2019, provisional application No. 62/750,276, filed on Oct. 25, 2018.

(51) Int. Cl.

| | |
|---|---|
| *A61B 90/00* | (2016.01) |
| *G02B 27/01* | (2006.01) |
| *G06F 3/01* | (2006.01) |
| *G06F 3/033* | (2013.01) |
| *G06F 3/0485* | (2022.01) |
| *G06V 10/94* | (2022.01) |
| *G06V 20/20* | (2022.01) |
| *G06V 40/18* | (2022.01) |
| *H04N 23/62* | (2023.01) |
| *A61B 17/00* | (2006.01) |
| *A61B 90/50* | (2016.01) |
| *G06F 3/0482* | (2013.01) |
| *H04N 5/45* | (2011.01) |
| *H04N 23/56* | (2023.01) |
| *H04N 23/695* | (2023.01) |

(52) U.S. Cl.
CPC .......... *G02B 27/0172* (2013.01); *G06F 3/011* (2013.01); *G06F 3/012* (2013.01); *G06F 3/017* (2013.01); *G06F 3/0334* (2013.01); *G06V 10/94* (2022.01); *G06V 20/20* (2022.01); *G06V 40/193* (2022.01); *H04N 23/62* (2023.01); *A61B 2017/00216* (2013.01); *A61B 2017/00973* (2013.01); *A61B 90/361* (2016.02); *A61B 2090/373* (2016.02); *A61B 2090/502* (2016.02); *G02B 2027/0138* (2013.01); *G06F 3/0482* (2013.01); *G06F 3/0485* (2013.01); *G06F 2203/04806* (2013.01); *H04N 5/45* (2013.01); *H04N 23/56* (2023.01); *H04N 23/695* (2023.01)

(58) Field of Classification Search
CPC .......... A61B 2017/00216; A61B 2017/00973; A61B 2034/2048; A61B 2034/2051; A61B 2034/2055; A61B 2034/258; A61B 2034/742; A61B 2090/306; A61B 2090/309; A61B 2090/365; A61B 2090/371; A61B 2090/372; A61B 2090/373; A61B 2090/3735; A61B 2090/502; G02B 27/0172; G02B 2027/138; G06F 3/011; G06F 3/012; G06F 3/013; G06F 3/017; G06F 3/0334; G06F 3/0482; G06F 3/0485; G06F 2203/04806; G06F 2218/12; G06V 10/94; G06V 40/193; H04N 5/45; H04N 23/56; H04N 23/62; H04N 23/675; H04N 23/69; H04N 23/695

See application file for complete search history.

(56) References Cited

U.S. PATENT DOCUMENTS

| | | | |
|---|---|---|---|
| 6,320,559 B1 | 11/2001 | Yasukawa et al. | |
| 6,396,497 B1 | 5/2002 | Reichlen | |
| 6,591,239 B1 | 7/2003 | McCall | |
| 6,847,336 B1 | 1/2005 | Lemelson et al. | |
| 7,127,401 B2 | 10/2006 | Miller | |
| 8,941,559 B2 | 1/2015 | Bar-Zeev et al. | |
| 9,285,872 B1 | 3/2016 | Raffle et al. | |
| 9,286,730 B2 | 3/2016 | Bar-Zeev et al. | |
| 9,292,084 B2 | 3/2016 | Abdollahi et al. | |
| 9,383,816 B2 | 7/2016 | Hennelly | |
| 9,454,008 B2 * | 9/2016 | Ziarati | G02B 3/0056 |
| 9,523,854 B2 | 12/2016 | Kuriya et al. | |
| 9,588,343 B2 | 3/2017 | Moravetz | |
| 9,696,797 B2 | 7/2017 | Abdollahi et al. | |
| 9,804,669 B2 | 10/2017 | Fateh | |
| 9,897,805 B2 | 2/2018 | Stafford et al. | |
| 9,911,236 B2 | 3/2018 | Bar-Zeev et al. | |
| 10,786,327 B2 * | 9/2020 | Anderson | A61B 90/50 |
| 11,006,093 B1 * | 5/2021 | Hegyi | H04N 23/54 |
| 2004/0254454 A1 | 12/2004 | Kockro | |
| 2005/0206583 A1 | 9/2005 | Lemelson | |
| 2006/0082542 A1 * | 4/2006 | Morita | A61B 5/7475 |
| | | | 345/156 |
| 2006/0284792 A1 | 12/2006 | Foxlin | |
| 2012/0027373 A1 * | 2/2012 | Chuang | G02B 27/017 |
| | | | 386/230 |
| 2013/0147686 A1 * | 6/2013 | Clavin | G02B 27/017 |
| | | | 345/8 |
| 2014/0002375 A1 | 1/2014 | Rydenhag | |
| 2014/0018960 A1 | 1/2014 | Itkowitz | |
| 2015/0070742 A1 | 3/2015 | Sorek | |
| 2015/0220142 A1 | 8/2015 | Parkinson | |
| 2015/0346813 A1 | 12/2015 | Vargas | |
| 2016/0225192 A1 * | 8/2016 | Jones | G06T 19/20 |
| 2016/0314716 A1 | 10/2016 | Grubbs | |
| 2017/0031538 A1 | 2/2017 | Andersson | |
| 2017/0242495 A1 | 8/2017 | Zhang | |
| 2017/0273549 A1 | 9/2017 | Nazareth | |
| 2018/0012413 A1 | 1/2018 | Jones | |
| 2018/0092706 A1 | 4/2018 | Anderson | |
| 2018/0113507 A1 | 4/2018 | Abdollahi | |
| 2019/0099226 A1 | 4/2019 | Hallen | |
| 2020/0038120 A1 | 2/2020 | Ziraknejad | |
| 2020/0360096 A1 | 11/2020 | Savall | |
| 2023/0027801 A1 * | 1/2023 | Qian | G06T 19/006 |

FOREIGN PATENT DOCUMENTS

| | | |
|---|---|---|
| WO | 2017114834 A1 | 7/2017 |
| WO | 2018067611 A1 | 4/2018 |

\* cited by examiner

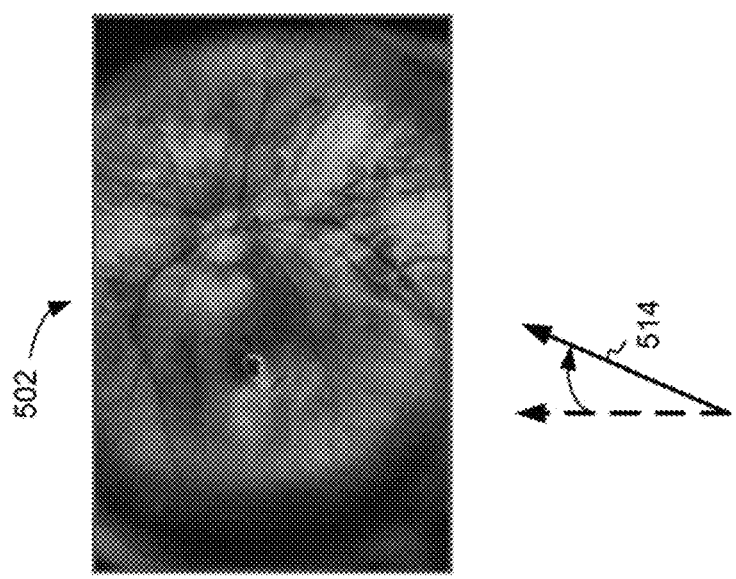
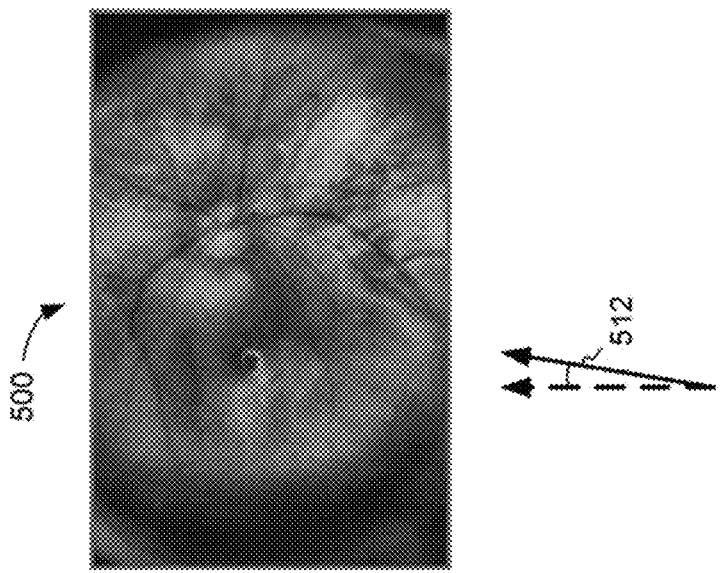
FIG. 5A

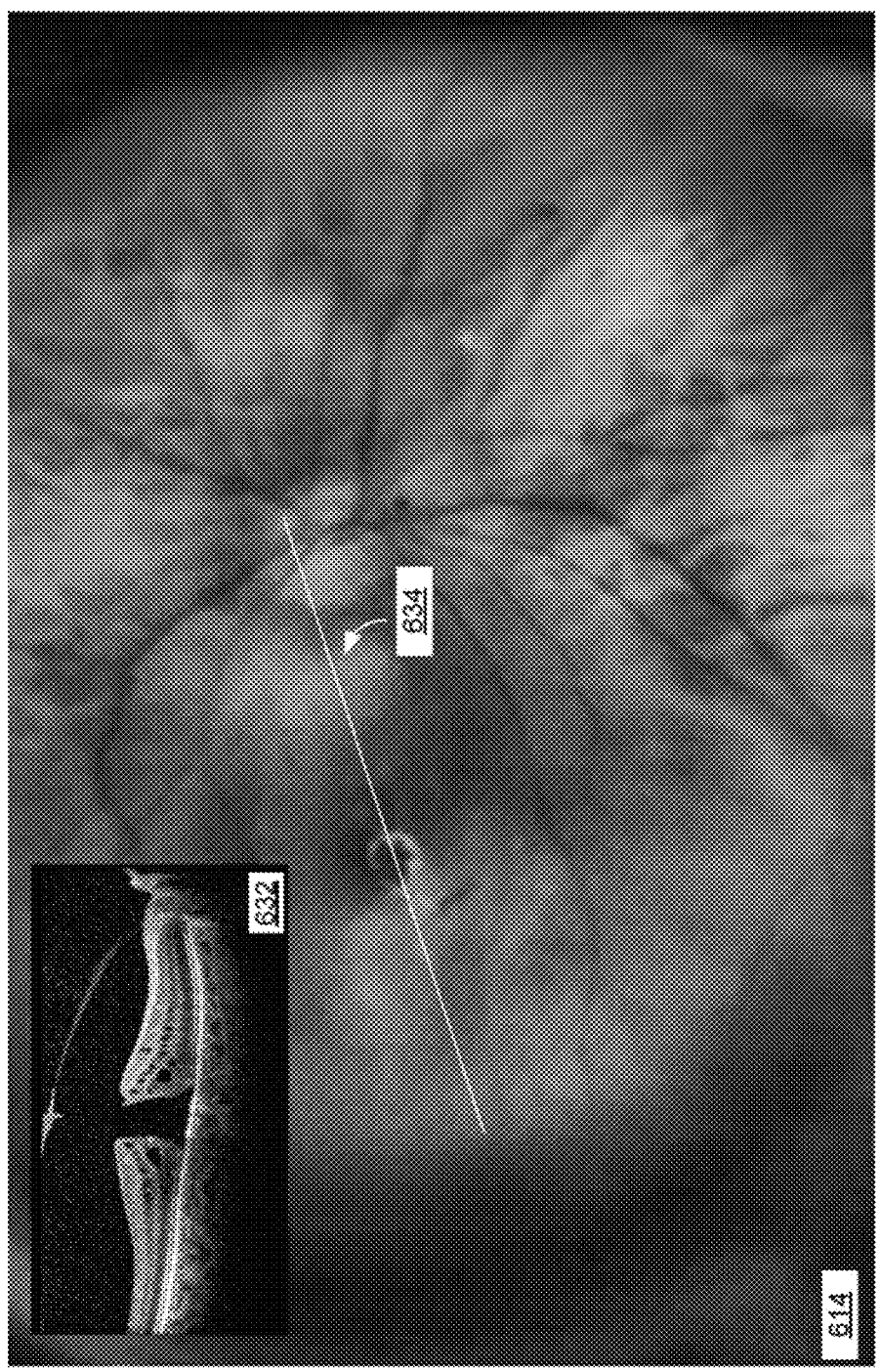

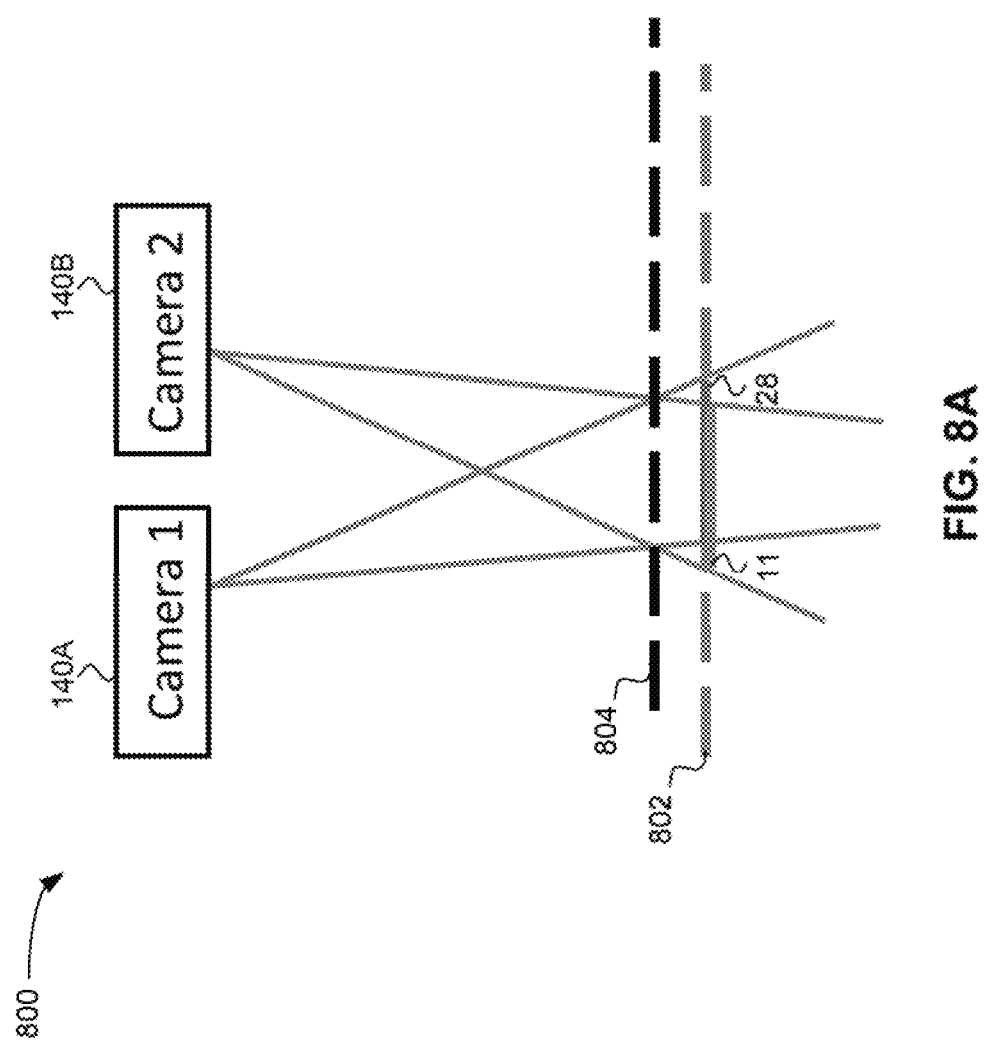

FIG. 8B

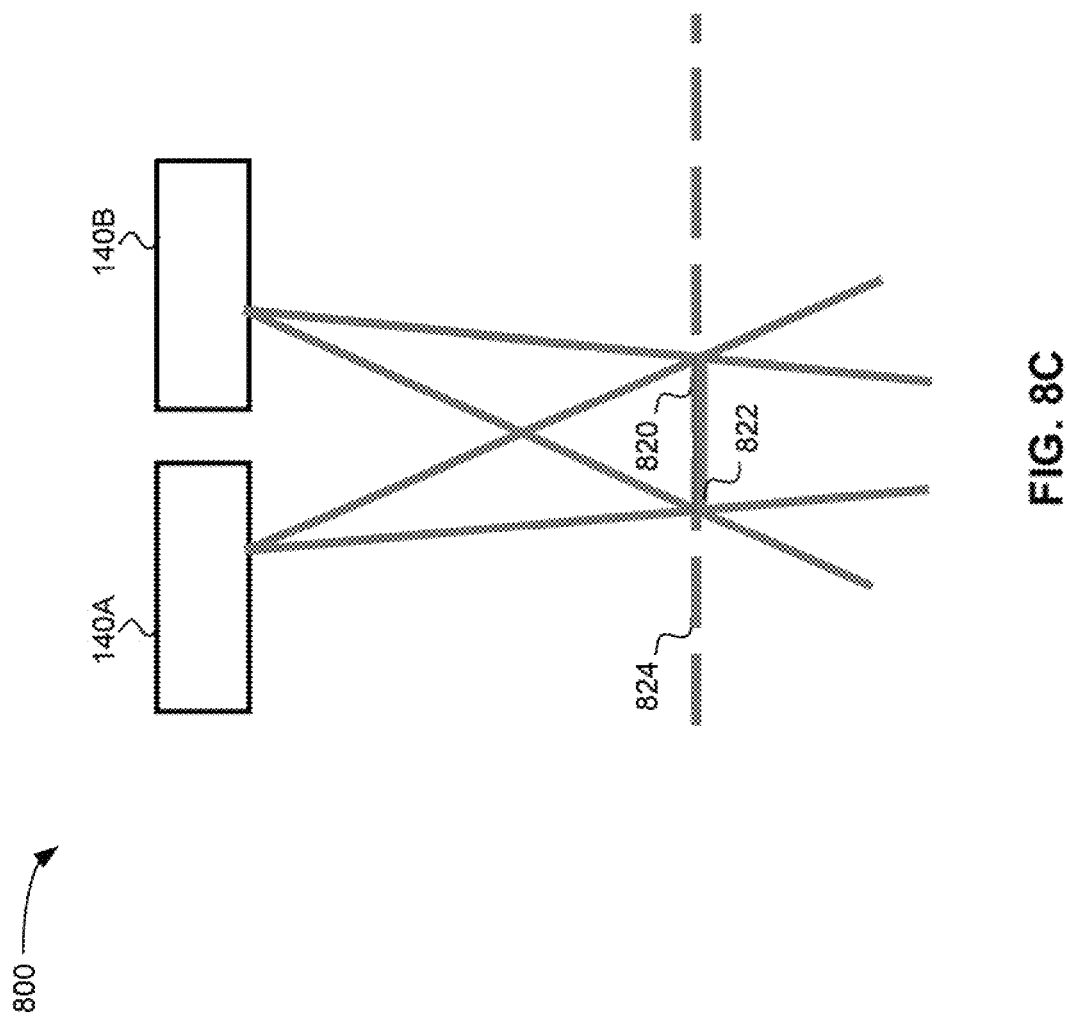

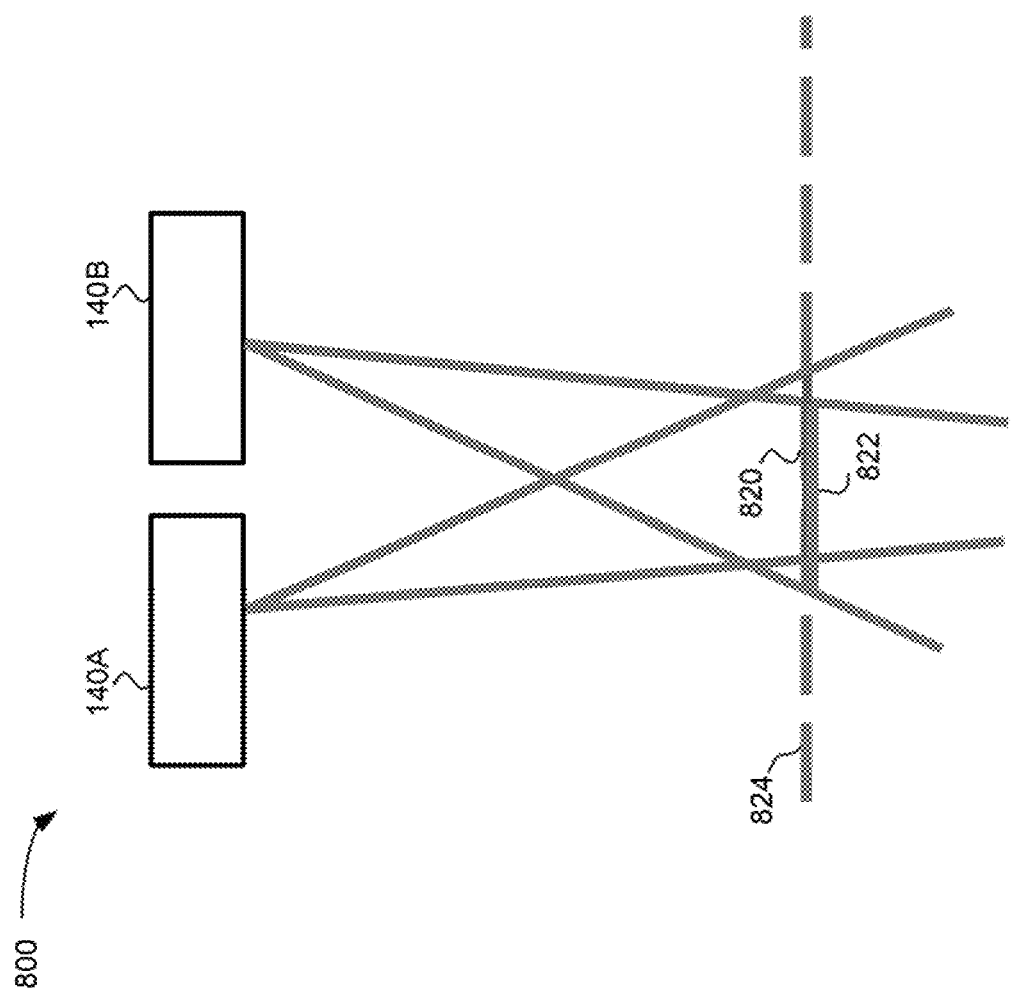

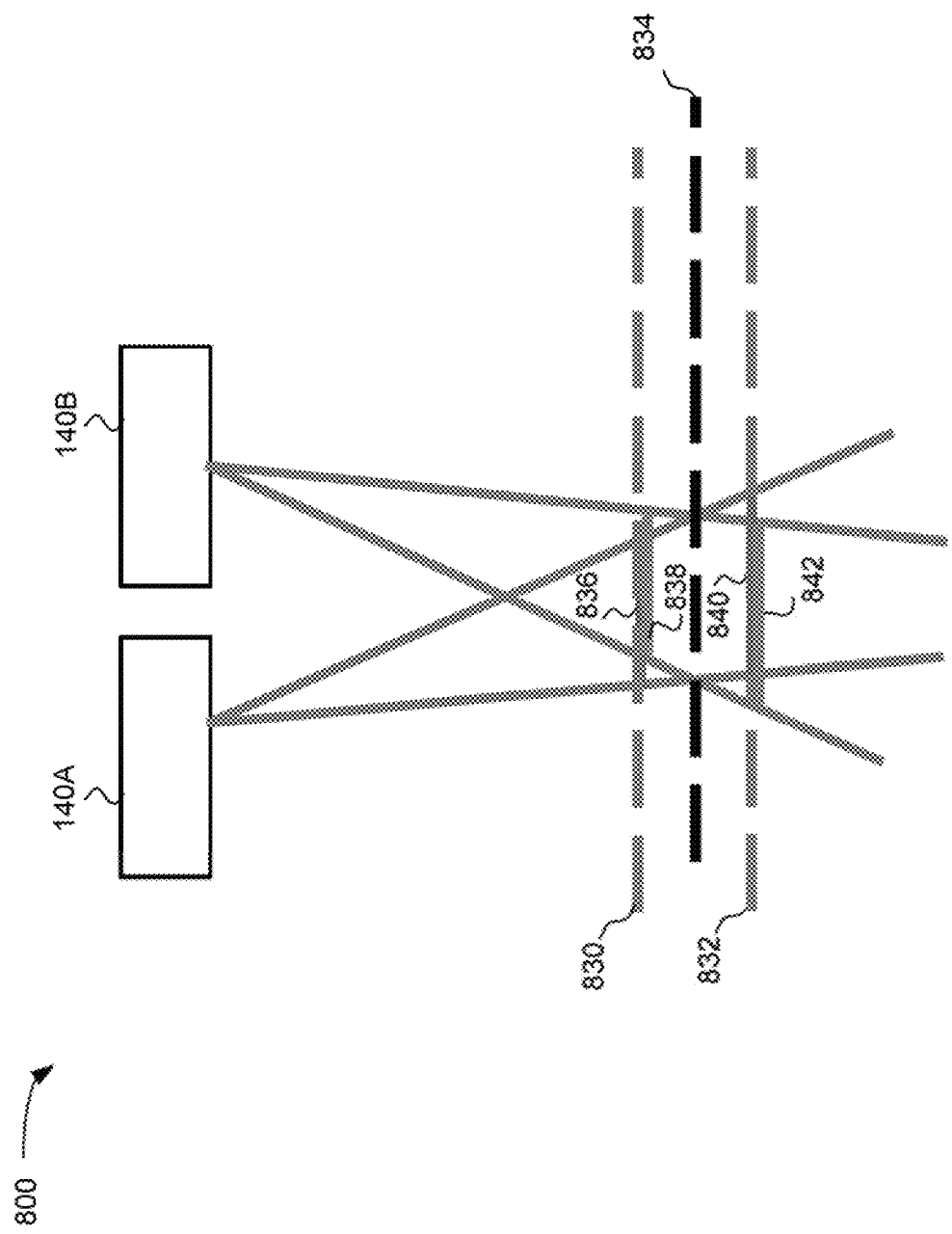

UI FOR HEAD MOUNTED DISPLAY SYSTEM

CROSS-REFERENCE TO RELATED APPLICATIONS

This application is a Continuation of U.S. Non-Provisional application Ser. No. 17/288,455, filed Apr. 23, 2021, which is a National Stage application of PCT/IL2019/051155, filed Oct. 27, 2019, which claims priority to U.S. Provisional Patent Application Nos. 62/750,276, filed Oct. 25, 2018, 62/857,834, filed Jun. 6, 2019, and 62/925,269, filed Oct. 24, 2019, and which applications are incorporated herein by reference. To the extent appropriate, a claim of priority is made to each of the above-disclosed applications.

FIELD OF THE INVENTION

The disclosed technique relates to a head mounted display, in general, and to methods and systems for controlling multiple system modes for the head mounted display, in particular.

PRIOR ART

Head mounted displays are wearable electronic displays that project an image on the wearer's field of view. In virtual reality applications, the projected image typically blocks the field of view of the wearer. In augmented reality applications, a projected image is typically superimposed on a portion of the wearer's field of view, allowing the wearer to simultaneously view real and virtual features.

U.S. Pat. No. 5,781,165 to Tabata, entitled "Image Display Apparatus of Head Mounted Type" discloses a user controlled head mounted display. While wearing the head mounted display, virtual images are projected onto an LCD screen in stereo allowing the wearer to view a three dimensional virtual image. The wearer controls the display of the virtual image by pushing a button of an electronic controller. When the head mounted display detects rotational and positional motion, such as when the wearer moves his head, the display of the virtual image is adjusted to appear stationary on a virtual image plane.

U.S. Pat. No. 5,977,935 to Yasukawa, entitled "Head-Mounted Image Display Device and Data Processing Apparatus Including the same", discloses a head mounted device for displaying augmented reality. The wearer's field of view is divided into sections. In one section of her field of view, the wearer views the real world. In another section of her field of view, one or more virtual screens are projected. By moving her line of sight by moving her head, the wearer controls which virtual screens are displayed, similar to moving a mouse to control display. A foot pedal functions as an input device, similar to a mouse click.

U.S. Pat. No. 6,320,559 to Yasukawa, entitled "Head-Mounted Image Display Device and Data Processing Apparatus Including the same" discloses a head mounted device for displaying virtual content. The wearer switches the content of the display by moving her line of sight. The wearer additionally controls attributes of the display though voice input. The wearer can scroll through the displayed images by moving her line of sight.

U.S. Pat. No. 6,396,497 to Reicheln, entitled 'Computer User Interface with Head Motion Input" discloses a wearable display system with a 360° view space. Each point in the view space is identified by a particular yaw and pitch location. By moving her head, the wearer changes the display in the view window, which occupying only a (25°× 20°) wedge within the 360° view space. Scroll bars displayed in the view window help the wearer keep track of the current location within the view space.

U.S. Pat. No. 6,847,336 to Lemelson, entitled "Selectively Controllable Heads-Up Display System, discloses a wearable display for surgeons with multiple user interfaces allowing the wearer to control the display. The system incorporates eye-tracking to move a cursor on the display screen, and any of a foot pedal or voice command to implement a "mouse click" selection.

U.S. Pat. No. 7,127,401 to Miller, entitled "Remote Control of a Medical Device Using Speech Recognition and Foot Controls" discloses a voice controlled medical imaging device for use by a surgeon. By controlling the medical imaging device through voice, the hands of the surgeon are free to perform a medical procedure.

U.S. Pat. No. 8,941,559 to Bar-Zeev, entitled "Opacity Filter for Display Device" discloses a wearable augmented reality display. Each pixel of the display is individually adjustable between maximum opacity to transparency levels, allowing light from the real world scene to be blocked or passed, accordingly. A controller controls the opacity of pixels designated for displaying virtual images superimposed on the real world scene.

U.S. Pat. No. 9,285,872 to Raffle, entitled "Using Head Gesture and Eye Position to Wake a Head Mounted Device" discloses incorporating gesture recognitions and eye tracking to switch between operating modes for a wearable display unit.

U.S. Pat. No. 9,286,730 to Bar-Zeev, entitled "Opacity Filter for Display Device" discloses a wearable augmented reality display. Each pixel of the display is individually adjustable between maximum opacity to transparency levels, allowing light from the real world scene to be blocked or passed, accordingly. The position of a virtual image superimposed on the real world scene is controlled through eye tracking.

U.S. Pat. No. 9,292,084 to Abdollahi, entitled "Control Systems and Methods for Head-Mounted Information System" discloses controlling the display for a wearable device using gesture control and a preconfigured gesture profile. The gestures may be hand or head gestures. A button is provided to toggle the gesture control feature on and off.

U.S. Pat. No. 9,383,816 to Henelly, entitled "Text Selection Using HMD Head-Tracker and Voice-Command" discloses hands-free text selection for a head mounted display. The wearer of the head mounted display selects displayed text through a combination of head and hand gestures.

U.S. Pat. No. 9,523,854 to Kuriya, entitled "Head-Mounted Display, Program for Controlling Head-Mounted Display, and Method of Controlling Head-Mounted Display", discloses a technique to improve the usability of head mounted display (HMD). An image for displaying on the HMD is selected based on detecting that the direction of HMD is outside the line of vision of the wearer.

U.S. Pat. No. 9,588,343 to Moravetz, entitled "Menu Navigation in a Head-Mounted Display" discloses a method to navigate a virtual menu by tracking position and orientation (P&O) of a HMD with respect to a focal point of the HMD.

U.S. Pat. No. 9,696,797 to Abdollahi, entitled "Control Systems and Methods for Heads-Mounted Information Systems" discloses a method for navigating a virtual menu through gesture control.

U.S. Pat. No. 9,804,669 to Fateh, entitled "High Resolution Perception of Content in a Wide Field of View of a Head-Mounted Display" discloses a method for controlling the resolution of a virtual image based on the focal point of the wearer. The resolution of the display area currently within the user's focal point is increased, as well as for a display area predicted to be subsequently within the wearer's focal point. The resolution for a display area between these two areas of focus is decreased.

U.S. Pat. No. 9,897,805 to Stafford, entitled "Image Rendering Responsive to User Actions in Head Mounted Display" disclose a head mounted display that incorporates eye tracking to predict subsequent motion of the wearer's gaze. The quality of rendered images is adjusted based on the predicted motion.

US patent publication US20120027373 A1 to Chuang, entitled "Head-Mounted Display Device Having Interactive Function and Method Thereof" discloses a head mounted display that adjusts a displayed image based on the detected motion of the display device.

US patent publication US20150220142 A1 to Parkinson, entitled "Head-Tracking Based Technique for Moving On-Screen Objects on Head Mounted Displays (HMD)" discloses a method to control a cursor on a display of a HMD device using a head tracking controller.

US patent publication US20150346813 A1 to Vargas, entitled "Hands Free Image Viewing on Head Mounted Display" discloses a head-gesture based user interface for controlling the display of a HMD device. Display features controllable via head gestures include zooming in and out of a displayed image, panning a displayed image, scrolling along a series of displayed images, and switching between different operating modes.

US patent publication US20170031538 A1 to Andersson, entitled "Optical Head Mounted Display, Television Portal Module and Methods for Controlling Graphical User Interface" discloses entering a mode for controlling a graphical user interface (GUI) through eye tracking and head motion of the wearer.

US patent publication US20170242495 A1 to Zhang, entitled "Method and Device of Controlling Virtual Mouse and Head-Mounted Displaying Device" discloses incorporating head motion detection for controlling a virtual mouse for a head mounted display.

US patent publication US20170273549 A1 to Nazareth, entitled "Portable Surgical Methods, System, and Apparatus" discloses a kit for housing surgical equipment, including a camera to acquire live images of a surgical procedure, a wireless headset to display a live feed of the acquired images, voice activated control of the system, and a computer for storing data relating to the surgical procedure.

US patent publication US20180113507 A1 to Abdollahi, entitled "Control Systems and Methods for Head-Mounted Information Systems" discloses a gesture control mode for a head mounted display (HMD) device. The gesture control mode is enabled on detection of a gesture control enable signal, allowing the user to navigate a menu via gestures.

SUMMARY

It is an object of the disclosed technique to provide a novel method and system for a user interface for a head mounted display system.

In accordance with the disclosed technique, there is thus provided: a head mounted display configured to be worn by a surgeon; a tracker configured to track head gesture inputs by the surgeon; a footswitch configured to detect a foot motion input by the surgeon; a computer coupled to the head mounted display, the tracker, and the footswitch; and a user interface comprising at least: the head mounted display, the tracker, and the footswitch, and configure to: provide to the computer a head gesture input received from the tracker in association with a foot motion input received from the footswitch, and display an image relating to a surgical procedure on the head mounted display, wherein the computer is configured to: apply the head gesture input received in association with the foot motion input to perform a first action on the head mounted display system when the head mounted display system is in a first system mode, and perform a second action on the head mounted display system when the head mounted display system is in a second system mode.

In some embodiments, the tracker is at least partially integrated with the head mounted display and is configured to track the head mounted display.

In some embodiments, the tracker is a camera external to the head mounted display.

In some embodiments, the system further comprises a shutter coupled to the head mounted display, wherein the head mounted display is at least partially transparent where the shutter is open and the head mounted display is substantially opaque where the shutter is closed.

In some embodiments, one of the first action and the second action controls the shutter.

In some embodiments, the user interface further comprises a microphone configured to detect a voice command, wherein the input further comprises the voice command.

In some embodiments, the user interface further comprises an eye tracker configured to detect an eye motion by the surgeon, wherein the input further comprises the eye motion.

In some embodiments, the system further comprises a camera system configured to acquire the image, an illumination system configured to operate with the camera system, and a positioning mechanism selected from the group consisting of: a camera head positioner and a robotic arm.

In some embodiments, the first action and the second action are selected from the group consisting of: controlling the properties of the image displayed via the HMD, controlling the camera system, controlling the illumination system, and controlling the positioning mechanism.

In some embodiments, controlling the properties of the image displayed via the HMD comprises an action selected from the group consisting of: selecting content of the image, zooming in and zooming out, scrolling between at least two virtual screens, displaying a picture in picture (PIP), displaying an overlay on a live image, centering the image, displaying a menu, navigating a menu, and controlling a region of interest of the image.

In some embodiments, controlling the camera system comprises performing an action selected from the group consisting of: controlling optical and electrical camera characteristics, and controlling a position and orientation of the camera system.

In some embodiments, controlling the illumination system comprises performing an action selected from the group consisting of: selecting at least one of multiple illuminators, selecting an intensity setting, selecting a filter, and turning the illumination on or off.

In some embodiments, the image of the surgical field is displayed via the head mounted display in a display stabilized state when the head mounted display system is in the first system mode, and wherein the video of the surgical field is displayed via the head mounted display in one of multiple virtual screens in a world stabilized state when the head mounted display system is in the second system mode.

In some embodiments, the computer is further configured to apply the head gesture input to switch from the first system mode to the second system mode.

In some embodiments, a first region of a head position and orientation range of the wearer of the head mounted display corresponds to the first system mode, and wherein a second region of the head position and orientation range of the wearer of the head mounted display corresponds to the second system mode, wherein the head gesture input applied to switch from the first system mode to the second system mode is changing the head position and orientation of the wearer of the head mounted display from the first region towards the second region.

In some embodiments, the computer is further configured to display a menu overlaid on the image on the head mounted display, the menu displaying a first menu item for the first system mode and displaying a second menu item for the second system mode.

In accordance with another aspect of the disclosed technique there is provided a method for interacting with a head mounted display system, comprising: displaying, to a surgeon, an image relating to a surgical procedure on a head mounted display; receiving a head gesture input by the surgeon from a head tracker in association with a foot motion input by the surgeon from a footswitch, and applying the head gesture input received in association with the foot motion input to perform a first action on a head mounted display system when the head mounted display system is in a first system mode, and perform a second action on the head mounted display system when the head mounted display system is in a second system mode.

In some embodiments, any of the first action and the second action comprises controlling a shutter coupled to the head mounted display, wherein the head mounted display is transparent where the shutter is open and the head mounted display is opaque where the shutter is closed.

In some embodiments, the method further comprises detecting a voice command by the surgeon and applying the voice command to control the head mounted display system.

In some embodiments, the method further comprises detecting an eye motion by the surgeon, and applying the eye motion to control the head mounted display system.

In some embodiments, the method further comprises illuminating a surgical field with an illumination system configured with the head mounted display system, and acquiring the image of the illuminated surgical field using a camera system configured with the head mounted display system.

In some embodiments, the method further comprises controlling the position of the camera system for acquiring the image via a positioning mechanism selected from the group consisting of: a camera head positioner and a robotic arm.

In some embodiments, the first action and the second action are selected from the group consisting of: controlling properties of the image displayed via the head mounted display, controlling the camera system, controlling the illumination system, and controlling the positioning mechanism.

In some embodiments, controlling the properties of the image displayed via head mounted display comprises an action selected from the group consisting of: selecting content of the image, zooming in and zooming out, scrolling between at least two virtual screens, displaying a picture in picture (PIP), and displaying an overlay on a live image.

In some embodiments, controlling the camera system comprises performing an action selected from the group consisting of: selecting a camera for acquiring the image, and controlling a position and orientation of the camera system.

In some embodiments, controlling the illumination system comprises performing an action selected from the group consisting of: selecting at least one of multiple illuminators, selecting an intensity setting, selecting a filter, and the illumination system on and off.

In some embodiments, the image is displayed via the head mounted display in a display-stabilized state when the head mounted display system is in the first system mode, and wherein the image is displayed via the head mounted display in one of multiple virtual screens in a world-stabilized state when the head mounted display system is in the second system mode.

In some embodiments, the method further comprises applying the head gesture input received in association with the foot motion input to switch from the first system mode to the second system mode.

In some embodiments, a first region of a head position and orientation range of a wearer of the head mounted display corresponds to the first system mode, and wherein a second region of the head position and orientation range of the wearer of the head mounted display corresponds to the second system mode, wherein the head gesture input applied to switch from the first system mode to the second system mode changes the head position and orientation of the wearer of the head mounted display from the first region towards the second region.

In some embodiments, the method further comprises displaying a menu overlaid on the image on the head mounted display, the menu displaying a first menu item for the first system mode and displaying a second menu item for the second system mode, wherein the head gesture input and the foot motion input are applied to switch from the first system mode to the second system mode by selecting and activating the second menu item.

BRIEF DESCRIPTION OF THE DRAWINGS

The disclosed technique will be understood and appreciated more fully from the following detailed description taken in conjunction with the drawings in which:

FIG. 5A illustrates projected images as perceived by a surgeon when a display module is in a display-stabilized state, constructed and operative in accordance with another embodiment of the disclosed technique;

FIGS. 6E-6J, taken together, show a series of live images with corresponding content displayed in PIP, constructed and operative in accordance with another embodiment of the disclosed technique;

FIGS. 6K-6P, taken together, illustrate a series of live images with corresponding content displayed in PIP, constructed and operative in accordance with a further embodiment of the disclosed technique;

FIGS. 8A-8B, taken together, show a technique for correcting a distortion of a 3D image caused by a discrepancy between the actual working distance and designed working distance of the cameras, constructed and operative in accordance with the disclosed technique;

FIGS. 8C-8E, taken together, illustrate the optical system of FIG. 8A at different working distances, constructed and operative in accordance with an embodiment of the disclosed technique;

FIG. 8F illustrates the optical system of FIG. 8A configured to focus on two different focus planes, constructed and operative in accordance with an embodiment of the disclosed technique;

DETAILED DESCRIPTION

Figure 1A:
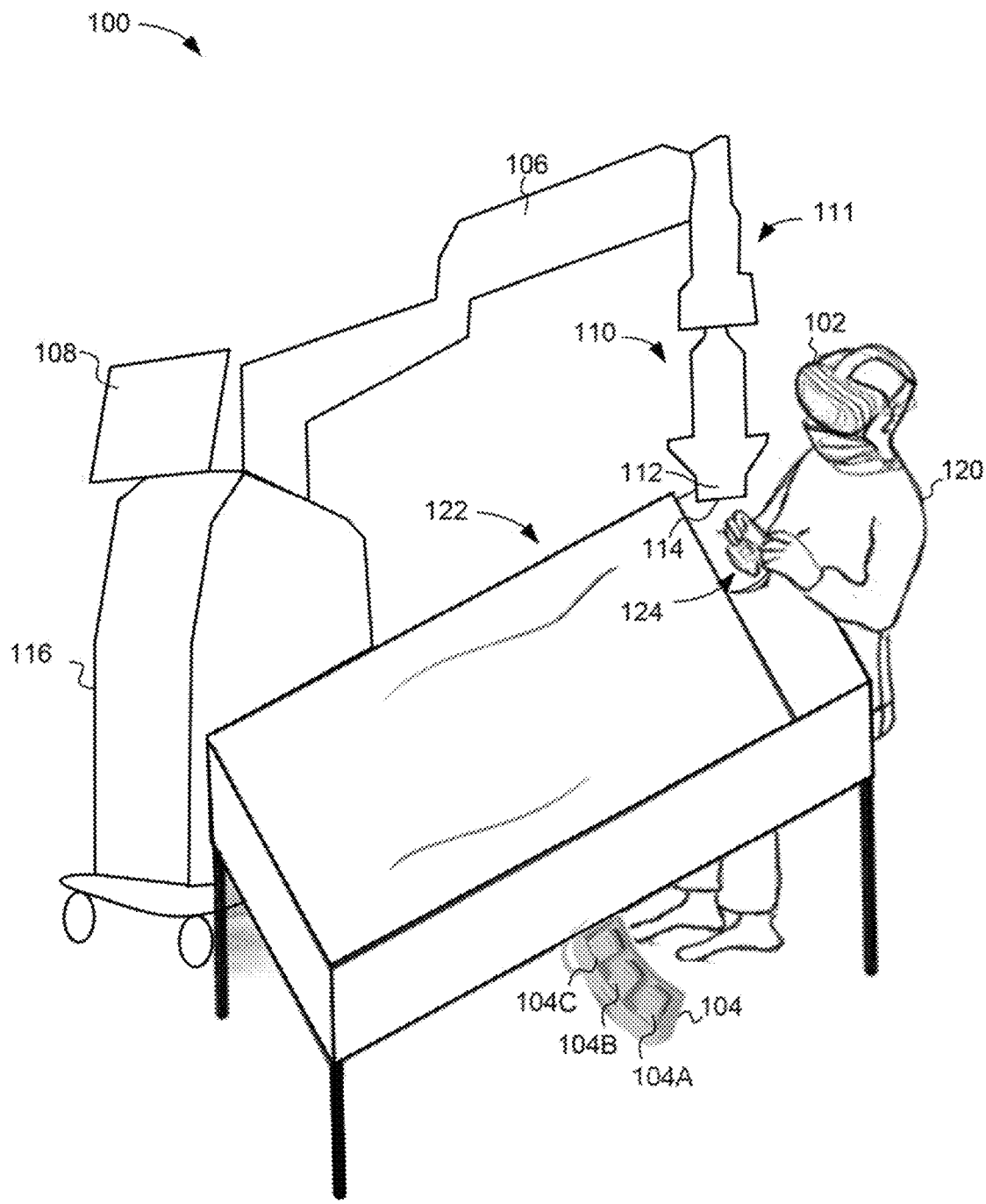
FIG. 1A is a schematic diagram of a system for controlling multiple operating modes for a head mounted display (HMD) coupled to a camera head, constructed and operative in accordance with an embodiment of the disclosed technique.

The disclosed technique overcomes the disadvantages of the prior art by providing a multi-modal user interface (UI) for a head mounted display (HMD) for use in surgical applications. An example of such surgical applications is microsurgery procedures, which are performed under magnification of a surgical microscope. Microsurgical techniques are commonly used in ocular surgery and brain surgery. Typically in microsurgical procedures, a surgeon's hands are occupied with the surgical tools, and he thus requires a wide range of hands-free methods to interface with the surgical microscope and control system parameters. The more robust the system and the wider the range of features it offers, the more complex the interface for controlling these features. The added challenge of providing for such an interface using a hands-free method transfers the complexity to other input means, such as a footswitch. Indeed, surgeons often must use a complex footswitch to control a range of system parameters, and must remove their shoes and use their toes to grope buttons and pedals while their eyes are focused on the surgical field.

The UI of the disclosed technique allows the surgeon to use a relatively simple footswitch while still offering a wide range of functionalities through different system modes, each of which support a different set of actions. In one implementation, the footswitch has only three pedals, allowing the surgeon to easily locate the appropriate pedal while wearing his shoes and without raising his heel from the floor. A given hands-free gesture can trigger a number of different actions depending on the system mode. This technique provides the surgeon with a broad range of functionalities using a relatively small number of hands-free gestures. The hands-free gestures are designed to be intuitive, allowing the surgeon to interface naturally with the system and control the various features, allowing the surgeon to devote the bulk of his attention as well as his hands to the surgical procedure. The surgeon may switch between system modes through one or more hands-free inputs, such as motion sensing, foot or voice control, eye tracking, and the like. In some embodiments, the surgeon switches between system modes through head gestures enabled with the footswitch.

The system described herein includes multiple components, such as a camera system and an illumination system for acquiring images of a surgical field, as well as a HMD for viewing these images. The different system modes allow the surgeon to control different aspects of the system. Some system modes allow the surgeon to control system parameters such as the magnification setting (i.e. zoom in and zoom out), focus and illumination setting for a camera head unit positioned over the surgical field using gestures. Other system modes allow the surgeon to use gestures to control the display via the HMD, such as by selecting content for viewing, and manipulating displayed images and preoperative data.

The methods described here may also apply to surgical procedures other than microsurgical, i.e. performed without a magnified image of the surgical field, such as visor-guided surgery (herein "VGS") based on tracking and augmented reality capabilities. In these procedures, the HMD augments the surgeon's view of the patient and allows the surgeon to see anatomical features and surgical tools as if the patient's body were partially transparent. These procedures may optionally be performed entirely without a magnified image of the surgical field and therefore without a camera head unit.

Reference is now made to FIG. 1A, which is a schematic illustration of a system for controlling multiple operating modes for a HMD, generally referenced 100, constructed and operative in accordance with an embodiment of the disclosed technique. System 100 includes a HMD 102, a footswitch 104, a mechanical arm 106, a touch-based screen 108, a cart 116 housing a computer 118 (not shown) and supporting touch-based screen 108, a camera head 110, and a camera head positioner 111. Camera head 110 houses a camera system 112 and an illumination system 114. Camera system 112 includes at least two high resolution cameras (not shown). Mechanical arm 106 connects computer 118 to camera head positioner 111 and camera head 110. Computer 118 is electrically coupled to camera head positioner 111, camera head 110, camera system 112, and illumination system 114 via one or more wires and/or cables (not shown) integrated inside cart 116 and mechanical arm 106.

Computer 118 controls the position and orientation of camera head 110 via camera head positioner 111. Camera head positioner 111 includes multiple motors for controlling the position of camera head 100 in the x, y, z coordinates. Camera head positioner 111 additionally includes motors for controlling the tilt of camera head 100. Computer 118 additionally controls operational parameters for illumination system 114 and camera system 112, details of which are provided below.

HMD 102, footswitch 104, and computer 118 are provided with one or more transceivers (not shown). The transceivers are compatible with any suitable wired and/or wireless communications means and protocols, such as an electric or fiber optic cable (not shown), Wifi, BlueTooth, Zigbee, short range, medium range, long range, and microwave RF, wireless optical means (e.g. laser, lidar, infrared), acoustic means, ultrasonic means, and the like. Computer 118 is coupled to HMD 102 and footswitch 104 via the transceivers. Computer 118 streams images to HMD 102 via the transceivers, allowing a surgeon 120 to view the images on HMD 102. The images may be acquired by camera system 112 and processed in real-time by a GPU, for viewing a live video of an operation. Alternatively the images may be acquired preoperatively and stored in memory, and rendered in real-time by the GPU. In some implementations, images may be streamed or downloaded from a remote server, such as a cloud based server. For example, in a VGS procedure a model of a body part generated by segmentation from CT or MRI imageries may be stored in memory and rendered on HMD 102 in real-time by the GPU from the perspective of surgeon 120. In other embodiments, the images transmitted to HMD 102 are acquired from an external device, such as an endoscope. Computer 118 determines which images to stream to surgeon 120 based on the current system mode, as well as one or more inputs received from the surgeon via a user interface.

In one embodiment, a single surgeon 120 wears HMD 102 to view a magnified video of a surgical field 124 while performing a surgical procedure on a patient 122. Camera system 112 acquires a stream of images of surgical field 124, corresponding to surgical procedure performed on patient 122. Computer 118 receives and processes the stream of images and transmits the processed images to HMD 102 via the transceivers. Surgeon 120 views the images via HMD 102, and controls one or more settings of system 100 through the system modes. Each system mode may control a different set of system parameters. Surgeon 120 may switch the system mode to control a selected set of system parameters by performing a handless gesture, such as a head gesture while pressing on footswitch 104, performing an eye motion that is tracked by eye tracker 136, or by using acoustic driven means such as voice control, and the like. Details of these and other user interface methods are provided herein below.

Alternatively, surgeon 120 may directly control one or more system parameters using handless methods, such as by performing a head gesture while pressing on footswitch 104. The same gesture may control different features of system 100, depending on the system mode. For example, pressing on a pedal of footswitch 104 while performing a head gesture may trigger one action when system 100 is in one system mode, whereas pressing the same pedal of footswitch 104 and performing the same head gesture can trigger a different action when system 100 is in another system mode. By providing multiple system modes, a relatively small number of pedals and head gestures can control a wide range of features.

For example, in one system mode, surgeon 120 may zoom-in by pressing on the first pedal of footswitch 104 while moving his head upwards. As a result, surgeon 120 sees a smaller size of surgical field 124, magnified over a larger portion of his field of view. In a different system mode, pressing on the same pedal of footswitch 104 while performing the same head upwards gesture may allow surgeon 120 to scroll upwards within multiple pre-operative images displayed via the HMD 102. The gestures for each system mode are intended to be intuitive to allow surgeon 120 to interface naturally with system 100. Thus, although system 100 offers a wide range of controllable features, controlling those features through the user interface disclosed herein should not require a lengthy training period. Rather, surgeon 120 performs gestures that are intuitive to the feature he wishes to control. For example, when viewing multiple images displayed over multiple virtual screens, surgeon 120 can scroll leftwards to view a screen displayed to the left by turning his head to the left. Control via head gesture may provide for greater accuracy and resolution. For instance, some surgeons find that controlling the focus via head gestures proves to be easier compared with using a footswitch, as head gestures allow more accurate one-shot control, eliminating overshooting or undershooting. In some embodiments, the head gesture trajectory determines which will be performed, and the rate of the head gesture determines the rate of performing the action. For example, by moving his head quickly the surgeon may zoom in quickly, and by moving his head slowly, the surgeon may zoom in slowly.

In some embodiments, footswitch 104 is equipped to enable another set of functionalities via a button press, similar to how pressing the <Shift>, <Cntl>, or <Caps Lock> buttons on a standard keyboard enables a separate set of functionalities for the keyboard. In some embodiments, the second set of functionalities are enabled simultaneously for all the buttons and features of footswitch 104 with a single action by surgeon 120. For example, a single short press on one of the buttons of footswitch 104 (e.g. a button corresponding to a menu) followed by a release of that button enables the second set of functionalities for all the buttons of footswitch 104. An indication that the second set of functionalities has been enabled is displayed to surgeon 120 via HMD 102. The second set of functionalities may alternatively be enabled by a voice command or by other means.

In other embodiments, the second set of functionalities is enabled for each button of footswitch 104 separately. Accordingly, a single short press and immediate release of one of the buttons of footswitch 104, followed by a long press of the same button, may enable a second set of head gestures for that button only. For example, a button that enables XY motor control by head gestures without the "shifting", may enable ROI up-down and left-right panning when "shifted". In some embodiments, one or more buttons of footswitch 104 is equipped to distinguish between a full press and half-way press to enable a different set of functionalities. For example, one of the buttons of footswitch 104 may control illumination for system 100, where a full press of that button controls one aspect of the illumination, such as the coaxial illumination, and a half-way press of that button controls another aspect of the illuminations, such as the flood illumination (e.g. a full press enables head gestures that control coaxial illumination and a half-way press enables head gestures that control flood illumination).

In other embodiments, system 100 supports several HMDs simultaneously. One of the users, e.g. surgeon 120 is designated the "leading" surgeon that is capable of controlling all system settings. In some embodiments, other users wearing HMDs similar to HMD 102 control only the settings of the image displayed via their respective HMD, but do not control parameters external to the HMD they are wearing, e.g. they do not control the focus of camera system 112 and illumination by illumination system 114. In other embodiments, other users wearing HMDs similar to HMD 102 can control one or more settings for system 100.

The description of system 100 that follows is given from two perspectives. A description of an exemplary hardware layout for the components of system 100 is given below with respect to FIGS. 1B-1G. FIGS. 2A-2B describe an exemplary logical layout for the user interface of system 100. It is to be noted that these drawings are intended to illustrate but one exemplary implementation of multiple possible implementations for system 100. These drawings are not intended to limit the invention to any particular implementation.

Figure 1B:
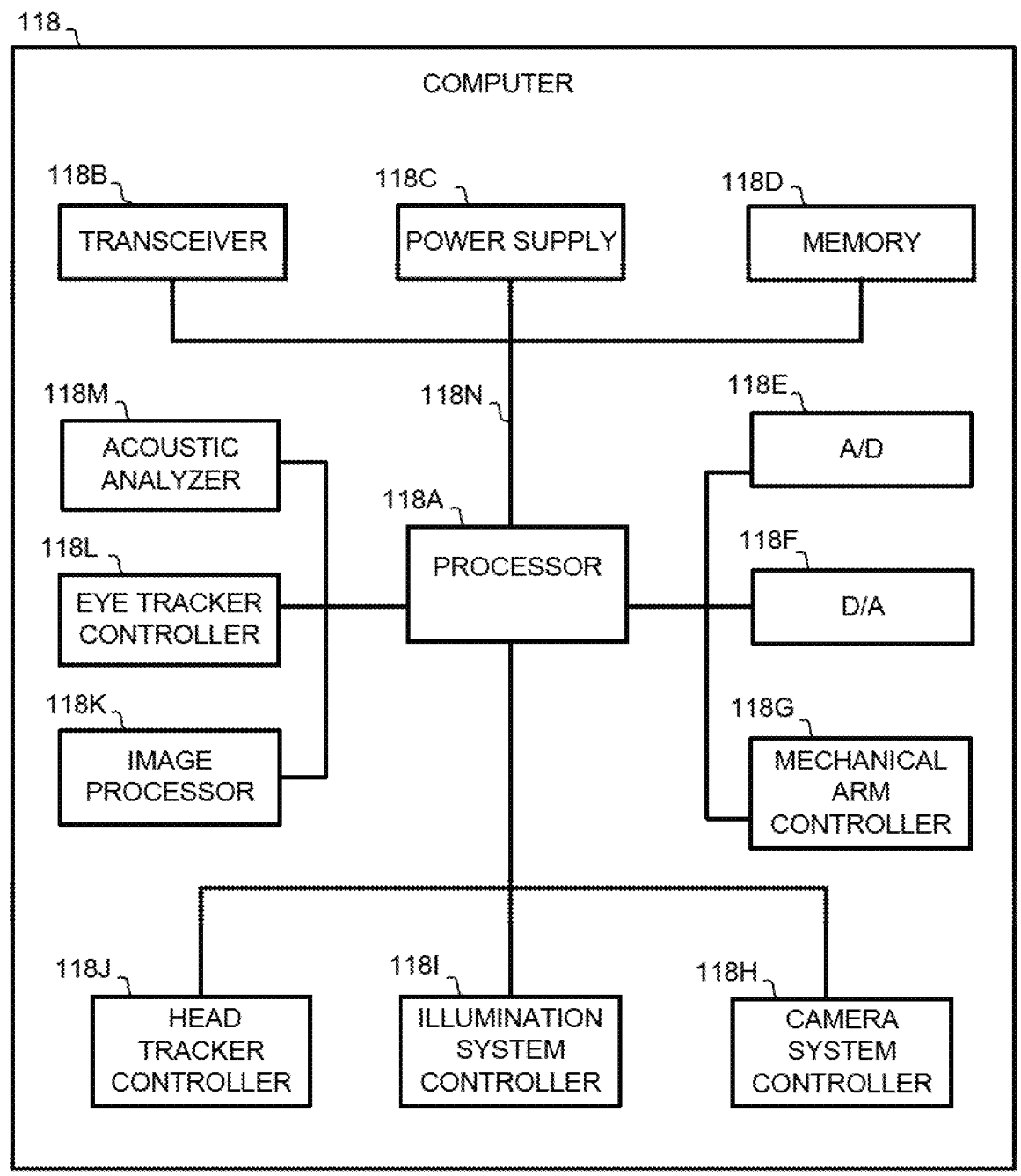
FIG. 1B is a schematic block diagram of a computer, constructed and operative in accordance with another embodiment of the disclosed technique.
Figure 2A:
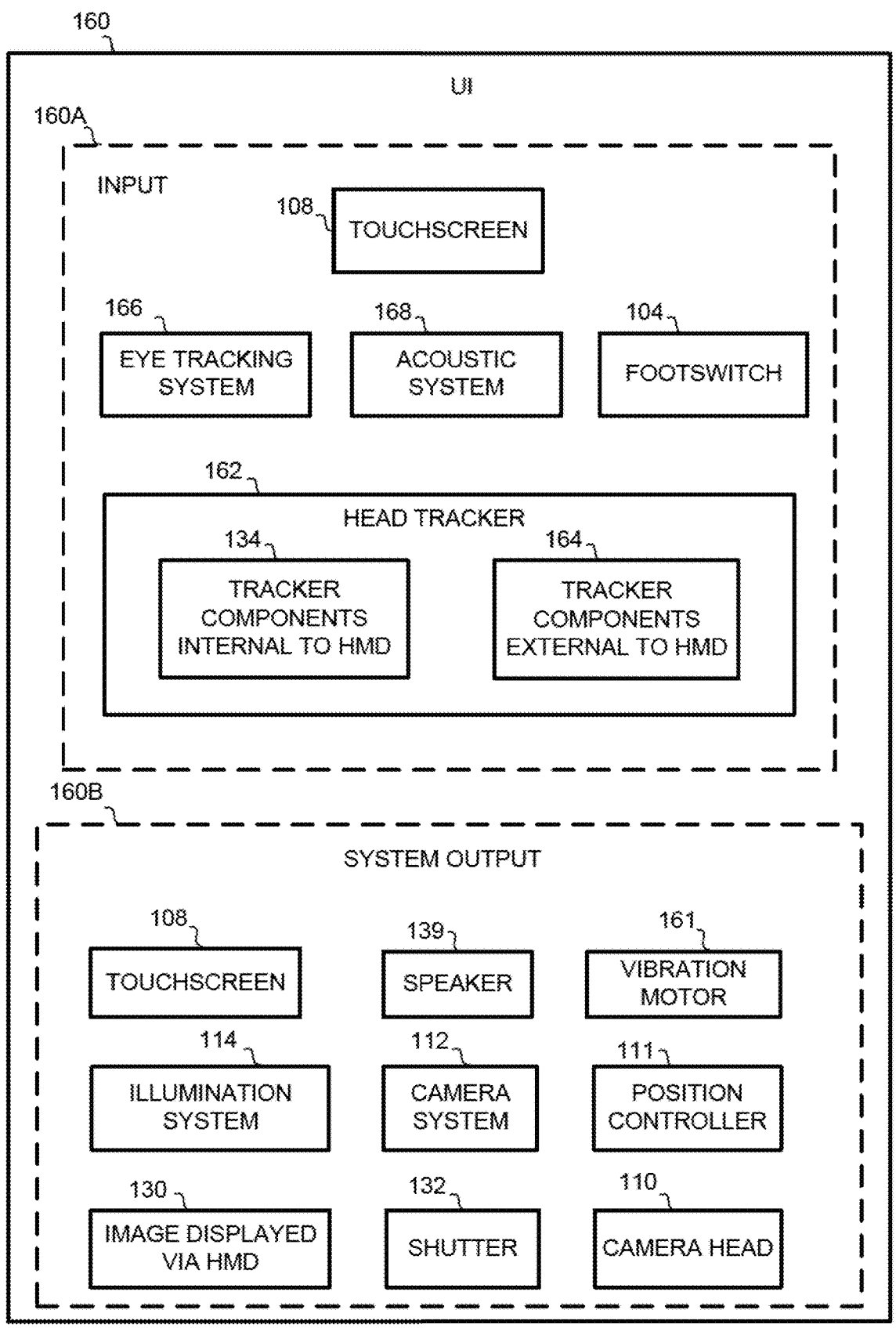
FIG. 2A is a conceptual illustration of the user interface for system 100, constructed and operative in accordance with another embodiment of the disclosed technique.
Figure 2B:
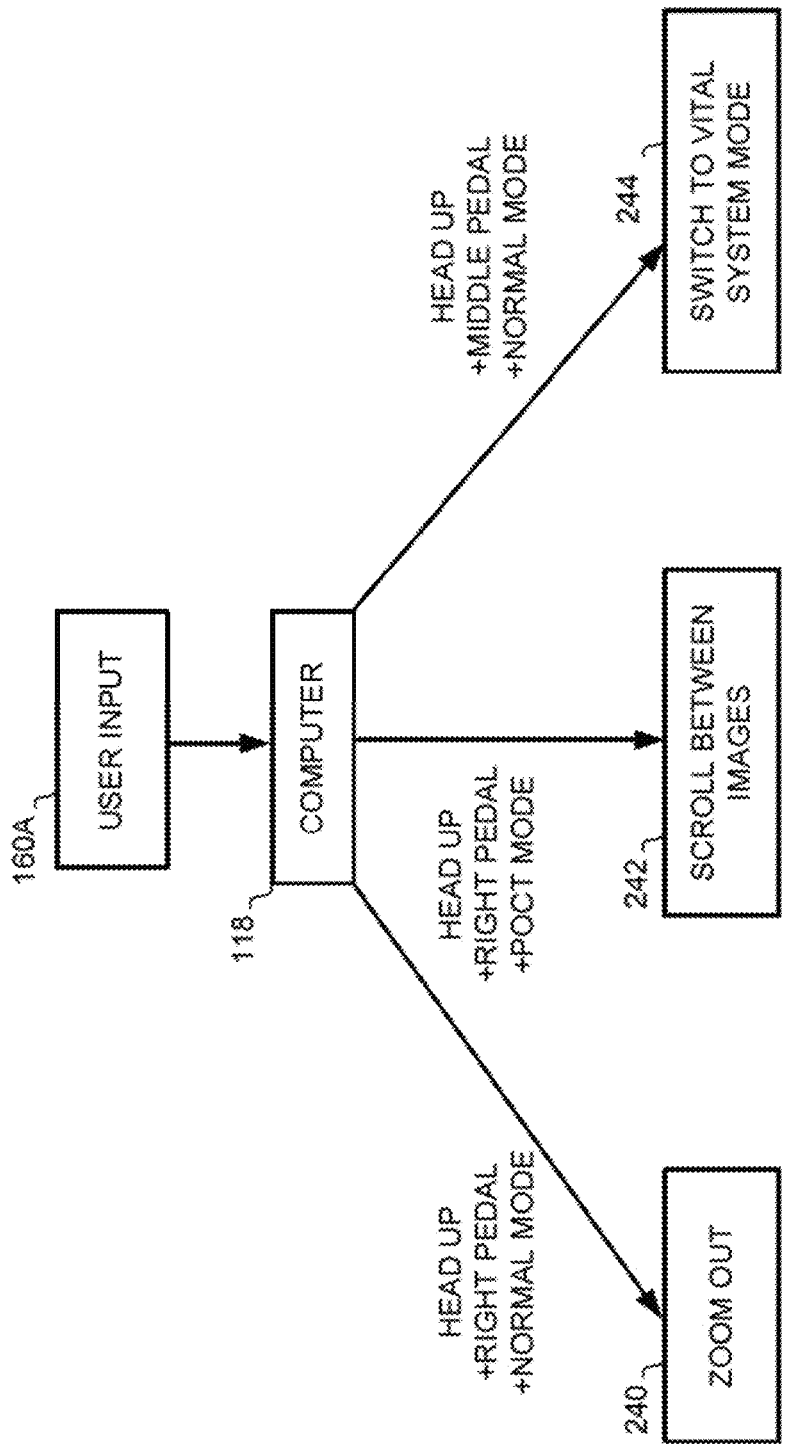
FIG. 2B is a conceptual illustration of a flow of information and control for the system of FIG. 1A via the user interface of FIG. 2A, constructed and operative in accordance with a further embodiment of the disclosed technique.

Reference is now made to FIG. 1B which is a schematic block diagram of computer 118 of FIG. 1A, constructed and operative in accordance with another embodiment of the disclosed technique. It is to be noted that this illustration is but an exemplary implementation, and software modules may replace hardware modules, and vice versa, where applicable. Computer 118 includes at least one processor 118A, at least one transceiver 118B, a power supply 118C, at least one memory 118D, at least one analog to digital A/D converter 118E, at least one digital to analog D/A converter 118F, and one or more of: a mechanical arm controller 118G, a camera system controller 118H, an illumination system controller 118I, a head tracker controller 118J, an image processor 118K, an eye tracker controller 118L, an acoustic analyzer 118M, and at least one bus 118N. Processor 118A, transceiver 118B, power supply 118C, memory 118D, A/D converter 118E, D/A converter 118F, mechanical arm controller 118G, camera system controller 118H, illumination system controller 118I, head tracker controller 118J, image processor 118K, eye tracker controller 118L, acoustic analyzer 118M are coupled via at least one bus 118N.

Although computer 118 is illustrated as a single unit, this is for conceptual purposes only. Computer 118 may be implemented as multiple distributed units that operate as a single controlling unit for system 100. For example, each of at least one processor 118A, transceiver 118B, power supply 118C, and memory 118D may include multiple processors, memories, power supplies, and transceivers that are distributed among the components of system 100 (e.g. among camera head 110, HMD 102, footswitch 104, remote server, and the like) and operate in a coordinated manner.

Mechanical arm controller 118G controls the motors included within camera head positioner 111 to adjust the x, y, z axis or tilt of camera head 110. Camera system controller 118H controls the operation of the cameras included within camera system 112, such as selecting the camera or cameras for acquiring images, adjusting the F-number, focus, and the like. Illumination system controller 118I controls the operation of illumination system 114, such as selecting the illuminator, the intensity, one or more filters, and the like. Head tracker controller 118J controls the operation of one or more head trackers components that are provided with system 100 to track the head of surgeon 120. Image processor 118K processes images received from any of camera system 112, memory 118D, or a GPU, such as by applying a zoom in, zoom out, digital filtering, sharpening, smoothing, color corrections, fusion of several image sources, embedding one image source in another image source in a picture-in-picture form, and the like. Eye tracker controller 118L controls an eye tracker configured with HMD 102. Acoustic analyzer 118M applies sound recognition to sounds received from a microphone provided with system 100, such as by applying voice recognition algorithms to recognize a voice command.

Figure 1C:
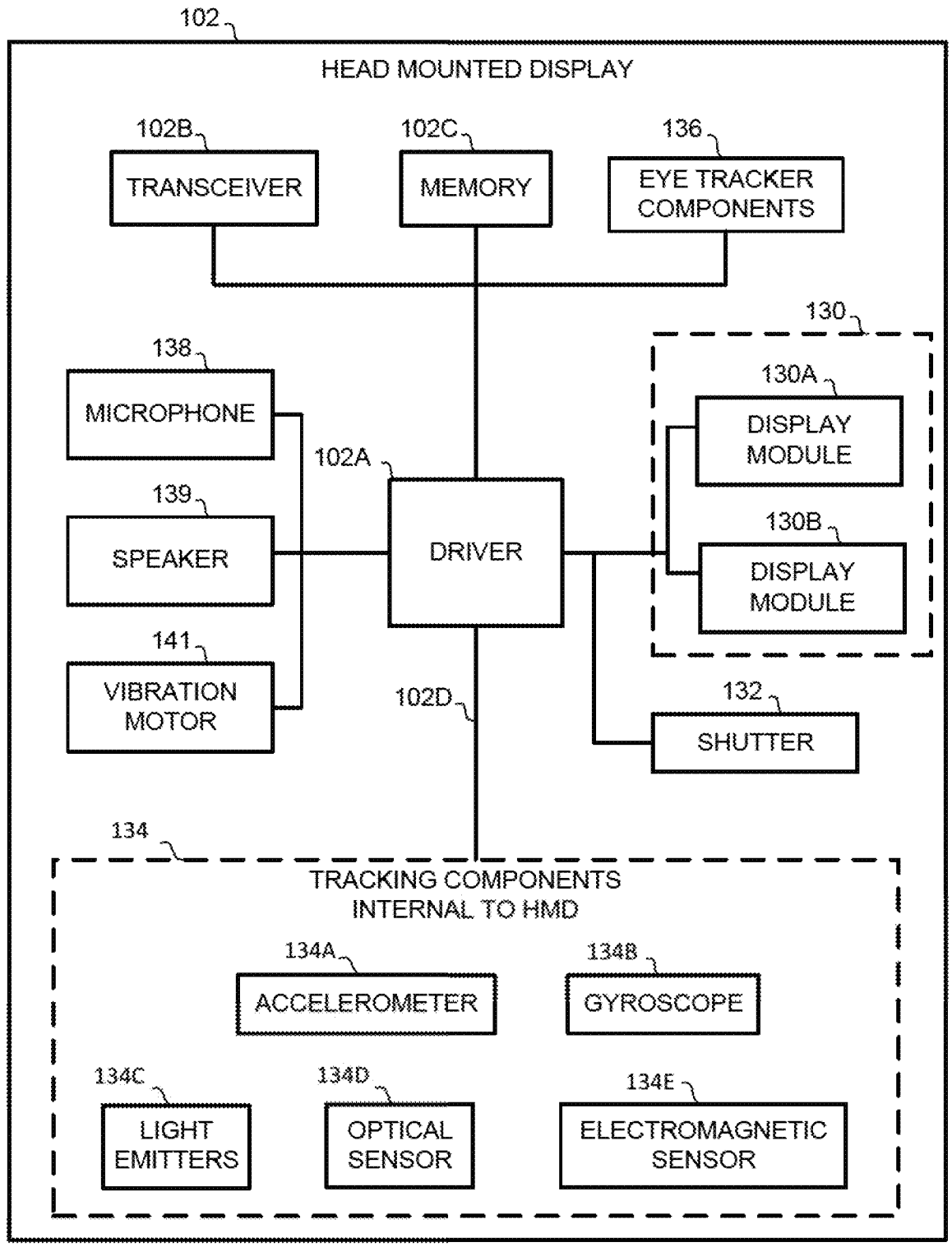
FIG. 1C is a schematic block diagram of the HMD of FIG. 1A, constructed and operative in accordance with a further embodiment of the disclosed technique.

Reference is now made to FIG. 1C, which is a schematic block diagram of HMD 102 of FIG. 1A, constructed and operative in accordance with a further embodiment of the disclosed technique. The components of HMD 102 may be incorporated within an adjustable frame worn by surgeon 120, as shown in FIG. 1A. HMD 102 includes a driver 102A, a transceiver 102B, a memory (e.g. a buffer) 102C, and a display module 130. In some embodiments, HMD 102 additionally includes a liquid crystal (LC) shutter 132, tracking components 134, eye tracking components 136, a microphone 138, a speaker 139, a vibration motor 141, and at least one bus 102D. Driver 102A, transceiver 102B, memory 102C, a display module 130, shutter 132, tracking components 134, eye tracking components 136, microphone 138, speaker 139, and vibration motor 141 are coupled via at least one bus 102D.

Display module 130 may be a binocular display, including two display modules 130A and 130B for projecting an image for each eye of surgeon 120. In some embodiments, HMD 102 is monocular. Shutter 132 is mechanically coupled to display module 130, and is operative to open and close. When shutter 132 is closed, display module 130 is opaque, enhancing an image displayed via HMD 102. When shutter 132 is all or partially open, display module 130 is transparent in the regions where shutter 132 is open, allowing surgeon 120 to see an image overlaid on top of the real world view. Partially or totally opening shutter 132 may be suitable for an augmented reality, or real world view configuration. Alternatively, opening shutter 132 allows surgeon 120 to interact and communicate with other surgeons in the operating theater, such as another surgeon or nurse, as necessary. Tracking components 134 acquire position and/or orientation data for HMD 102 and transmit the position and/or orientation data to head tracker controller 118J via respective transceivers 102B and 118B. Microphone 138 records voice commands or other sounds made by surgeon 120, and transmits the sounds to acoustic analyzer 118M via respective transceivers 102B and 118B. Eye tracking components 136 acquire eye motion data of surgeon 120 and transmit the eye motion data to eye tracker controller 118L via respective transceivers 102B and 118B.

Display module 130 is positioned on HMD 102 to sit along the line of sight of surgeon 120, as illustrated in FIG. 1A. Shutter 132 is configured with display module 130, and can be switched between open, closed, and partially closed states. HMD 102 is transparent wherever shutter 132 is open, and opaque wherever shutter 132 is closed. When shutter 132 is fully open, surgeon 120 views the real world through the optics of display module 130, which is transparent. Shutter 132 may be partially closed, such as for hiding the background behind a feature displayed inside a picture-in-picture (PIP) that is overlaid on display module 130 to enhance the contrast between the feature and the real world view seen through the remainder of display module 130. This is useful when displaying one or more features in a PIP during a VGS procedure in an augmented reality-type application. Display module 130 may be implemented using any suitable technique as is known in the art. Display module 130 may include an image source, such as a small OLED monitor, together with image projection optics, such as waveguide optics, prism optics, projecting onto a visor, and the like. Alternatively, display module may scan an image directly to the retina of surgeon 120 without a monitor. HMD 102 receives the image sources from computer 118.

Tracking components 134 include componentry for tracking the head motion of surgeon 120. Tracking components 134 may include MEMs based accelerometers 134A and gyroscopes 134B, one or more light emitters 134C, optical sensors 134D, electromagnetic sensors 134E, and the like. In some embodiments, tracking components 134 additionally include a compass (not shown). Light emitters 134C may be one or more active light emitting elements, such as light emitting diodes (LEDs), or one or more light reflectors. Tracking components 134 generate translational and rotational motion data of HMD 102, for determining updated orientation and/or position coordinates for HMD 102.

In some embodiments, head tracking is implemented externally to HMD 102, such as by using cameras (not shown). Optionally, tracking components 134 include components external to HMD 102 in conjunction with components internal to HMD 102. In some embodiments, HMD 102 comprises eye tracker components 136 for tracking the line of sight of an eye or eyes of surgeon 120 while wearing HMD 102. In some embodiments, microphone 138 is integrated with HMD 102 to record a voice command of surgeon 120. Alternatively, microphone 138 is external to HMD 102, and may for instance be integrated with camera head 110. It is to be noted that the embodiments described herein are intended as exemplary only, and any suitable combination and configuration of components to achieve the functionality disclosed herein may be used. Computer 118 controls tracking components 134 via tracker controller 118I. Computer 118 communicates with HMD 102 via transceivers 118B and 102B and controls the display of the image feed on HMD display module 130 according to a selected system mode, and additional settings and parameters defined by surgeon 120, described in more detail below.

Figure 1D:
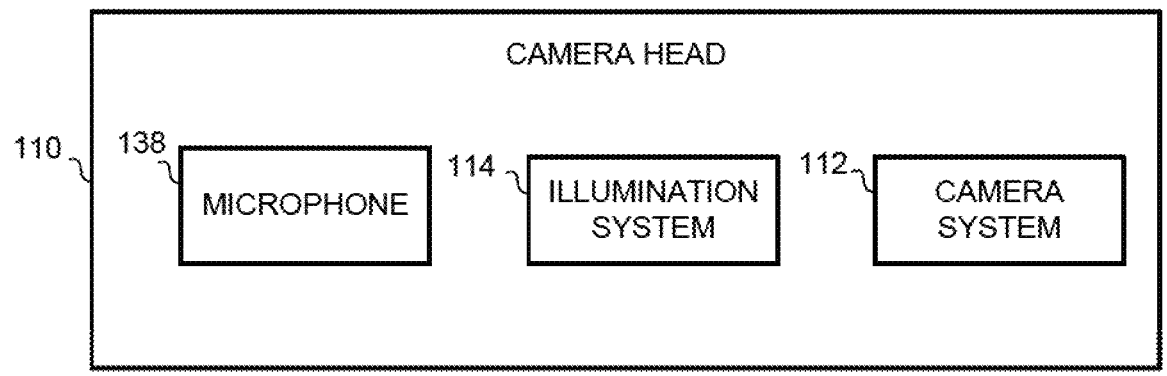
FIG. 1D is a schematic block diagram of the camera head of FIG. 1A, constructed and operative in accordance with another embodiment of the disclosed technique.

Reference is made to FIG. 1D which illustrates a schematic block diagram for camera head 110 (FIG. 1A), constructed and operative in accordance with another embodiment of the disclosed technique. Camera head 110 houses camera system 112, illumination system 114, and optionally microphone 138. In some embodiments, camera head 110 additionally houses a tracking subsystem (not shown) that includes sideway-looking and/or downward-looking optical tracking components, sensors and/or light emitters, and possibly other tracking components. Camera head 110 is mechanically coupled to cart 116 via arm 106 and camera head positioner 111. Camera head 110, camera system 112, illumination system 114, and microphone 138 are electrically coupled to computer 118 (FIG. 1B) with one or more cables and/or wires integrated inside arm 106. Computer 118 controls the xyz-position and tilt of camera head 110 with respect to surgical field 124 by controlling the motors integrated within camera head positioner 111.

In some embodiments, another positioning mechanism, such as a robotic arm, e.g. a 6-DOF (degrees of freedom) robotic arm commonly used for neurosurgical applications, may replace camera head positioner 111 and mechanical arm 106 for controlling the position of camera system 112 to acquire images of surgical field 124. Unlike eye surgery applications where changes to the position and orientation of the cameras are minute, in neurosurgery applications, changes to the position and orientation of the cameras are relatively large. For such applications, surgeon 120 may activate a functionality to lock the control of the cameras to his head, allowing him to control the position and orientation of the cameras of camera head 110 via the robotic arm using head gestures. Surgeon 120 enables this feature via the user interface, such as via footswitch 104, or by issuing voice command, and the like. The head tracking functionality of HMD 102, described in greater detail below, senses rotational and translational movements of HMD 102 and translate them to corresponding rotational and translational movements for the robotic arm controlling camera head 110. Optionally, the user interface allows surgeon 120 to store, or 'bookmark' the current position and orientation for the cameras of camera head 110 so that this position and orientation can be subsequently restored, for example by selecting this feature from a menu displayed via HMD 102.

Computer 118 controls the operation of camera system 112 and illumination system 114 according to the system mode and inputs received from surgeon 120 via the user interface. Computer 118 additionally controls system 100 according to voice commands detected by microphone 138.

Computer 118 may control the display features for HMD 102 digitally or optically/mechanically. For example, computer 118 may implement a zoom-in/zoom-out action digitally by reducing the region of pixels from the full video captured by camera system 112, and stream the reduced region to HMD 102. Alternatively, computer 118 may implement the zoom-in/zoom-out function optically by adjusting the optics of the high-resolution cameras 140A and 140B. Similarly, computer 118 may implement a scroll function digitally by shifting the region of pixels taken from the full video acquired by camera system 112, and stream those pixels to HMD 102. Alternatively, computer 118 may implement a scroll optically/mechanically by adjusting the position of camera head 110 laterally along the XY-axes via camera head positioner 111, shifting the part of the surgical field that is displayed on HMD 102.

Figure 1E:
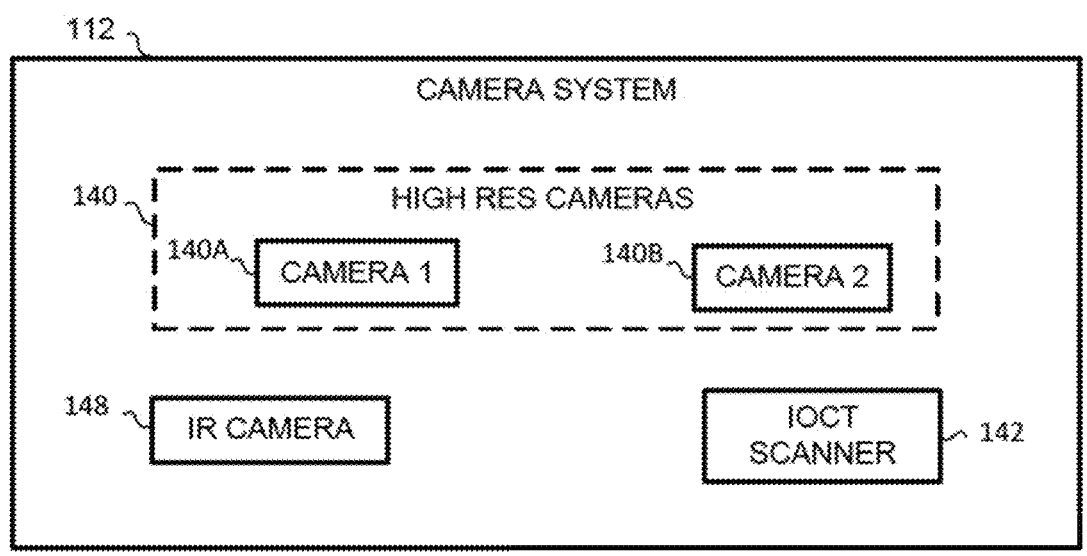
FIG. 1E is a schematic block diagram of the camera system of FIG. 1A, constructed and operative in accordance with a further embodiment of the disclosed technique.

Reference is now made to FIG. 1E which is a schematic block diagram of camera system 112 of FIGS. 1A and 1D, constructed and operative in accordance with a further embodiment of the disclosed technique. Camera system 112 is housed in camera head 110 and coupled to computer 118 via one or more wires and cables integrated within mechanical arm 106 (FIG. 1A). Computer 118 additionally controls each of the components within camera system 112, such as by selecting them for receiving an image feed.

In one embodiment, camera system 112 comprises at least two high resolution cameras 140A and 140B. Cameras 140A and 140B are provided with high precision optics for capturing high resolution and magnified stereo images of surgical field 124. In some embodiments, camera head 110 additionally includes any of an iOCT scanner 142, an IR camera 148, or other cameras for multispectral imaging. Camera system 112 is configured to stream images acquired by cameras 140A and 140B to computer 118, which processes the images and optionally transmits them to HMD 102. The images from cameras 140A and 140B are streamed to the eyes of surgeon 120 via HMD display modules 130A and 130B. The surgeon's brain generates a 3D image from the streamed videos. Computer 118 controls the display of the image feed via the HMD according to the selected system mode, and any additional settings and parameters defined by surgeon 120. Computer 118 controls additional cameras that acquire images used for controlling aspects of system 100 and that are not displayed to surgeon 120. For example, computer 118 controls the IR camera for detecting motion in the operating theater, and the like. Image processor 118L processes the images acquired by camera system 112 according to settings defined by surgeon 120, such as to perform color correction, sharpening, filtering, zooming, and the like. Computer 118 may adjust the lighting, focus, FOV, and magnification for the image feed according to the one or more settings indicated by surgeon 120 via the user interface described below, and stream the processed image feed to HMD 102.

System 100 allows surgeon 120 to select the magnification level for the video acquired by camera system 112 at the beginning of the surgical procedure, and adjust the magnification dynamically throughout the surgical procedure, as necessary. System 100 allows for dynamically updating the region of interest (ROI), zoom, and focus configuration using mechanical, optical, electrical, or digital means. Mechanical and optical updates to the XY positioning and zoom optics for cameras 140A, 140B are implemented via camera system controller 118H (FIG. 1B). Digital zoom functionality and XY-positioning are implemented by changing the size and XY-position of the ROI displayed via HMD 102.

In some embodiments, surgeon 120 dynamically updates the ROI and zoom configuration using head gestures. In some embodiments, surgeon 120 enables system 100 to auto-center camera system 112. In this case, system 100 dynamically updates the XY position automatically. Some examples of dynamic updating include auto-centering, auto-zooming, auto-focusing, and auto-illumination.

System 100 provides an auto-centering functionality for dynamically updating the live image feed. One type of auto-centering follows an illuminated area during retinal procedures in which fiber illumination is used and only part of the retina may be illuminated. Another type of auto-centering follows the center of a patient's eye during anterior procedures, such as cataract procedures (e.g. when the surgeon moves the patient's eye), Yet another type of auto-centering follows a tooltip. It is to be noted that the examples given herein are intended as exemplary implementations only and do not limit the invention. Auto-centering may be implemented on any patient anatomy, any medical device, or in general on any element or information that appears in the image.

Typically, retinal procedures are performed with an extra lens (not shown) suspended from camera head 110 just above the center of the eye of patient 122. Therefore, during these procedures, as long as the patient's eye is not moved, the camera head 110 cannot be moved as well as moving camera head 100 will move this extra lens. This constraint means that adjusting the position of camera system 112 via the XY motor control is not a suitable technique for tracking an illuminated area during retinal procedures. Consequently, as part of the auto-centering functionality, adjustments to the displayed ROI for these procedures are performed digitally, in order to leave the physical position of camera system 112 fixed. The resolution of cameras 140A and 140B is typically higher than the resolution of the display monitors of HMD 102. Therefore, digital adjustment of the ROI is implemented by selecting a subset of the full pixel frames acquired by camera system 112. As surgeon 120 views a small ROI as a zoom on the full image, the ROI can be dynamically selected from the full pixel frames. The centering and specifically auto centering features may be performed using either through controlling the XY motors and/or by adjusting the ROI, depending upon need and context. For example, depending on the type of procedure, one technique may be preferable over another.

In another embodiment, auto-centering over the illuminated area, the center of the patient's eye, a tooltip, and the like, is implemented over discrete time intervals. For example, centering is implemented when the distance between the pupil and the edge of the image is smaller than a predefined threshold, either by changing the ROI or by controlling the XY motors so that the pupil appears in the center of the image. As another example, centering is implemented during a posterior procedure by automatically updating the ROI so that the illuminated spot is centered in the image when the illumination spot on the retina exceeds a predefined margin. This is in contrast to auto-centering continuously such that every frame the image is centered. Auto-centering continuously may pose risks if the patient's eye moves, yet appears stationary to the surgeon.

In a further embodiment, the centering itself is performed in a continuous spatial manner as opposed to a discrete spatial manner. For example, the image is gradually and continuously updated until it is centered (e.g. the XY motors and/or the ROI are affected gradually and continuously), so as to not generate a sudden change in the image.

In another embodiment, prior to centering, system 100 alerts the user of a pending change. The alert may be via a warning displayed in the HMD, via sound, via vibration in the HMD, and the like. The alert warns the surgeon to expect the change in the image and/or a change in the XY position of the camera head unit. Optionally, the user may cancel the pending centering via UI 160. For instance, when an alert is given that the system is about to center the image, the user will have a window of time (e.g. three seconds) to cancel the centering. In a further embodiment, once a centering has been cancelled, system 100 disables subsequent auto-centering. This may be for a predetermined period of time (e.g. five minutes); until a system mode is changed (e.g. by switching from anterior to the posterior mode); or for the duration of the surgical procedure. In another embodiment, once an occurrence of auto-centering is cancelled the system will disable auto-centering until there is a noticeable change in the image, such as may be detected by an image-processing algorithm or by a deep-learning algorithm.

System 100 provides an auto-zooming functionality to dynamically update the live image feed. The auto-zooming feature may be implemented mechanically by controlling the zoom optics inside camera head 110, or alternatively may be implemented digitally on the live image feed via image processor 118K. This configuration allows automatically changing the zoom setting based on surgeon-specific preferences. One type of auto-zooming remembers last zoom power used in each system mode (e.g. anterior), and automatically sets the zoom when the system is turned on and when the mode is switched. Another type of auto-zooming identifies various stages within the procedure and remember surgeon's preferences for each stage. Yet another type of auto-zooming dynamically changes the zoom according to the size of the spot of light generated by the fiber illumination that is held by the surgeon at various distances from the retina and thus changes its size. The zoom multiple corresponds to the size of the spot. As the surgeon moves the fiber tip further away and the spot gets larger, the displayed image is zoomed out. As the surgeon moves the fiber tip closer and the spot gets smaller, the displayed image is zoomed in.

In a similar manner, system 100 allows for manual focusing and auto-focusing. With auto-focusing, surgeon 120 may either designate a point in the surgical field that should be kept in focus. Alternatively, surgeon 120 can have the system automatically focuses on a tip of a tool that the surgeon is holding and manipulating. Alternatively, the surgeon may have the system automatically focus on the center of an illuminated area in retinal procedures. The system will remain focused on the designated location, or instrument, or spot light. In some embodiments, system 100 provides for a one-time focus on a designated point. Surgeon 120 may designate a point on the live image using a combination of a head/foot gesture and/or surgical tool to focus on that point on an as-needed basis.

Figure 1F:
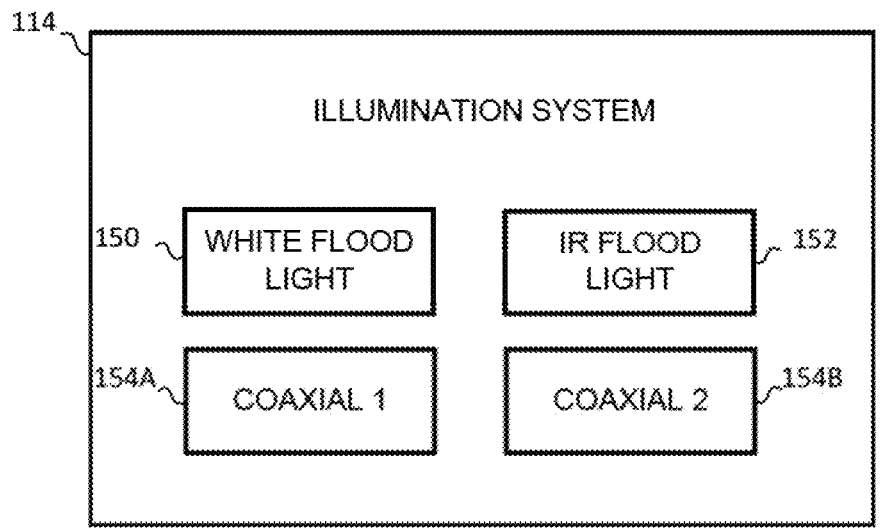
FIG. 1F is a schematic block diagram of the illumination system of FIG. 1A, constructed and operative in accordance with another embodiment of the disclosed technique.

Reference is now made to FIG. 1F, which is a schematic block diagram of illumination system 114 (FIG. 1A), constructed and operative in accordance with another embodiment of the disclosed technique. Illumination system 114 is housed in camera head 110, and coupled to computer 118 via one or more wires and cables integrated within mechanical arm 106. Illumination system 114 includes one or more of: a white flood light 150, an IR flood light 152, a coaxial light 154A, and a coaxial light 154B. Coaxial light 154A and 154B operate with cameras 140A and 140B (FIG. 1E), respectively. In general, illumination system 114 includes at least one visible light emitter to illuminate surgical field 124. The light emitter may be combined with one or more filters (not shown). For example, the illumination may be based on white-emitting LEDs with filters that block out blue light due to light-toxicity considerations, such that the emitted light is not white, per-se. Illumination system 114 may illuminate with non-visible illumination, e.g. infrared (IR) light or ultraviolet (UV) light. In some embodiments, system 100 includes IR illumination combined with a low-resolution/wide field-of-view camera for detecting motion in surgical field 124. Coaxial illumination generates a red-eye effect caused by the reflection of light from the patient's retina, which is used in anterior-segment ophthalmic procedures. Computer 118 controls illumination system 114 with illumination controller 118H, e.g. by selecting the light source, intensity, and the like.

In some embodiments, system 100 allows for auto-illumination. Image processor 118K may analyze the live image feed for under-illuminated or over-illuminated regions and notify computer 118 to manipulate the positioning or intensity by illumination system 114. Optionally, the illumination may be optimized on an element selected by the surgeon, such as a surgical instrument. In some embodiments, system 100 identifies that surgeon 120 has completed a stage and is initiating a new stage, and automatically optimizes the illumination for the new stage. For example, if an external phaco system is streaming data, system 100 knows the mode is now set to phaco mode. In such a case, the flood light is automatically switched off, and the red eye illumination is switched on.

Figure 1G:
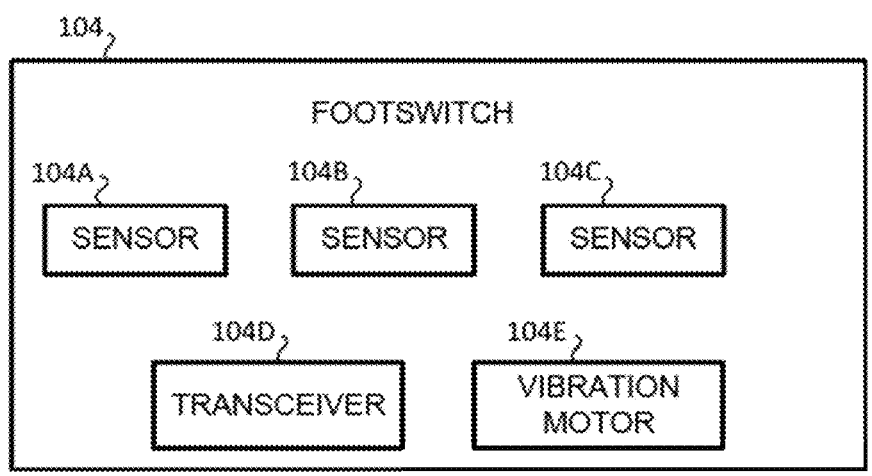
FIG. 1G is a schematic block diagram of the footswitch of FIG. 1A, constructed and operative in accordance with a further embodiment of the disclosed technique.

Reference is made to FIG. 1G which illustrates a schematic block diagram for footswitch 104 (FIG. 1A), constructed and operative in accordance with a further embodiment of the disclosed technique. Footswitch is illustrated with three sensors 104A, 104B, and 104C, a transceiver 104D, and a vibration motor 104E. Footswitch is positioned on the ground adjacent to the feet of surgeon 120. Surgeon 120 controls operating features of system 100 by performing a foot motion detected by footswitch 104. Sensors 104B, 104C, 104D are configured to sense the foot motion, and transmit a notification to computer 118 (FIG. 1B) via respective transceivers 104A and 118A. Sensors 104B, 104C, 104D may be any of a pedal, button, touch-pad, joystick, pressure-based, image-based, and the like. It is to be noted that this implementation is intended to be exemplary only, and footswitch 104 may have more or fewer sensors, or multiple buttons, each with a variety of options. In some embodiments, footswitch 104 is a wearable device configured with inertial sensors for tracking foot gestures. Optionally, a wearable footswitch is additionally or alternatively configured with optical sensors and emitters (not shown) to detect one or more foot gestures. For example, an emitter configured with the wearable footswitch projects a pattern onto a surface, such as the floor. One or more optical sensors detect changes to the projected pattern for deducing a foot gesture. The optical sensors may be configured with the wearable footswitch, but this is not required. Vibration motor 104E provides feedback to surgeon 120 via footswitch 104 regarding settings and system parameters for system 100. Reference is now made to FIG. 2A, which illustrates a schematic block diagram for an exemplary user interface (UI) 160 for system 100 (FIG. 1A), constructed and operative in accordance with another embodiment of the disclosed technique. UI 160 is a logical perspective of the components of system 100 described above with respect to FIGS. 1B-1G, that interface with surgeon 120. The components included in UI 160 are intended to be illustrative only, and it is to be understood that components may be added or removed from UI 160, in accordance with various implementations. FIG. 2A shows components from different system units logically grouped according to their function. UI 160 includes two modules: UI-input 160A including components of system 100 that receive inputs from surgeon 120, and UI-output 160B including components of system 100 that serve as outputs, in response to the received inputs. Computer 118 receives user inputs via UI-input 160A, and processes the inputs to issue one or more system responses via UI-output 160B.

UI-input 160A includes a head gesture tracker 162. Head gesture tracker 162 includes tracking components 134 (FIG. 1C) integrated with and internal to HMD 102, and optionally a head gesture tracker components 164 that are external to HMD 102. For example, head gesture tracker components 164 may be a camera positioned in the operating theatre that acquires images of surgeon 120. UI-input 160A further includes footswitch 104 (FIG. 1A) for receiving foot-based inputs, eye tracking system 166, acoustic system 168, and touchscreen 108 (FIG. 1A) for receiving input from another surgeon. Eye tracking system 166 includes eye tracking components 136 (FIG. 1C) coupled to eye tracker controller 118L (FIG. 1B) that together are configured to sense and track the direction of the surgeon's gaze. Acoustic system 168 includes microphone 138 (FIG. 1C) coupled to speech recognizer 118M (FIG. 1B) that together are configured for receiving, detecting and processing acoustic signals and voice commands emitted by the surgeon. In some embodiments, microphone 138 is external to HMD 102.

UI-output 160B includes content displayed via display module 130 (FIG. 1C), shutter 132, touchscreen 108 (FIG. 1A), camera head 110 (FIG. 1D), camera head positioner 111, camera system 112 (FIG. 1E), and illumination system 114 (FIG. 1F). Based on the input received, computer 118 controls the state of shutter 132, the display of content on display module 130, and the display of content on touchscreen 108, as well as control settings for camera head 110, camera head positioner 111, camera system 112, and illumination system 114. In some embodiments, UI-output 160B is connected to one or more systems external to system 100, such as a phacovitrectomy machine, giving surgeon 120 direct control of systems external to system 100 via UI 160. In some embodiments, system 100 additionally supports a connection to a 2D or 3D external monitor (not shown) for displaying any or all of the available video streams, as well as supporting multiple HMDs concurrently.

In some embodiments, UI-output 160B additionally includes a speaker, such as speaker 139 (FIG. 1C) for issuing sound outputs, such as beeps, or vocal messages to inform surgeon 120. In some embodiments, UI-output 160B additionally includes one or more vibration motors 161, such as vibration motor 141 (FIG. 1C) or vibration motor 104E (FIG. 1G). For example, the vibration motor may be an eccentric rotating mass vibration motor (ERM) using a DC vibrating motor, or a linear resonating actuator (LRA) for indicating system parameters to surgeon 120. The vibrating motors may be integrated with any of HMD 102, footswitch 104, or any other component of system 100. For example, vibrations may indicate that an x-motor has reached its motion-limit, or that system 100 has automatically identified a tool positioned too close to the retina. In some embodiments, system 100 monitors the head of surgeon 120 to ensure his posture is ergonomically correct and issues a warning when surgeon 120 positions his head in an ergonomically incorrect posture that may cause neck pain or injury. The warning may be issued for instance via a message displayed by the HMD, a vibration, or issuing an audio warning such as a beep.

Surgeon 120 interacts with system 100 via user interface 160 while wearing HMD 102 and performing a surgical procedure on patient 122. In this manner, using hand-free gestures surgeon 120 can control operating parameters of system 100, such as image processing parameters of computer 118 (e.g. zoom, color correction); the content displayed via HMD 102 (e.g. images acquired by camera system 112, pre-operative data retrieved from memory, overlaid virtual features, opening and closing of virtual screens and menus); the state of shutter 132 (e.g. open, partially open, closed); control settings for illumination system 114 (e.g. which optical emitter, filter, intensity, wavelength, angle), control settings for camera system 112 (e.g. which camera, zoom, focus, shutter); control settings for camera head 110 (e.g. orientation and alignment by adjusting the xyz motors and the tilt); the selection of menu items for controlling any of the above, controlling the system mode, and the like.

In some embodiments, UI 160 allows storing snapshots and videos and recording audio for subsequent use. The audio recordings may be converted to text to use as notes, operational summaries, naming and tagging files. The keywords tags may be subsequently applied by a deep learning algorithm. In some embodiments, system 100 supports an automatic generation of a surgical report, based on predetermined templates having placeholders for pre-op data, snapshots from the live image, voice-to-text of recorded notes/summaries. The automatic report generation supports adding identifying data, such as the name of patient 122, name of surgeon 120, date, time and duration of the surgical procedure, and the like. Where suitable, machine learning and image processing may be applied to acquire data related to the procedure. For example, the type of surgical instruments used, and the image feed of the surgical procedure may be mined to add data to the report. UI 160 provides a "send-to-report" menu-item allowing the surgeon upload selected snapshots and pre-op images to the report. In some embodiments, UI 160 presents an automatically generated billing summary, which may be configured according to predefined templates. The billing summary may include a list of the surgical procedures performed, and the like.

When video and audio are recorded separately, audio recordings are saved with a time-stamp allowing to synchronize the audio with the corresponding video files. Similarly, when audio notes are converted to text, these are saved with a synchronizing time-stamp allowing the notes to be displayed as subtitles on the corresponding video feed.

In some embodiments, UI-input 160A is configured to detect an input as multiple simultaneous hands-free gestures performed by surgeon 120, such as a head gesture detected via head gesture tracker 162 simultaneously with a foot motion detected via footswitch 104. In these embodiments the enable-input from footswitch 104 serves to prevent an inadvertent head motion by surgeon 120 from affecting the operation of system 100, by enabling the head gesture. On receiving the input from UI-input 160A, computer 118 triggers a corresponding action that depends on the system mode.

In some embodiments, surgeon 120 may temporarily set system 100 to an enable-free state, in which default actions are activated by various head gestures without an enable-input from the footswitch 104. For example, surgeon 120 may set the default actions to be focus control for head-up and head-down gestures, and zoom in and out for head left and right gestures; or allow enable-free head-gestures to switch between system modes.

A description of some exemplary user inputs available to surgeon via UI-input 160A to control aspects of system 100 now follow. This list is not intended to be limiting.

Head gestures
- A general user interface method for a surgical HMD that is based on using head gestures. Head gestures are detected by head tracker 162 of UI-input 160A (FIG. 2A). Surgeon 120 may set system parameters such that some head gestures are enable-free, allowing him to control system 100 using head gestures only. For example, for certain stages of a medical procedure, surgeon 120 may prefer to work in an enable-free mode, allowing him to manipulate system 100 using head gestures only, without the enablement via footswitch 104. Surgeon 120 may issue a voice command to this effect, switching off the enablement via footswitch 104, and control features such as zoom or focus only using head gestures. Surgeon 120 uses head gestures to control continuous and discrete system characteristics, such as:
- zoom, focus, illumination intensity by camera head 110,
- scroll within data items, such as preoperative images displayed on display module 130,
- illumination on-off, image enhancement options, enable-disable either directly via head gestures or indirectly via menu control using head gestures.

Head gestures enabled by footswitch 104.
- Footswitch 104 (FIG. 1G) is provided with one or more pedals, such as pedals 104A, 104B, 104C. Each of pedals 104A, 104B, 104C may enable a group of head gestures to control a different set of system parameters. Each group consists of all the used gestures-up-down motions, left-right motions, gaze, small nods, forward and backward motions, and the like. Using footswitch 104 in conjunction with the head gestures allows surgeon 120 to control many more system features than would otherwise be available with only head gestures. Furthermore, enabling the head gesture via an additional user input enhances the system safety by eliminating involuntarily changes, such as inadvertently switching to a different system mode by naturally moving the head.
- For example, a footswitch with three pedals can enable the following five groups of head gestures in the Normal system mode:
  - Left pedal press (104A)
    - Up-down head gesture: focus of the magnified image.
      - Delicate up-down nod: toggle between enable and disable states of auto focusing. For example, when enabling a one-time auto focusing on a designated point, a cross may appear as an overlay on the image, and the user may rotate his head to move the cross in order to designate the point in the surgical field on which to auto-focus. Releasing the pedal will select the designated point. Surgeon 120 may choose via the menu or touchscreen which type of auto-focusing will be activated by nodding his head (e.g. one-time auto-focus on designated point, continuous auto-focusing on designated point, auto-focusing on tool-tip, auto-focusing on center of light spot.
    - Left-right head gesture: zoom of the magnified image.
      - Delicate left-right nod: toggle between enable and disable states of auto zooming
  - Left+middle pedal presses (104A and 104B)
    - Up-down and left-right head gesture: scroll in y and x directions in the magnified image when ROI is displayed.
    - Delicate up-down nod: toggle between enable and disable states of auto-centering based on changing ROI
  - Middle pedal press (104B)
    - Up-down and left-right head gesture: menu navigation.
    - Long gaze: open sub-menu or choose menu to appear in foreground
    - Release middle pedal 104B: activate chosen menu item.
  - Right+middle pedal press (104C and 104B)
    - Up-down and left-right head gestures: move y and x motors.
    - Delicate up-down nod: toggle between enable and disable states of auto-centering based on changing XY
  - Right pedal press (104C)
    - Up-down head gestures: flood illumination intensity.
    - Delicate up-down nod: toggle between on and off states of flood illumination.
    - Left-right head gestures: red-eye (coaxial) illumination intensity.
    - Delicate left-right nod: toggle between on and off states of coaxial illumination.

Acoustic inputs.
- System 100 is configured to respond to acoustic signals detected via one or more microphones 138. Surgeon 120 may issue one or more voice commands and/or sounds to enable or disable a feature, or to switch to a different system mode, modify or enhance the displayed image, and the like. Acoustic inputs are detected by microphone 138 and processed by computer 118. For example, surgeon 120 may use one tongue-clicking sound to enable/disable one feature, and a second sound to enable/disable a second feature. The sounds for enabling features of system 100 may be user-specific and may be customized by surgeon 120. Surgeon 120 may teach system 100 to recognize a set of preferred sounds. A microphone (not shown) positioned physically close to the mouth of surgeon 120 (e.g. part of HMD 102) may pick up very quiet sounds that are outside the audio range of patient 122. This may be advantageous in procedures that are performed without anesthesia, such as in many surgical procedures of the eye. In these situations, it may be preferable that patient 122 does not hear voice commands uttered by surgeon 120 to control system 100.

Hand gestures.
- In some embodiments, system 100 provides for one or more hand gesture inputs acquired by a hand-held controller (not shown), or by an external tracker (not shown) that sense hand gestures performed by surgeon 120 and transmit these to computer 118 for processing. For example, the hand-held controller may be designed similar to an electronic mouse, a remote control, joy stick, or may be a wearable device, e.g. bracelet or ring. Alternatively, hand gestures may be acquired optically by cameras and/or other sensors integrated in the HMD or elsewhere. The hand gestures may be used in conjunction with any of the UI techniques disclosed herein. For example, hand gestures may be used in conjunction with menus or virtual 3D buttons that are "locked" to a position in the operating room or onto the eye of the patient. In some embodiments, system 100 detects hand gestures by tracking the user's fingers. In other embodiments, system 100 detects hand gestures by tracking surgical tools held by surgeon 120, allowing the surgeon 120 to "touch" and "press" a menu item or a virtual 3D button with a surgical tool.

Physical control via camera head 110.

Camera head 110 may be provided with one or more manually operated buttons, handles, and switches, and control panels. These may be controlled by surgeon 120 or an attending nurse.

User eye-tracking combined with menus or buttons displayed virtually.

Surgeon 120 may navigate displayed virtually menu options via eye tracker 136 (FIG. 1C). For example, surgeon may gaze at a virtual menu item for a predefined period of time, or blink according to a pattern, or by performing other such "eye gestures". This UI may be used in conjunction with any of the other UIs described herein. In addition to display-stabilized virtual menus, menus may be world-stabilized or anatomy-stabilized. For example, 3D virtual buttons may be displayed "locked" to the eye of patient 122, such as at the periphery of the treated area. Surgeon 120 may "press" one the displayed button by gazing at the virtual button, and eye tracking components 136 detect the gaze.

Touchscreen.

Control and operational parameters for system 100 may be set, monitored and modified via touchscreen 108. Touchscreen 108 may be covered by a sterile nylon for use by a scrub nurse or by surgeon 120. In addition to controlling operational settings by surgeon 120 wearing HMD 102, touchscreen 108 allows to control modes, settings and preferences that cannot be controlled by surgeon 120 wearing HMD 102. Touchscreen 108 may display any of the video feeds that are available to system 100, either in their raw form or in the format seen by the wearer of HMD 102, e.g. with overlays, PIPs, etc.).

The system mode determines how system 100 interprets and reacts to a user input performed by surgeon 120, modifying the user-interface configuration. For example, in the Pre-op mode, surgeon 120 scrolls through multiple images displayed via HMD 102 by turning his head while simultaneously pressing on a pedal of footswitch 104. In the Normal mode, surgeon 120 zooms in or out of the image displayed via HMD 102 by moving his head left (zoom in) or right (zoom out) while simultaneously pressing on a pedal of footswitch 104. In some embodiments, computer 118 only enables performing an action while the appropriate pedal of footswitch 104 is pressed.

Following are several exemplary system modes provided by system 100, and the characteristics that they control. The system modes define which parameters are manipulated for system 100, such as the display settings for HMD 102, or the operational settings for camera system 112. Surgeon 120 selects and initiates a mode through combinations of UI inputs, including head gestures, eye motion, voice commands, and foot motions that are detected by UI 160A. Computer 118 processes the UI inputs and triggers a system response via one or more system output components of UI 160B. The system mode determines the response, such as one or more of: the content displayed on HMD 102, the screen state, the state of shutter 132, the UI functionality; and operational settings for camera head 110, and the like. The following exemplary list of modes is not intended to be exhaustive, nor does it include all of the characteristics controllable through each system mode.

Normal mode (default mode). In this system mode, the default values are typically in effect, but can be customized by surgeon 120. The image feed acquired by camera system 112 is displayed via HMD 102. Surgeon 120 uses UI 160 primarily for controlling display attributes, such as the zoom, focus, XY position for camera system 112, and the illumination settings for illumination system 114.

Transparent mode. In this system mode, display module 130 is turned off, and LC shutter 132 is open, allowing surgeon 120 to see the real world view.

Posterior non-contact lens mode. This system mode allows surgeon 120 to view surgical field 124 in an inverted, or posterior mode. The settings for this mode are as follows:
  Eye inversion—inverted,
  Flood illumination—off. This may be user configurable,
  Red-eye illumination—off,
  Color scheme—fiber illumination (color correction is source-specific),
  Image enhancements—posterior-specific values, and
  Motors states—limited velocities and boundaries. These parameters may be limited by the surgeon by controller the rate or speed of the head gesture.

External modes. These system modes correspond to additional external devices (not shown) that may be connected to system 100, for example, an endoscope. One of the external system modes has the following settings:
  Red-eye illumination—on. The intensities for red-eye and flood illumination are predefined.
  Overlay—additional data are overlaid from an external system.
  Functionality for UI 160 may be customized. For example, definitions for footswitch 104 may differ in this mode than for other modes. This is to allow surgeon 120 to control the external machine using footswitch 104. The menu displaying options may also be modified accordingly, to reflect the different functionality.

Pre-operative data mode ("Pre-op" mode). In this mode the user views pre-planning data, such as pre-operative images or notes prepared by him and/or patient data and/or, and the like. After viewing the data, the user returns to the previous mode to continue the surgical procedure. The user may also select a set of images that he will be able to see in a PIP from a library of images, and scroll within the selected images after returning to the previous mode, as described in greater details below in FIGS. 6C-6J. The settings for this mode are as follows:

Display content. In place of the live magnified images acquired of surgical field 124, the HMD displays a GUI allowing the user to access any data he or she desires, browse and view the data.

UI functionality. This mode allows browsing and scrolling the pre-op data. For example, a gesture in the Normal mode might control zoom or focus of the magnified image. In the pre-operative data mode the magnified image is not displayed, and the same gesture allows scrolling through the displayed pre-operative data, and the like.

Illumination. Illumination by illumination system 114 may be set to minimum in the pre-operative data mode, or alternatively turned off, dimmed, switched to another emitter included therein, such as by IR illumination with IR flood light 152. IR illumination allows detecting the motion of an attending nurse while surgeon 120 is viewing the pre-operative data, and may be turned on automatically. The illumination may be returned to its previous, non-IR setting once surgeon 120 switches back to the Normal system mode.

PIP (picture-in-picture) system mode. The display of picture-in-picture (PIP) allows displaying preoperative images, live video feeds, snapshots of previously acquired video, GIFs, and data such as vital signs, and other data, in a window overlaid on the current background image displayed via HMD 102. Surgeon 120 may predefine several different PIPs, their locations, and what content to display in each PIP. For instance, the PIP may display preoperative OCT images when working in the Posterior non-contact lens mode, or display the live magnified image when in Endoscope mode and the background image is a live video feed from an endoscope camera. Surgeon 120 can turn each predefined PIP on and off. Surgeon 120 can control the position and size and on/off state of the PIP via UI 160. The location of a PIP on the field of view of HMD 102 may be dynamically changed according to the location of the automatically-detected area-of-interest in the main image, and may be set by surgeon 120 via UI 160. The location of a PIP may also be locked to the real world ("world-stabilized PIP") or to the patient anatomy, for instance in VGS procedures. When in PIP mode (i.e. after "selecting" the PIP), activating snapshot may save the PIP image only. This may be useful for instance for saving an iOCT image.

PIP-specific capabilities may be added to the overlaid menu when a PIP is displayed, such as to enable or disable overlay symbols that indicate a location on the live magnified image corresponding to a preoperative image currently displayed in the PIP. In some embodiments, while performing an augmented reality (VGS) procedure, driver 102A of HMD 102 closes shutter 132 in the areas of display module 130 where the PIPs are displayed. This allows surgeon 120 to view the real world through a partially transparent screen, and simultaneously view preoperative, intraoperative, and other data displayed in one or more PIPs while blocking the ambient light behind the PIPs. When the PIP is locked to the patient anatomy computer 118 may dynamically control the regions where the shutter is closed so that the background is always blocked behind the PIP, while surgeon 120 is moving his head.

In some implementations, switching to the PIP system mode is possible only when at least one PIP is displayed via the HMD. Switching to the PIP system mode may be performed for instance by pressing the footswitch button that invokes the menu, and selecting the PIP as if it were a menu item. This causes the UI functionalities to change to predefined UI functionalities according to the content displayed in the PIP. For instance, if the PIP displays preoperative data, the UI is inherited from the Preoperative Data mode (e.g. allowing surgeon 120 to scroll within a set of preoperative images displayed inside the PIP), and if the PIP displays the live magnified image the UI is inherited from the Normal mode or the Posterior Non-contact Lens mode (e.g. allowing surgeon 120 to control the magnification), or in general the last selected mode for viewing the live magnified feed (as several other such modes may exist that were not specified here). Special UI capabilities may be added to the inherited UI in PIP mode and other may be fine-tuned for PIP mode. For instance, when preoperative images are displayed in the PIP, surgeon 120 may use head gestures to control a virtual pointer and designate corresponding points in the displayed preoperative image and in the live magnified image (this can be performed for manually registering preoperative data to the live image).

iOCT (Intraoperative OCT) mode. This system mode engages iOCT scanner 142 to acquire OCT data. The settings for this mode may include:
iOCT—on.
PIP—on, images acquired via iOCT scanner 142 are displayed in a PIP.
UI options—this feature provides UI options allowing surgeon 120 to control operating parameters for iOCT scanner 142, such as the scanning position and angle, using head gestures, or by navigating a menu, and the like. For instance the user may use the menu to toggle between iOCT scanning types: B-scan and volumetric scan.
B-scan indicators overlay—this feature overlays symbols on a live magnified image indicating the position of the live iOCT B-scan.

Other procedure-specific and stage-specific modes: In general, various procedure-specific and stage-specific modes may be predefined for displaying procedure-specific and stage-specific data and overlays.
Data overlay is enabled, for instance data from a phacovitrectomy machine.
Registered overlay is enabled. This view displays image-registered symbols and/or images and/or 3D models overlaid on the real world magnified view of the surgical field to assist surgeon 120 in the surgical procedure.
UI—the UI functionality may change to allow the user to control the location, depth and orientation of overlays or to control other devices that are connected to the system. For example, an angle of a line overlaying the display that can be manipulated using head gestures and/or the footswitch 104.
PIP (picture in picture). PIP may be enabled to show relevant preoperative or intraoperative video and/or data via the PIP.

External video feeds mode:
In some modes, HMD 102 displays an external video feed, such as may be provided by one or more cameras positioned external to the operating room to allow surgeon 102 monitor the patients waiting in the reception, or to monitor the progress of a different surgical procedure in a different operation room. These videos may be displayed in a PIP or on a side screen of HMD 102. They may be displayed one video at a time or as a mosaic of videos in multiple screens. This mode allows the surgeon to view all the available video feeds in multiple screens. The surgeon may view a video feed from the reception room, other operating theatres, or may search a database of educational videos that demonstrate how to perform rare procedures such as may arise in unpredictable situations. The surgeon may decide in advance when and how to view the selected video, such as in a PIP, and return to the previous mode.

Teaching mode:
- In some embodiments, system 100 may be simultaneously guided by a co-surgeon (not shown), such as a senior surgeon, in conjunction with surgeon 120. The co-surgeon wears a second HMD (not shown) that is coupled to computer 118 and camera head 110, and operates in a similar manner to HMD 102. The second HMD also displays a view of surgical field 124, and the co-surgeon can control a cursor on the display that is synchronized with the display on module 130 of HMD 102, allowing surgeon 120 to see the cursor controlled by the co-surgeon. In this manner, the co-surgeon can guide surgeon 120 during the surgical procedure. Similarly, the co-surgeon may invoke one or more PIPs showing pre-operative or other data to surgeon 120, and the like.
- In this mode the senior surgeon can mentor surgeon 120 who is performing the surgical procedure, such as when surgeon 120 is a resident. In some embodiments, eye tracking components 136 (FIG. 1C) tracks the gaze of surgeon 120 and determines the area of the display of HMD 102 that is being focused on by surgeon 120. System 100 displays a symbol to the co-surgeon via the second HMD that indicates the area focused on by surgeon 120. In this manner, the co-surgeon can monitor the focus of surgeon 120.
- In some embodiments, the senior surgeon can overlay features and symbols to guide surgeon 120 while performing the procedure. Surgeon 120 sees the end effect overlaid on the live image, and will not see the menus and drawing options that the supervising surgeon sees in this mode. Features in the teaching mode include:
  - showing the senior surgeon a "Paint"-like menu for selecting drawing options, choosing a virtual tool/marker/pointer to display, the color of the markings, to erase markings, etc., as described in greater details below in FIGS. 6K-6O.
  - Allowing the senior surgeon to control a pointer or draw using head gestures or with a dedicated wand.
  - when drawing on the real-time image, the drawings (lines, symbols, etc.) may be locked to the anatomy of the patient, i.e. the overlaid symbol will automatically/dynamically change its position so it appears locked to the patient's anatomy (e.g. when the surgeon moves the patient's eye). The drawing may be in 3D.
  - when the senior surgeon is not donning a HMD, she may use the touchscreen to point and draw. The senior surgeon may remotely guide the acting surgeon, for instance using a regular screen and mouse in her office or in her home, and even using a tablet or a smartphone to point and draw on the real-time image.
  - A symbol may be displayed in the corner of a displayed image indicating to the acting surgeon that someone has connected to system 100 in "drawing" mode, and is enabled to draw on the live image feed.
  - An erasing option is provided for the acting surgeon. Once a feature has been drawn onto the display, a menu item is added to the current menu (i.e. the menu is displayed to the acting surgeon if he invokes the menu), allowing the acting surgeon to erase one or more drawn features. The menu may allow to erase all drawn features by selecting a single "erase all" menu item. Alternatively, the menu presents a submenu allowing surgeon 120 to select which drawn features to erase, and how many.
  - A freeze option may be provided that freezes the live image feed, to facilitate the drawing of features.

3D symbols/markers:
- A 3D symbol is a symbol that is displayed to both eyes such that it appears at a given depth relative to the anatomy. A 3D marker generates a 3D image-stabilized symbol (e.g. a 3D line).
- The user may choose a 3D pointer or marker that is fully controlled by the user, i.e. the user controls both its XY position and its depth (the user may manually control the depth, e.g. using head gestures enabled by a depth-control pedal).
- The user may alternatively choose a 3D pointer or marker that automatically locks to the depth of the anatomy that is currently in focus, and as the user moves the symbol, the user gets the sensation that the symbol follows the surface of the anatomy (e.g. goes up and down).
- When the latter is used, the height is automatically calculated and updated if the focus is changed by the user. For instance if a first point-of-focus is on a transparent surface like the cornea and a second point-of-focus is behind (below) the first one, like a point on the anterior capsule, then the symbol locations in the two images (displayed to the two eyes of the HMD user) change in a different manner to reflect the new depth.

Wand:
- A wand is a mouse-like or a remote-control-like controller, optionally with buttons of various types, hand-held, wireless or wired, optionally in a sterile cover, optionally with integrated inertial tracking. It may be used both for pointing/drawing as described above, and for controlling a virtual tool.
- The supervising senior surgeon may use the hand-held controller for moving a virtual tool in a natural way to show the resident how to perform a surgical maneuver. The virtual tool appears in the display as a 3D tool that the users see as an overlay on the live image via the HMD. This is based on 3D models of tools that are available to the user to choose from via the menu/GUI in this mode.

Surgeon 120 selects and switches the system mode for system 100 using one or more hands-free gestures detected via UI-input 160A. In some embodiments, surgeon 120 switches the system mode by performing a head gesture, detected by head tracker 162, while simultaneously performing a foot motion, detected by footswitch 104. In other embodiments, surgeon 120 switches the system through a voice command detected by microphone 138. Computer 119 determines how to interpret subsequent user inputs according to the system mode.

For example, in one system mode, an upwards rotation of the head by surgeon 120 performed while pressing on pedal 104A of footswitch 104 increases the intensity of the illumination by illumination system 114. In a different system mode, the same head gesture performed while pressing on the same pedal 104A of footswitch 104 scrolls through images displayed via HMD 102. A sideways head gesture performed by surgeon 120 while pushing on pedal 104B of footswitch 104 may switch between these two system modes. By allowing for multiple system responses to the same gestures, the systems modes offer a greater range of functionality for system 100, allowing surgeon 120 to control features of system 100 without using his hands, leaving them free to perform the surgical procedure.

Reference is now made to FIG. 2B which illustrates an exemplary control flow diagram for the user interface of FIG. 2A, constructed and operative in accordance with a further embodiment of the disclosed technique. Computer 118 (FIG. 1B) receives a user input via UI-input 160A, such as a head gesture from head tracker 162 simultaneously with an indication of a foot press on a pedal of footswitch 104 (FIG. 1G), and determines a system response depending on the system mode, i.e. the response is mode-specific. In one system mode, the user input causes a first action on system 100, and in a different system mode, the same user input may cause a different action on system 100. The flow diagram of FIG. 2B is intended to illustrate the flexibility and range of functionalities that may be controlled via user interface 160 in conjunction with the multiple system modes. This illustration is intended as exemplary only, and is not intended to limit the invention to any specific implementation or examples disclosed herein.

Computer 118 receives the user input from head tracker 162 and footswitch 104 UI-input 160A. Case 1: The user input is an indication that surgeon 120 performed head up gesture while pressing on pedal 104A of footswitch 104. Since the current system mode is Normal, computer 118 implements a zoom-out on image displayed on HMD 102, indicated as action 240. Case 2: The user input is the same indication as before, e.g. surgeon 120 performed a head up gesture while pressing on pedal 104A of footswitch 104. However, since the current system mode is set to pre-operative OCT ("Pre-op" mode), computer 118 implements a scroll between preoperative OCT images, indicated as action 242. Case 3: The user input is an indication that surgeon 120 performed head up gesture while pressing on pedal 104B of footswitch 104. Since the current system mode is Normal, computer 118 switches the system mode from Normal to Vital, indicated as action 244. Mode switching is described in greater detail below with respect to FIG. 3A.

By responding to multiple user inputs obtained from the multiple user interfaces described herein, system 100 allows surgeon 120 to control a wide range of operating features while freeing his hands to perform the surgical procedure. An input may trigger one system response in one system mode, and a different system response in a different system mode, offering a wide gamut of functionalities through a relatively small set of inputs, e.g. head gestures, foot presses, voice commands, and the like. Footswitch 104 operates to control the response of system 100 only to deliberate gestures by surgeon 120. Inadvertent gestures by surgeon 120 will not cause a response by system 100 if footswitch isn't simultaneously pressed.

According to one embodiment, surgeon 120 may select the system mode by controlling the position and orientation of HMD 102. The range of possible positions and orientations for HMD 102 is divided into multiple zones, each zone corresponding to a different system mode. By moving his head to align the position and orientation of HMD 102 with a zone, surgeon 120 can select the system mode corresponding to that zone. System 100 may require surgeon 120 to press on footswitch while maneuvering his head to prevent inadvertently switching to a new mode.

Figure 3A:
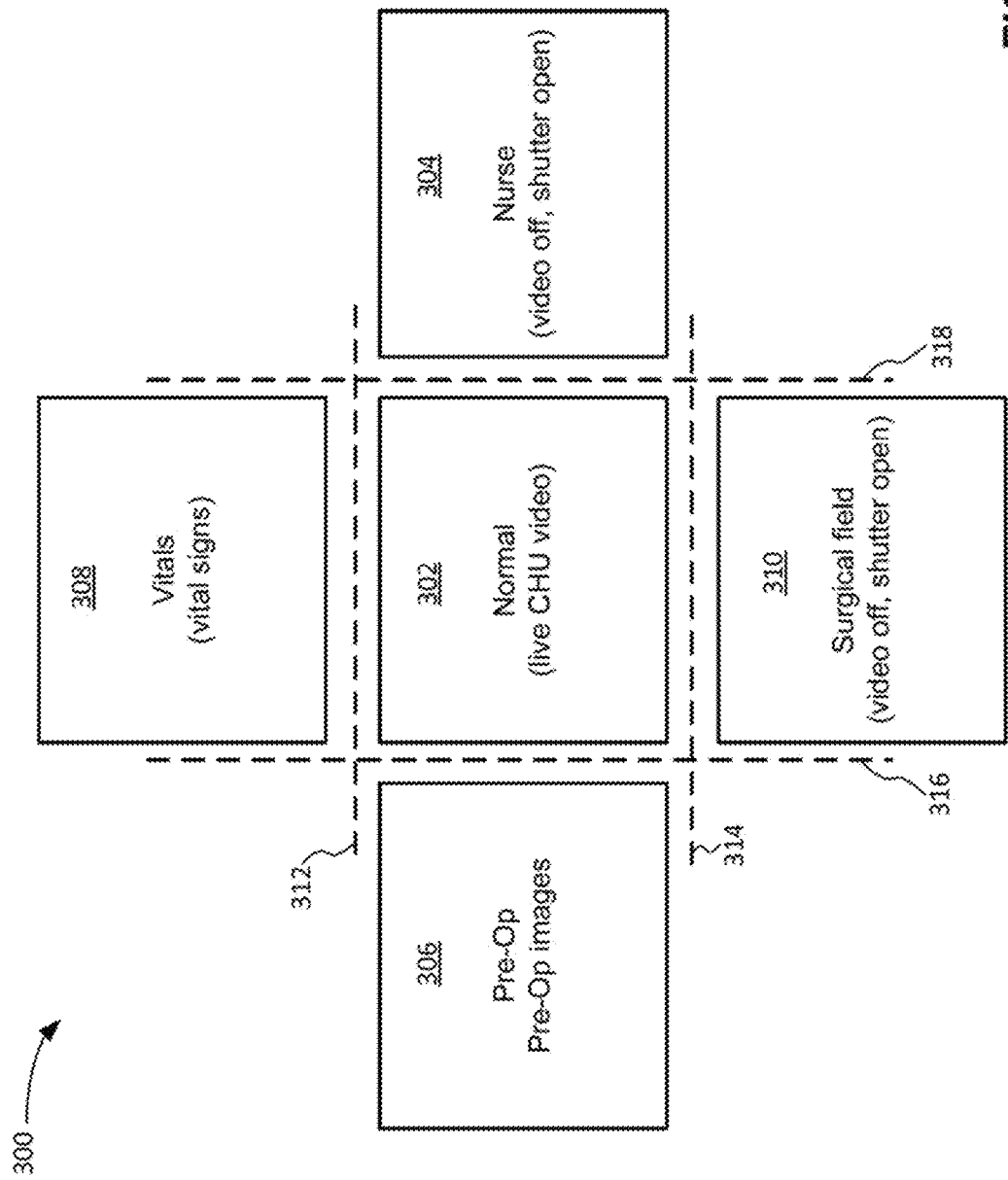
FIG. 3A illustrates an exemplary layout for multiple P&O regions respective of a HMD mapped to different system modes, constructed and operative in accordance with another embodiment of the disclosed technique.

Reference is now made to FIG. 3A which illustrates an exemplary layout 300 for various positions and orientations for HMD 102 (FIG. 1A) divided into multiple zones, constructed and operative in accordance with another embodiment of the disclosed technique. Layout 300 shows multiple zones respective of multiple orientation regions for HMD 102, each region corresponding to a different system mode. System 100 allows surgeon 120 to switch from one system mode to another by rotating his head, thereby rotating HMD 102. Surgeon 120 can customize the functionality of HMD 102 by defining multiple angular and positional zones respective of his range of head motion, and determine which system mode will be implemented respective of each zone.

Layout 300 shows zones 302, 304, 306, 308, and 310 respective of HMD 102 of FIG. 1A. Dashed lines 312, 314, 316, and 318 indicate angular thresholds between zones 302, 304, 306, 308, and 310 thereby defining the respective zones. Line 312 defines the threshold between Vitals zone 308 and Normal zone 302; line 314 defines the threshold between normal zone 302 and surgical field zone 310; line 314 defines the threshold between Normal zone 302 and Pre-op zone 306; and line 318 defines the threshold between Normal zone 302 and Nurse zone 304. Pressing a pedal of footswitch 104 while crossing one of thresholds 312, 314, 316, and 318 by changing the orientation of HMD 102 to align with a new zone switches to the system mode to correspond to the new zone.

Zone 302, labeled "Normal", associates a forward, level orientation for HMD 102 with the Normal system mode. When surgeon 120 presses on footswitch 104 while moving his head to align HMD 102 with zone 302, the Normal system mode is initiated. Shutter 132 is closed, and a live video feed of images acquired by camera head 110 is rendered via HMD 102.

Zone 304, labelled "Nurse" associates a right, level orientation for HMD 102 with the Nurse system mode. When surgeon 120 presses on footswitch 104 while moving his head to align HMD 102 with zone 304, the Nurse system mode is initiated. Shutter 132 opens and the video feed is turned off, allowing surgeon 120 to directly see and communicate with a nurse while wearing HMD 102.

Zone 306, labelled "Pre-op" associates a left, level orientation for the head of surgeon 120 with the Preoperative Data system mode. When surgeon 120 presses on footswitch 104 while moving his head to align HMD 102 with zone 306, the Preoperative Data system mode is initiated. Shutter 132 is kept closed, and preoperative data is displayed via HMD 102. In some embodiments, the UI functionality may change when switching to the Pre-op system mode. For example, menu items may differ and head gestures may cause different actions to be performed on system 100 than in other system modes, to allow the surgeon to browse and scroll within the preoperative data.

Zone 308, labelled "Vitals" associates a forward, upwards orientation for HMD 102 with the Vital Signs system mode. When surgeon 120 presses on footswitch 104 while moving his head to align HMD 102 with zone 308, the Vitals system mode is initiated, and data indicating one or more vital signs of patient 122 are displayed via HMD 102.

Zone 310, labelled "Surgical Field" associates a forward, downwards orientation for HMD 102 with the Surgical Field system mode. When surgeon 120 presses on footswitch 104 while moving his head to align HMD 102 with zone 310, shutter 132 is open and the display is turned off, allowing surgeon 120 to view a real world view of surgical field 124.

In some embodiments, the system mode is determined according to the current P&O of HMD 102 only while pressing footswitch 104 (e.g. a button in footswitch 104 predefined to trigger mode switching based on HMD P&O). Surgeon 120 switches the system mode for system 100 by moving his head to crossing one or more of angular thresholds 312, 314, 316, and 318 while pressing footswitch 104. Once the orientation of the head of surgeon 120 extends beyond a predefined angle such that HMD 102 is aligned with a new zone, the system mode switches to that corresponding to new zone. For example, to remain in the Pre-op mode, surgeon 120 maintains his gaze beyond angular threshold 316 (to the left) while pressing footswitch 104. When first pressing footswitch 104 the system mode immediately switches if the current HMD P&O is beyond a threshold of the current mode. In this embodiment, when the surgeon releases the footswitch 104 the system mode switches back to the original mode. This manner of mode operation is useful for instance if the user prefers fast glimpses at preoperative data or the nurse. In some embodiments, when the surgeon releases the footswitch 104 the system mode stays in the current mode, allowing the user to freely move the head again without affecting the system mode. This manner of mode operation is useful for instance if the user prefers to comfortably study preoperative data for an extended period of time.

Angular thresholds 312, 314, 316, and 318 may additionally allow for hysteresis-enabled control. For example, a larger threshold value might be effective when crossing the threshold from Normal zone 302 to Nurse zone 304, and a smaller angular threshold might be effective when crossing back from Nurse zone 304 to Normal zone 302. This is useful to avoid undesired mode switching when the head orientation is close to the angular threshold. The hysteresis state (enable/disable) and hysteresis size may be configured by surgeon 120. System 100 may automatically generate the two hysteresis-generating thresholds from a single threshold value.

In another embodiment, zones 302, 304, 306, 308 and 310 are not defined with exact threshold values. Rather, the activation of the modes associated with zones 302, 304, 306, 308 and 310 is based on relative head gestures by surgeon 120. For example, pressing pedal 104C of footswitch 104 while turning his head by more than 10 degrees to either direction switches to the system mode to correspond to the relative direction of rotation required to switch from the current system mode to other system modes.

In a further embodiment, input from footswitch 104 is not required for switching modes. Angular thresholds 312, 314, 316, and 318 are used as a trigger to change the system mode. The system mode corresponding to each of the regions is determined according to the current P&O of HMD 102. For example, to remain in the Pre-op mode, surgeon 120 is required to maintain his gaze beyond angular threshold 416 (to the left).

In yet another embodiment, "touching" the angular threshold by briefly turning the head toggles between the system modes corresponding to the respective zones. Once surgeon 120 "touches" angular threshold 316 while pressing on footswitch 104, the system switches from Normal mode to Pre-op mode, corresponding to Pre-op region 306. While in this mode, surgeon 120 can comfortably gaze ahead and view pre-operative data without straining his neck for a prolonged period of time. Touching threshold 316 a second time while pressing on footswitch 104 switches the system mode back to "Normal", corresponding to Normal region 302, allowing surgeon to view a live magnified image of surgical field 124 via HMD 102. Footswitch 104 is used for enabling the switch between system modes, so that only by pressing a specific pedal of footswitch 104 while simultaneously touching the threshold with a head gesture causes a switch to a new system mode. This is to avoid inadvertent mode switching.

Figure 3B:
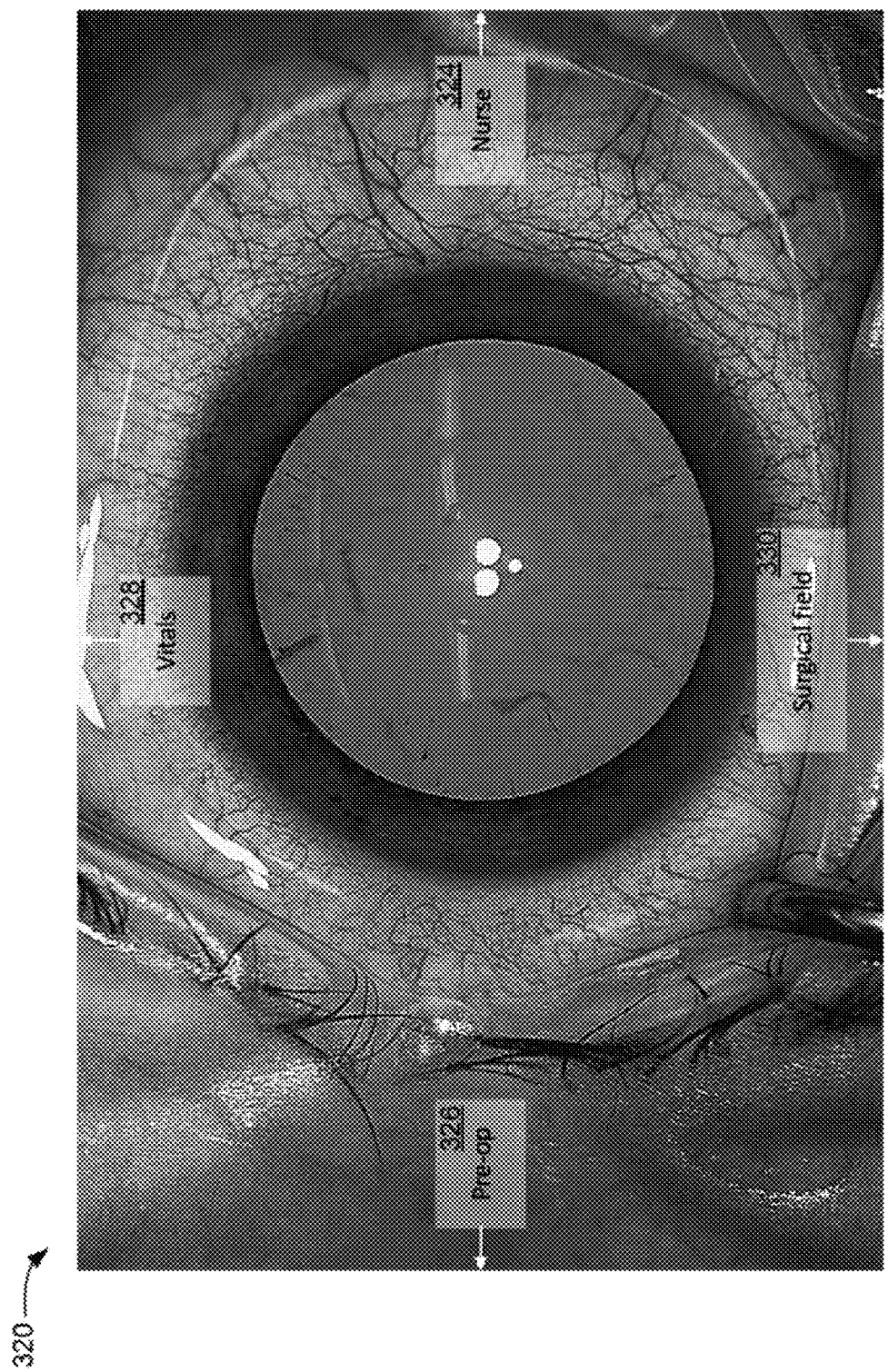
FIG. 3B illustrates a display of a live image overlaid with hints indicating which head gestures will invoke the system modes associated with the zones described with respect to FIG. 3A, constructed and operative in accordance with an embodiment of the disclosed technique.

Reference is now made to FIG. 3B which illustrates a display of a live image 320 overlaid with hints indicating to the user which head gestures are required to invoke the various system modes, associated with the zones described with respect to FIG. 3A, constructed and operative in accordance with an embodiment of the disclosed technique. Image 320 displayed over the field of view of HMD 102 corresponds to the Normal mode, associated with zone 302. In some embodiment, surgeon 120 may elect for system 100 to display features 324, 326, 328, and 330 that hint to surgeon 120 which head gesture will invoke which system mode. Features 324, 326, 328, and 330 are displayed transparent or translucent at the periphery of the field of view, so as not to obstruct the display of image 320. Feature 324 with the label "Nurse" hints to the surgeon that turning his head to the right in the direction of feature 324 invokes the Nurse mode, corresponding to zone 304 of FIG. 3A. Feature 326 with the label "Pre-op" hints to the surgeon that turning his head to the left in the direction of feature 326 invokes the Pre-op mode, corresponding to zone 306 of FIG. 3A. Feature 328 with the label "Vitals" hints to the surgeon that turning his head up in the direction of feature 328 invokes the Vitals mode, corresponding to zone 308 of FIG. 3A. Feature 330 with the label "Surgical Field" hints to the surgeon that turning his head down in the direction of feature 330 invokes the Surgical Field mode, corresponding to zone 310 of FIG. 3A. This feature may be useful when surgeon 120 is not yet familiar with the system, and may be switched on or off, as needed. Similarly, surgeon 120 can elect to freely enable the mode switching only through head gestures without using footswitch 104, or revert back to enablement via footswitch 104, according to context and need.

In one embodiment, features 324, 326, 328, and 330 are displayed only when surgeon 120 depresses footswitch 104 to enable mode-switching based on head gestures. Optionally, the display of features 324, 326, 328, and 330 may be a default setting. It is to be noted that the display of specific features 324, 326, 328, and 330 is exemplary only. In general, features are displayed in a manner corresponding to the current mode. Thus a different system mode will have different features displayed. For example, when system 100 is in the Pre-op mode, then only one feature is displayed overlaid on the image in the field of view, directing surgeon 120 to turn his head to the right to return to the Normal mode. In such a case, feature 324, currently indicating "Nurse" would indicate Normal, and features 326, 328, and 330 would not be displayed.

Surgeon 120 may define and configure a system mode, either from scratch or by duplicating an existing mode and modifying it using touchscreen 108. Once at least two system modes are defined, surgeon 120 may associate system modes with orientation regions by wearing HMD 102, gazing at the general direction where he desires the mode switch to be subsequently triggered, and selecting the modes that will be associated with each of the zones defined by the threshold. When modes are additionally defined by a location within the operating theater, surgeon 120 may physically move to the desired location that triggers the system mode switch. This is performed in a dedicated system mode, having special menus and gestures to support various system settings and configurations. This is optionally performed by each new user as an initial setup or configuration phase. The user may invoke and operate mode-designation independently via the HMD menu, or with the help of a second person operating a GUI on the touchscreen.

The default display state is the full-screen state. In this state, HMD 102 displays a full-screen display-stabilized image that appears fixed relative to surgeon 120. Content displayed via HMD 102 appears as a screen rigidly suspended from HMD 102. As surgeon 120 moves his head, the screen moves with him, appearing fixed relative to him. In addition to the full-screen state, system 100 provides the virtual screens state. Surgeon 120 can invoke the virtual screens state from the full-screen state. The virtual screens state may be invoked using any combination of the user-interface methods described above, such as by pressing pedal 104B of footswitch 104, use of head gestures or voice commands, and the like. The virtual screens state changes only the screen state, keeping all other system characteristics of the current mode (e.g. the display of the live image feed) unchanged.

In accordance with a further embodiment of the disclosed technique, switching between system modes is achieved through the virtual screens state. In the virtual screen state, content is displayed in one or more virtual screens that are world-stabilized, appearing fixed to the operating theatre. As surgeon 120 moves his head, the virtual screens move in and out of his field of view, allowing him to scroll through content displayed therein. Depending on the distance between surgeon 120 and the virtual locations for the virtual screens, surgeon 120 may see more than one virtual screen at a time. This is described in greater detail herein below, with respect to FIG. 5C.

To switch the system mode using the virtual screen state, each system mode may be indicated by a virtual screen that displays the content that surgeon 120 would see in full-screen state if that system mode were selected, functioning as a type of thumbnail. This allows surgeon 120 to simultaneously preview the content available in different system modes, without switching modes. The detail and resolution of content displayed on a virtual screen may differ from that displayed in the corresponding full screen state due to limitations to screen size, technical issues and bandwidth. For example, overlaid symbols appearing in full-screen state may not appear in the thumbnail image displayed in a virtual screen state. However, the images are substantially similar in both virtual screen and full screen states. Surgeon 120 may switch between system modes in the virtual screen state using any suitable UI input, such as by staring at a virtual screen for a predefined period of time, or with a head gesture combined with pressing on footswitch 104. Not all of the system modes are necessarily represented by the virtual screens, such as system modes with the display turned off.

Once a system mode is selected, the screen state automatically switches to full-screen state in the selected mode. Surgeon 120 may configure system 100 to remain in the virtual screen state after switching modes. In this case, all system characteristics other than the screen state change. In one embodiment, the virtual screens state is itself a system mode that allows surgeon 120 to view several virtual screens simultaneously. In this case all other system characteristics including user interface characteristics are uniquely defined for this system mode.

In some embodiments, systems modes may be switched via touchscreen 108. It may be desirable in some applications to allow a third party, such as a nurse, to switch to a different system mode. In this case, the nurse is provided with the touchscreen that is coupled to computer 118. Touchscreen 108 may be coated with sterile nylon for use in the operating theatre by any of the sterile surgeons present.

In some embodiments, system modes may be switched via voice commands or other acoustic commands, such as tongue clicks. Microphone 138 records one or more acoustic commands emitted by surgeon 120. Computer 118 analyzes the acoustic commands to determine various system functionalities, such as switching system modes. To avoid false activation, system 100 may be configured to respond only to acoustic commands that begin with an identifying sound, such as by calling out an identifying name for system 100. For example, surgeon 120 may switch to the Normal mode by calling out the identifying name for system 100 and commanding system 100 to switch to the Normal mode.

In accordance with another embodiment of the disclosed technique, a menu is displayed via HMD 102. Menus may be invoked by pressing on a pedal of footswitch 104, such as pedal 104B, or by other UI means such as voice control or a dedicated head gesture. Invoking a menu causes it to be overlaid on the content currently displayed via HMD 102, to allow navigating and choosing an item within the overlaid menu via head gestures. The menu may be displayed as a semi-transparent display-stabilized overlay on the current image displayed via HMD 102, or in a separate, virtual screen, and the like.

For example, in keeping with the concept illustrated in FIG. 3A, where different positions and orientations for HMD 102 correspond to different functionalities, one position and orientation may correspond to a menu display. When the surgeon wearing HMD 102 looks towards a pre-defined direction, e.g. downwards, the menu is displayed. In some embodiments, the menu may first be displayed in a compact or collapsed manner, so as to occupy less display-area. In other embodiments, the menu is displayed (collapsed or regular) away from the forward direction of HMD 102, such as orthogonal to the forward direction of HMD 102. The menu may open fully after the surgeon continues looking in the pre-defined direction for a predetermined time period. In some embodiments, the menu is not invoked when the surgeon is directing or orienting his head as part of a head gesture that is configured to enable other functionalities. Surgeon 120 navigates and controls the menus, displayed as HMD-stabilized overlays, via head gestures. In some embodiments, pressing footswitch 104 invokes a menu and allows the user to navigate and highlight the various menu items using head gestures, and releasing the footswitch causes the menu item to be activated. For example, to choose a menu item, surgeon 120 presses the applicable pedal on footswitch 104 and maneuvers his head to select a menu item. Releasing footswitch 104 activates the action corresponding to the selected menu item.

The menu may list any number of parameters, such as but not limited to the various system modes available for system 100. Each system mode is represented by a menu item that includes symbols or text, such as textual description of the system mode, e.g. "Normal", "Nurse", "Pre-op" and the like. Other menu options in addition to the system modes may be included in the menu. The additional menu options may be mode-specific, pertaining to the characteristics controllable in that system mode. For example in the Normal mode the menu may include an item that allows switching the flood illumination on and off, and a red-eye-illumination on and off. In the Pre-op mode, these options may not appear and instead the Pre-op menu may enable opening a folder containing available preoperative datasets and display a sub-menu for choosing which dataset to display. The Pre-op menu may additionally include items to control various attributes for displaying the preoperative data. Menu options may be mode-specific, procedure-specific and stage-specific, i.e. the menu appearance may change depending on the system mode and the stage in the procedure. In addition to switching between system modes the menu allows toggling between states.

In some embodiments, the menu is displayed at the margins of the display of HMD 102, so as not to block the live image displayed at the center of the display area provided by HMD 102. As surgeon 120 navigates through each menu item of a menu displayed at the margin, the functions of the menu item may be temporarily enabled to indicate to surgeon 120 where he is on the menu, and what is the effect of selecting that menu item. For example, on navigating over a menu item that highlights the color green to allow surgeon 120 view a membrane that has been injected with a green dye, that functionality may be temporarily enabled to indicate to surgeon 120 which menu item he is currently navigating over and what is the effect of selecting the menu item, while allowing him to maintain his focus on the live image. However, some menu items may relate to functions that are not immediately evident while gazing at the live image displayed via HMD 102. To allow surgeon 120 to keep his focus on the live image while tracking his navigation through the menu, a non-visual indicator, such as a sound or vibration, may be triggered when a new menu item is highlighted. This allows surgeon 120 to track his navigation through the menu without directly looking at it, so that he can maintain his focus on the live image.

In some embodiments, the menu on the right margin of the display is dedicated to applications. Examples of such applications include the preoperative OCT application, the teaching application, the pre-planning application, the phaco-vitrectomy settings and metrics application, the intra-operative OCT application and the like. For example, when pressing the footswitch menu button, the menu on the left margin of the display is the main menu, and the menu on the right margin of the display is dedicated to applications and allows to turn on an application by activating a corresponding menu item. Switching between the two branches of the menu (i.e. the menu on the left and right margins of the display) is done by turning the head left or right.

In another embodiment, once an application has been turned on, the next time the footswitch menu button is pressed, the menu that appears on the right margin is a dedicated menu for the activated application. For example, when the preoperative OCT application is activated, a PIP with a B-scan appears in the display, and a line indicating the location of the B-scan is overlaid on the live image. When the footswitch menu button is pressed, the menu that appears on the right margin is a dedicated menu for the preoperative OCT application in place of the general applications menu on the right margin of the display. Surgeon 120 may navigate and select menu items from the dedicated menu, such as to turn on and off the overlay of the line indicating the B-scan location on the live image, to switch to another screen where a different set of OCT scans may be chosen for display in PIP, to turn off the preoperative OCT application, and the like. Once the preoperative OCT application is closed, the next time the footswitch menu button is pressed, the general applications menu appears on the right margin of the display. It is to be noted that these examples are only given to illustrate the range of features of system 100 that can be controlled via UI 160.

In a further embodiment, the same footswitch button that is used to invoke and operate the menu may also enable switching screens by simultaneously turning the head while pressing the footswitch button. For example, when pressing the footswitch menu button and slightly turning the head to the right, the first menu item in the menu branch appearing on the right margin of the display is highlighted. Turning the head further to the right may invoke switching the screen.

The following example is given for procedure-specific and stage-specific menu options. During a cataract procedure, an external machine (not shown) may be connected to system 100. The external machine injects data for displaying as an overlay on the live magnified video rendered on display module 130. When system 100 identifies that the external machine is connected, display module 130 displays a menu option for toggling between 'enable' and 'disable' states of "external data overlay" and "rhexis guidance". When system 100 identifies, based on the injected data, that a procedural stage, such as the phacoemulsification stage, is complete, display module 130 displays a menu option to toggle between 'enable' and 'disable' states of "IOL alignment guidance" instead of the "rhexis guidance".

Menus may be used to control features and aspects of system 100, including selecting and switching to a new system mode, and returning to a previous system mode. Since accessing system modes only according to P&O zones may limit the number of available system modes to the number of zones in the field of view, menus may allow increasing the number of available system modes. Thus, one system mode may be a menu mode presenting menu items for choosing other system modes, as well as items for controlling additional system features and parameters. While in the menu mode the menu for the system modes may be displayed via HMD 102, with the UI functionality mode-specific, i.e. certain gestures and motions by surgeon 120 cause one functionality while in the menu mode, and a different functionality in a different system mode. The menu mode may be invoked using any suitable UI interface, such as by performing one or more of: pressing pedal 104C on footswitch 104, by emitting a voice command recorded by microphone 138, performing a head gesture, eye motion, and the like.

Figure 4A:
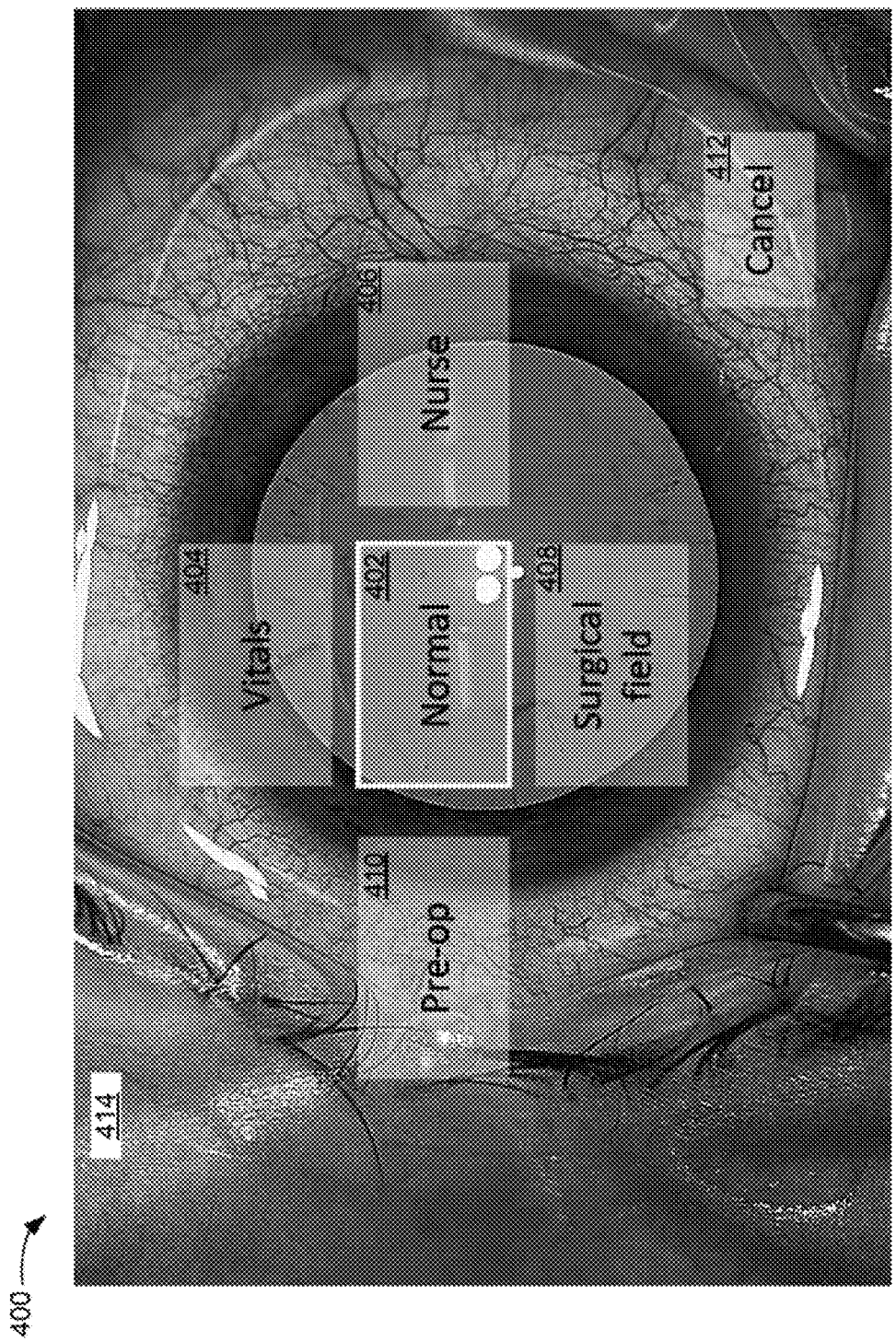
FIGS. 4A-4C, taken together, illustrate a menu for switching to different system modes overlaid on a video displayed via the HMD, constructed and operative in accordance with a further embodiment of the disclosed technique.
Figure 4B:
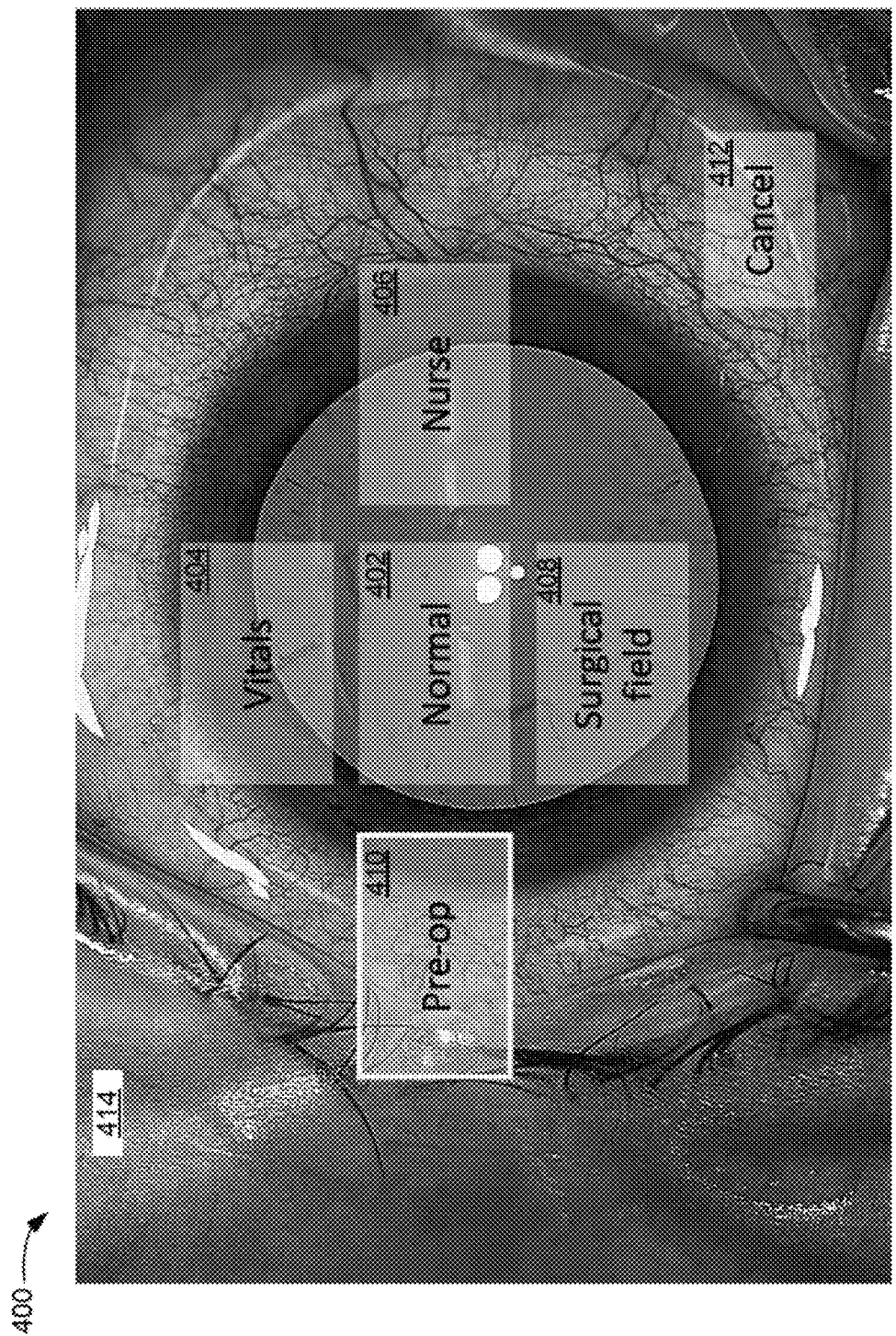
Figure 4C:
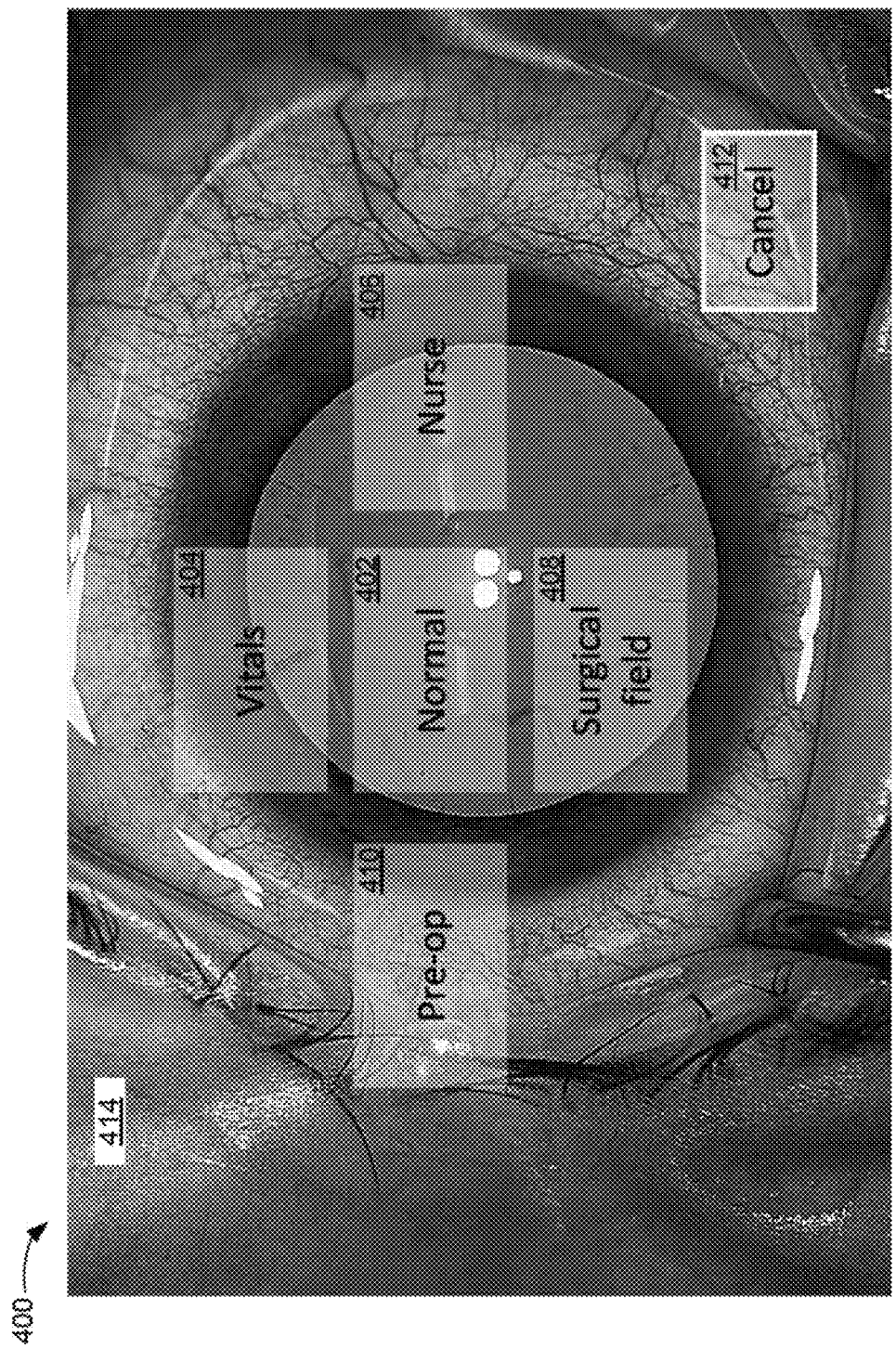

Reference is made to FIGS. 4A-4C, which together illustrate an exemplary system mode menu 400 overlaid on the display of a magnified image 414, constructed and operative in accordance with a further embodiment of the disclosed technique. The exact implementation details described below are intended as exemplary and do not limit the invention. System mode menu 400 allows surgeon 120 to switch between system modes while still viewing live image stream 414. System mode menu 400 appears similar to the layout of the zones of FIG. 3A, however this is not a requirement. Surgeon 120 views a live magnified image stream 414 of surgical field 124 via HMD 102 (FIG. 1A) configured in the full screen state. Surgeon 120 performs a predefined foot gesture, such as pressing on pedal 104B of footswitch 104. In response, computer 118 displays system mode menu 400 overlaid on magnified image stream 414. The menu items of system mode menu 400 are transparently overlaid on the magnified image stream 414 such as not to obstruct the displayed images.

In the exemplary implementation shown, system mode menu 400 includes menu items 402 (Normal), 404 (Vitals), 406 (Nurse), 408 (Surgical Field), 410 (Pre-op), and 412 (Cancel). Since the current system mode is Normal, element 402 is highlighted (FIG. 4A). In some embodiments, the menu items are spatially arranged according to their functionality. For example, in operating theatres where the nurse sits to the right relative to surgical field 124, menu item 406 (Nurse mode) is displayed on the right side of the field of view of HMD 102, whereas menu item 402 (Normal mode) is displayed in the center of the field of view. To navigate system mode menu 400, surgeon 120 turns his head while still pressing on pedal 104B of footswitch 104.

Referring to FIG. 4B, surgeon 120 turns his head to the left, crossing an angular threshold separating menu items 402 and 410. The highlight switches from menu item 402 to menu item 410 (Pre-op mode). In one embodiment, only the highlight has switched to the Pre-op mode menu item 410. The system mode has not yet been switched. Only once surgeon 120 lifts his foot from footswitch 104 to release pedal 104B, does the system mode switch to the mode corresponding to selected menu item 410, e.g. the Pre-op mode (FIG. 4B). In another embodiment, when the highlighted menu item is switched, the background image also changes as though the system mode were switched, thus allowing the user to see a preview of the image associated with the menu item.

Referring to FIG. 4C, surgeon 120 turns his head towards the bottom right corner while still pressing on pedal 104B. Once his head angle has crossed an angular threshold set for menu item 412, corresponding to the cancel selection, the highlight switches to menu item 412 (Cancel). Surgeon 120 selects menu item 412 by releasing pedal 104B of footswitch, to hide menu 400 without changing the system mode, cancelling the action of bringing up menu 400 through pressing pedal 104B. In this manner, surgeon 120 cancels system mode menu 400, and system 100 remains in the current system mode.

In this embodiment, the screen state is display stabilized. As the surgeon moves his head, image 414 remains fixed in his field of view, irrespective of his head motion. However the highlight for the selected menu items of menu 400 overlaid on the stabilized image 414 shifts with his head movements.

The selected menu item may be highlighted in various ways, such as by displaying it with a different font, background color, displaying a cursor pointing to it, or any other suitable technique to differentiate it from the other non-selected menu items. The highlighting moves from one menu item to a neighboring menu item when HMD 102 is rotated towards the second menu item while footswitch 104 is depressed. This is indicated in FIG. 4B. When the surgeon turns his head to the left, menu item 410, corresponding to Pre-op mode is selected and indicated with highlight, and menu item 410 correspond to Normal is de-selected and displayed regularly. Surgeon 120 can personalize the response of system 100 to his head gestures. For example, head motions can be scaled such that a minor head tilt translates to a correspondingly larger angular shift in the highlighting, or the reverse. Alternatively, the orientation of HMD 102 controls a cursor (not shown) displayed on menu 400 that selects the menu items. Maneuvering the orientation of HMD 102 maneuvers the cursor, e.g. up-down and left-right head motions move the cursor up-down and left-right accordingly. Releasing footswitch 104 activates the system mode corresponding to the currently selected menu item, thereby switching the system mode.

In another embodiment, eye tracking may be implemented to control menu 400. The eye motion plays the role of the head motion above. Staring at a menu item may highlight the menu item, and continuous staring for more than a predefined period of time may activate the menu item.

Additional menus may be displayed via HMD 102 to select other functionalities, other than system modes. Some menu items may be expanded to display one or more sub-menus when selected. The selection method can be implemented by either pressing or releasing one of the pedals of footswitch 104, by keeping a menu item highlighted for more than a predefined period of time, by using a voice command detected by microphone 138, or by other suitable UI methods. When expanded into a sub-menu, the sub-menu may replace the original menu, or may be displayed alongside the original menu. The menu may also include standard menu-operation items such as back/return and exit/cancel.

Some menu items may be toggled on and off via UI 160. Toggle items are menu options that switch between two states, where the menu option currently displayed represents the state that is currently not active. For example, when shutter 132 is closed, the menu option for controlling the shutter will appear "open shutter" and vice versa. Examples of toggle items in the menu are given below:

Basic HMD system operation controllable via the menu:
Display (on/off). This shuts the display on or off. When the display is turned off no image is displayed, but the menu can still be invoked (i.e. displayed) to allow the user to turn the display back on. Controlling the display state is useful in VGS procedures in which the HMD is transparent (i.e. if the HMD comprises a shutter then it is open at this stage). In these procedures the user may wish to turn off the display in stages of the procedure that do not require guidance by the HMD, so the image does not distract him when viewing the surgical field.
Full-screen/virtual screens. In the full screen state, only one screen fills the FOV, whereas in the virtual screen state, multiple virtual screens are displayed. The screen state is further described below in relation to FIGS. 5A-5C.
Shutter (open/close). This controls the state of shutter 132. Shutter 132 may also be partially open or closed such as when displaying a feature overlaid on the real world view when the screen is mostly transparent.
Red-eye illumination (on/off).
Recording (on/off). This controls a feature of system 100 allowing surgeon 120 to record portions of the surgical procedure that can then be recalled at a later stage.
Advanced HMD operation (enable/disable) one or more of:
Auto-focus,
Auto-centering,
Auto-zooming.
HMD display parameters (on/off)
PIP on/off toggle for each predefined PIP that is displayed,
External data overlay to display externally acquired data via HMD 102.
Various procedure-specific, and stage-specific overlay symbols, images, and models
Designating pointer/cursor.
iOCT (on/off). This controls the OCT imaging.

In some embodiments, in addition to the mode-specific menus, UI 160 displays a specific menu dedicated to controlling the different functionalities of system 100. For example, UI 160 displays a different, dedicated menu for controlling each of the zoom, focus, illumination, and other functionalities. Each dedicated menu allows surgeon 120 to access options that are only relevant to a specific functionality. For example, the menu dedicated to the focus functionality allows surgeon 120 to select between various auto-focus settings.

In some embodiments, surgeon 120 accesses a menu dedicated to a specific functionality via the main menu. In other embodiments, surgeon 120 accesses a menu dedicated to a specific functionality directly, such as by double pressing on a button of footswitch 104 to activate the menu. For example, surgeon 120 may open the menu dedicated to the illumination functionality by performing two short presses followed by a long press on the button of footswitch 104 that enables head gestures to control the illumination. Surgeon 120 may navigate the dedicated menu as described herein, using head gestures or eye tracking, and activate a highlighted menu option by releasing the button of footswitch 104.

In some embodiments, surgeon 120 opens the dedicated menu by pressing the relevant button of footswitch 104 only partially (e.g. a half-way press), or by issuing a voice command while pressing on footswitch 104, or by performing a head gesture, such as a nod while pressing on footswitch 104. For example, a "yes" head gesture may control the enabled functionality (e.g. focus, zoom, illumination, and the like), and a "no" head gesture may open a dedicated menu.

For example, if surgeon 120 turns his head to the left or right while pressing the footswitch button for enabling the focus functionality, a dedicated menu appears on the display for controlling the focus functionality, such as the auto-focus features. Through this dedicated menu, surgeon 120 can choose whether the auto-focus will work on a designated point, a surgical tool, and the like, and whether the auto-focusing is one-time or continuous.

In some embodiments, while enabling an action via footswitch 104, surgeon performs a "yes" motion (i.e. by moving his head up and down) to control a continuous (i.e. smooth) action, whereas performing a left or right turning motion will activate or toggle two discrete actions associated with the enabled action. Alternatively, a head gesture turning left may toggle a discrete action and a head gesture turning right may open a dedicated menu (or vice versa).

For example, while enabling "illumination", an up-down head gesture changes the illumination intensity, whereas a "turning left" head gestures will toggle the illumination between two discrete levels. For example one level may be "high" and the other "low". Optionally, these levels are pre-determined and can be configured by the user. Optionally after the surgeon adjusts the illumination levels during surgery, system 100 remembers the illumination levels and restores the same illumination levels the next time the illumination action is toggled (i.e., from high to low, or vice versa). To continue the example, a "right" gesture will toggle the illumination between the "on" and "off" states.

Figure 4D:
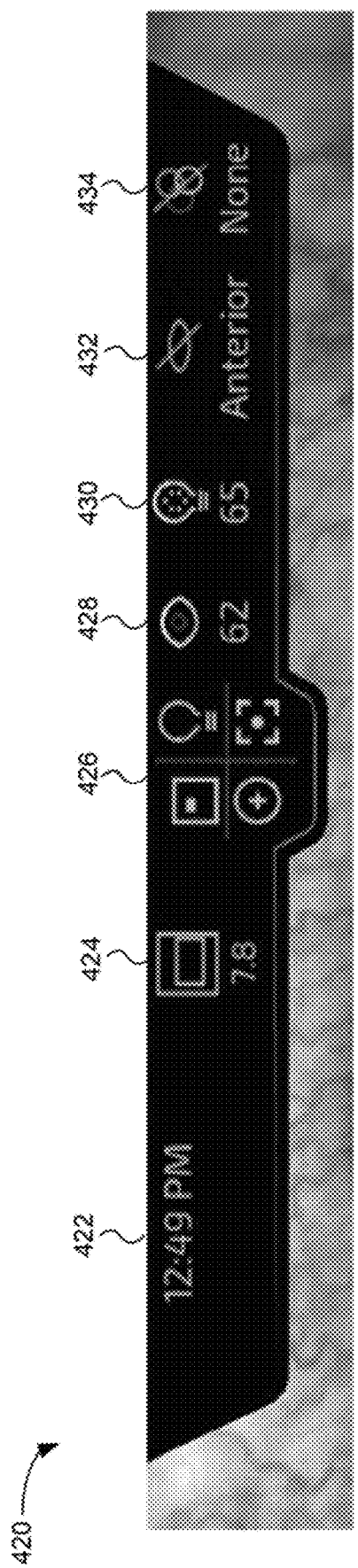
FIGS. 4D-4G illustrate implementations for displaying one or more status bars indicating system settings, constructed and operative in accordance with an embodiment of the disclosed technique.

As another example, while enabling "focus", a left head gesture may toggle between "on" and "off" for the autofocus functionality, and a right gesture may open a dedicated menu for controlling the focus functionality. Reference is now made to FIGS. 4D-4G, which illustrate implementations for displaying one or more status bars indicating system setting, constructed and operative in accordance with an embodiment of the disclosed technique. The illustrations of FIGS. 4D-4G are intended to be exemplary only, and other system indicators may be added, or may replace the indicators shown in FIG. 4D. Referring to FIG. 4D, a status bar 420 includes multiple different symbols indicating the current configuration for various settings for system 100. Status bar 420 is displayed via HMD 102, such as in response to an input by surgeon 120 via UI 160. Status bar 420 includes a clock 422, a ROI indicator 424, a footswitch indicator 426, an illumination indicators 428 and 430 a system mode indicator 432, and a color correction indicator 434. Clock 422 displays the current time. ROI indicator 424 indicates the displayed ROI relative to the entire ROI. In FIG. 4D, ROI indicator 424 displayed a smaller rectangle indicating the displayed ROI, positioned within a larger rectangle, indicating the entire ROI, such as may occur when surgeon 120 uses the zooming in feature to view a magnified portion of the live image. A number is displayed indicating the current magnification level. Footswitch indicator 426 indicates the available functions of footswitch 104. In the example shown, the available functions are indicated by four icons. Moving in a clockwise direction, the icon in the top left corner indicates the scroll of the XY motors, the icon in the top right corner indicates illumination, the icon in the bottom right corner indicates the focus, and the icon in the bottom left corner indicates the zoom. In some embodiments, the icon indicating the currently active function of footswitch 104 is highlighted. Illumination indicator 428 indicates that the red eye illumination is set to 'on', and the level is 62. Illumination indicator 430 indicates that the flood illumination is set to 'on' and the level is 65. System mode indicator 432 displays the current system mode, in this example it is anterior mode. Color correction indicator 434 displays the type of color correction applied to the images, in this example there is no color correction. Status bar 420 may be displayed at any suitable location via HMD 102, such as at the top of the display, or at any other location set by surgeon 120, and at any depth, as it is displayed to both eyes and the depth can be set. In some embodiments, status bar 420 is only displayed when a parameter is changed. Status bar 420 may indicate additional system features, such as the depth of field, digital gains, and other suitable parameters such as patient data, including name, age, gender, name of surgeon, or surgeons), date, location, the name of the hospital or clinic, and on the like.

Figure 4E:
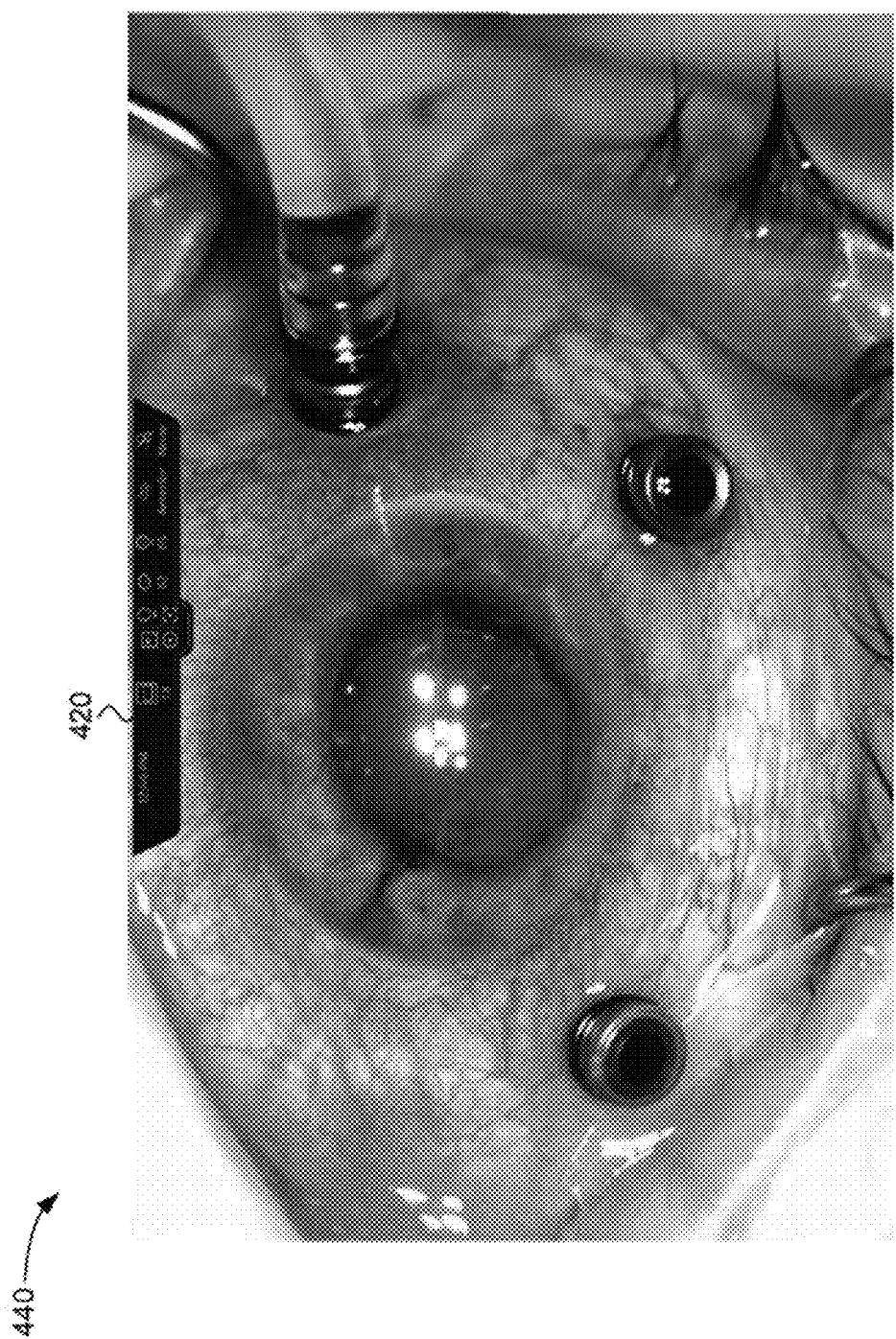

Reference is now made to FIG. 4E which shows a live image of the eye of a patient undergoing a surgical procedure, with status bar 420 overlaid on top, indicating the current system configuration to surgeon 120.

Figure 4F:
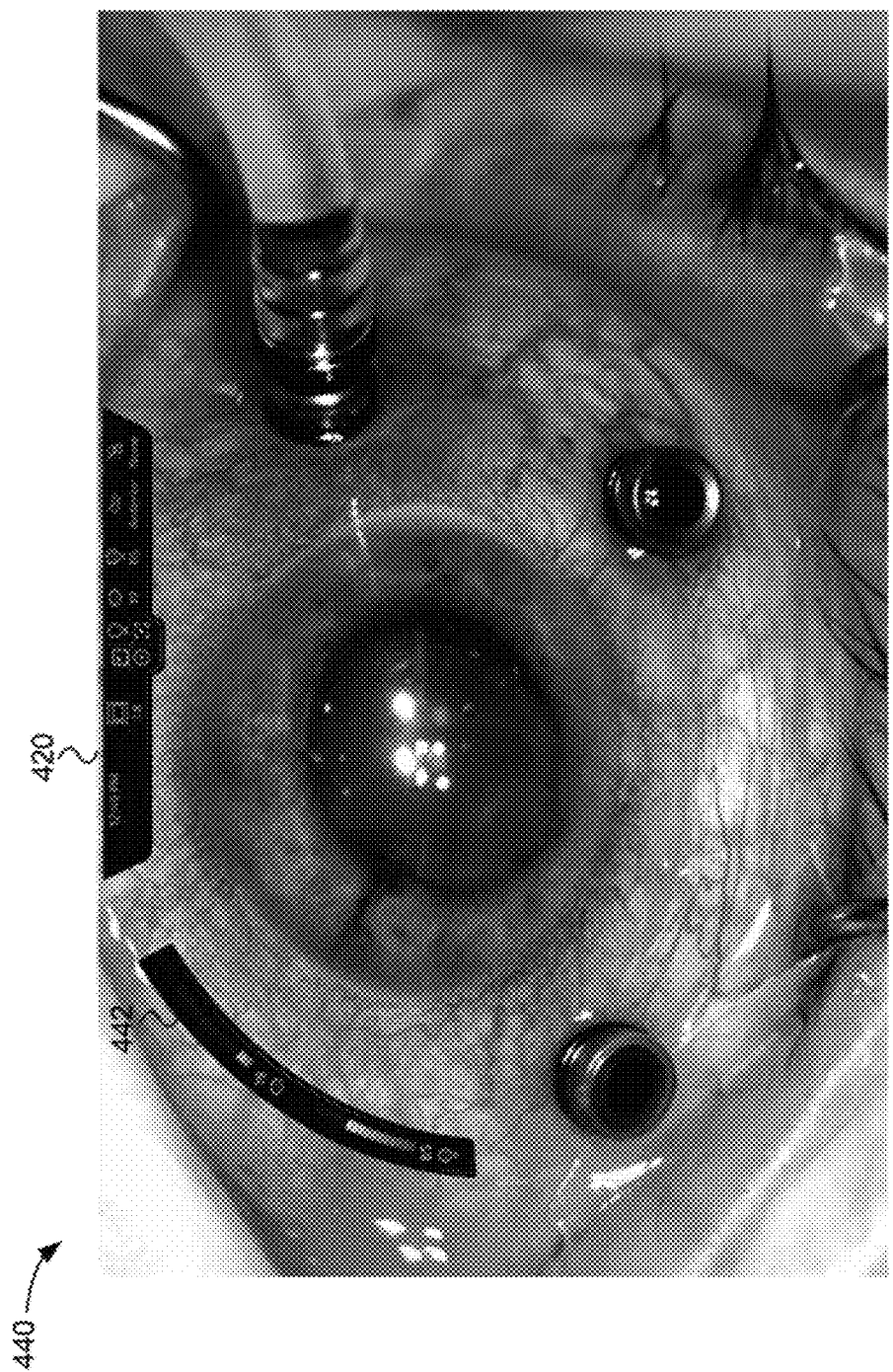

Reference is now made to FIG. 4F which shows the live image of FIG. 4E, with a second status bar 442 overlaid on top, in addition to status bar 420. In this exemplary implementation, status bar 442 is an arc that indicates the latest changes to the illumination settings. Status bar 442 is displayed in response to changes made to the illumination, to update surgeon 120 on the current configuration for system 100.

Figure 4G:
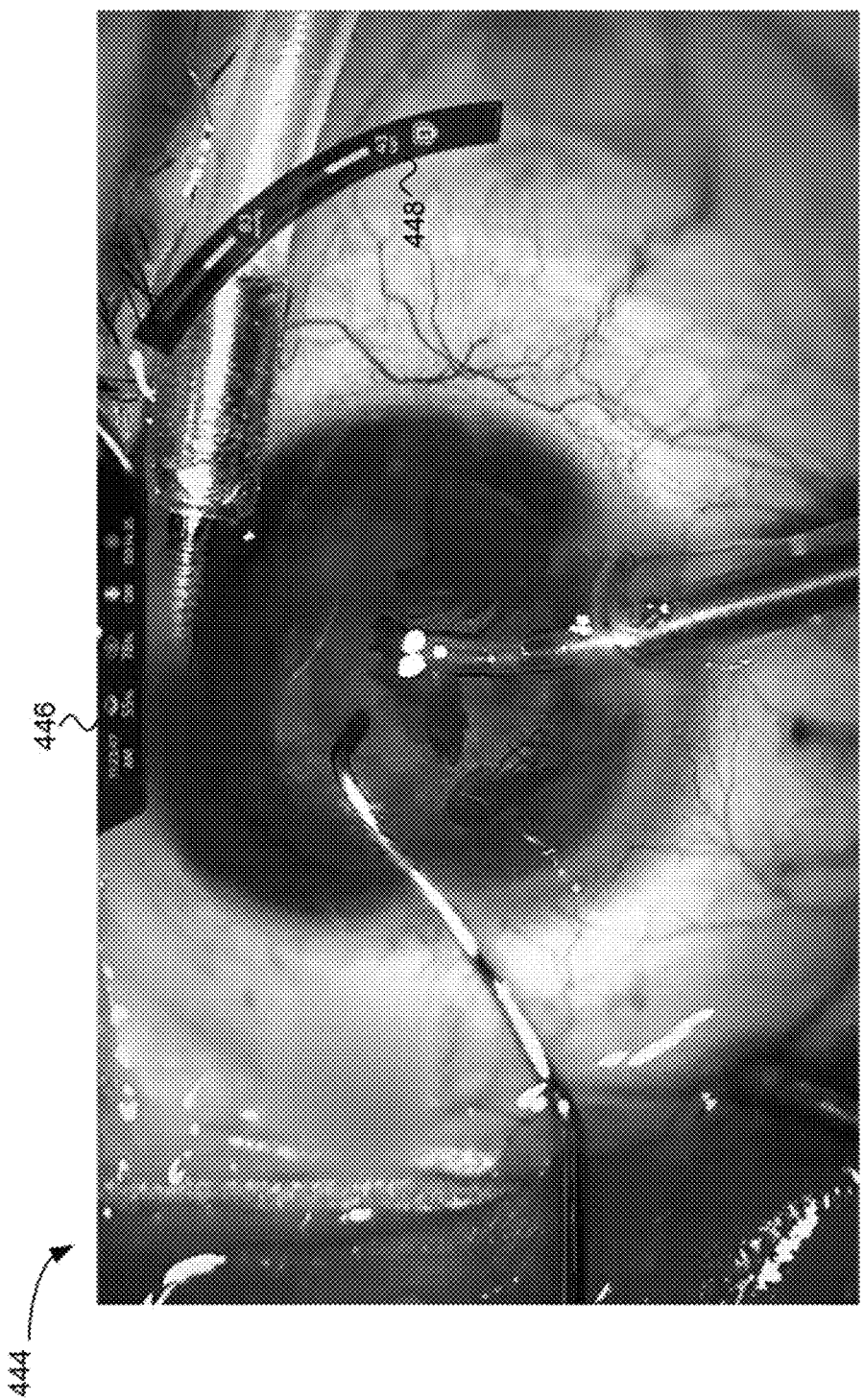

Reference is now made to FIG. 4G which shows another live image 444 of the eye of a patient undergoing a surgical procedure. A status bar 446 and a status bar 448 are displayed on live image 444. Status bar 446 is configured differently that status bar 420 of FIG. 4E. Status bar 448 appears when an external device is connected to system 100, such as a phaco-vitrectomy machine, and displays system settings corresponding to the external device. In some embodiments, the user may configure system 100 to either continuously display status bar 420 or hide status bar 420 in response to a user input or mode change. In some embodiments the default setting is to display status bar 420 continuously. In some embodiments, systems 100 provides multiple different status bars (not shown), in addition to status bar 420. Each status bar may be configured differently, where one or more status bars are configured to be displayed continually, and one or more status bars are displayed in response to any of a parameter change, in response to a user input, in response to detecting an external device, and the like.

In some embodiments, system 100 may issue a reminder or warning when the phaco probe is not centered in the capsular bag. In some embodiments, system 100 may issue a reminder or warning depending on a selected surgical technique, for example, if the chopper is not positioned under the phaco probe. System 100 may automatically stop the suction of a surgical instrument if the posterior capsule is sucked towards the phaco, as may be detected for instance via image processing. System 100 may track the surgical tools used by surgeon 120 to calculate the distance between the anatomy of patient 120 and the tools using any of: processing of images of the surgical procedure, analyzing iOCT data, analyzing a preoperative or intraoperative model of eye, and the like.

In some embodiments, system 100 may track one or more surgical tools, such as by applying image processing techniques to the live image, applying image processing techniques to intraoperative OCT data (iOCT). System 100 may have, a dedicated tool tracking subsystem based on optical tracking, or electro-magnetic tracking, and the like. Optionally, the tool tracking subsystem is also based on preoperative or intraoperative models of the eye.

The tool tracking function may be used for various features. For example, the tool tracking allows a user to use a surgical tool that would be used during the surgical procedure as an electronic pen. This may be useful in the teaching mode, where a supervising surgeon can make markings on the live image to guide the operative surgeon. UI 160 allows surgeon 120 to switch the drawing feature on or off, such as via voice command, footswitch 104, and the like. Alternatively, a physical tool can be paired to system 100 and used to press a virtual button, or select a menu item displayed via HMD 102, for example, select an item from a menu displayed in the retina periphery in posterior procedures, or in the eye periphery in anterior procedures, or displayed elsewhere in the operating room.

The tool tracking function may be used to detect and indicate the distance between the tip of the tool and the patient, e.g. the retina for eye surgery. The tool tracking function may be used to initiate automatic safety measures, such as automatically stopping the phaco suction. The tool tracking function may be used to guide surgeon 120 during a procedure. These examples are intended as exemplary only, and do not limit this function to the specific examples given.

A description of system characteristic controllable via user interface 160 now follows. It is to be noted that some system characteristics are controlled indirectly by the user when switching modes. For example, switching to a different mode may change the positioning of camera head 110, or the activation of a camera, or illuminator. The user may not be able to adjust these setting directly, but only indirectly by switching system modes, and other settings internal to system 100. This list is not intended to be limiting. Each system mode is characterized by two or more of the following system characteristics:

The display state (on/off);
The screen state (display/world stabilized);
The shutter state (open/closed);
The selection of displayed content (live image/pre-operative/other);
The illumination state;
Color correction schemes;
Image enhancement schemes;
Eye inversion state;
Motor velocity state;
Motor boundaries state;
Display of picture-in-picture (PIP) (on/off);
User interface settings;
Display overlay; and
iOCT settings.

The display state for HMD 102 can be set to 'on' or 'off', where the default display state for module 130 is 'on'. When the display is turned off, computer 118 halts the image sources for display modules 130A and 130B. Alternatively, computer 118 streams black images to HMD 102.

The screen state for HMD 102 defines how images and content are displayed to surgeon 120. There are two screen states for HMD 102: the full-screen display-stabilized state and the virtual-screens, world-stabilized state. In the full-screen display-stabilized state, the image appears to surgeon 120 as displayed on a screen rigidly suspended from HMD 102, and the displayed image moves with surgeon 120, remaining fixed. This is the default state. In the world-stabilized state, one or more virtual screens are displayed as though fixed to the operating theater. As surgeon 120 moves his head, the displayed content changes, as portions of the displayed content enter and exit the FOV of HMD 102.

Reference is now made to FIG. 5A which illustrates projected images as perceived by surgeon 120 when display module 130 is in a display-stabilized state, constructed and operative in accordance with another embodiment of the disclosed technique. FIG. 5A shows images 500 and 502 displayed in the full-screen, display-stabilized state. The field of view for HMD 102 is filled with a live magnified image acquired via camera system 112, and is displayed as though fixed to the head of surgeon 120. Elements 512 and 514 indicate the orientation of the head of surgeon 120. The dashed arrows of elements 512 and 514 indicate a front-facing orientation. The solid line arrow of element 512, respective of image 500, indicates that the orientation of surgeon 120 is 5° to the right of the front-facing orientation. The solid line arrow of element 514, respective of image 502, indicates that the orientation of surgeon 120 is 25° to the right of the front-facing orientation. Moving his head to change the orientation does not change the image appearing in his field of view, as though the screen were fixed to his head, and moves with him as he performs head gestures.

Figure 5C:
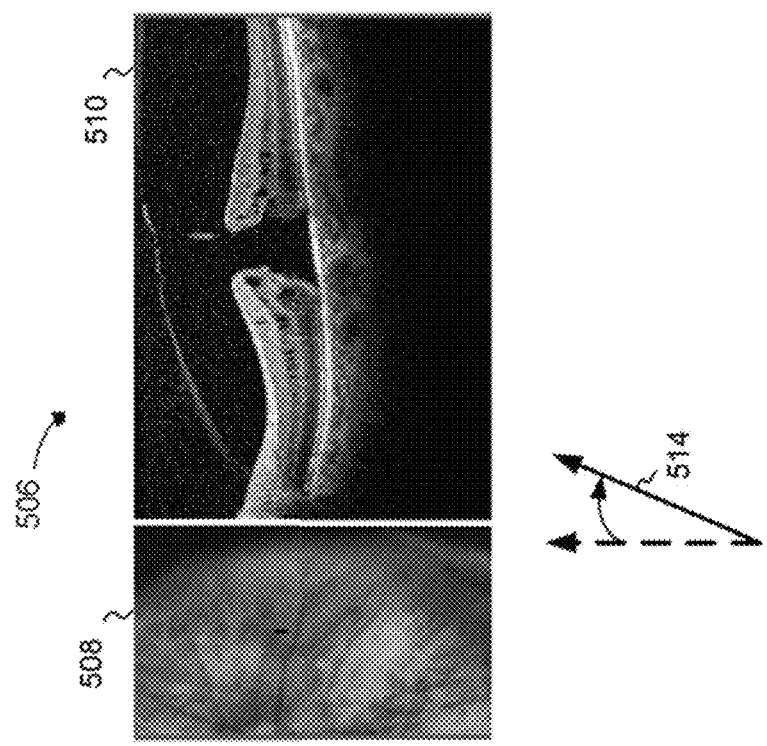
FIGS. 5B-5C, taken together, illustrate two views that are displayed via the HMD in the virtual-screens, world-stabilized state, respectively, each view corresponding to a different position and orientation of the head of surgeon, constructed and operative in accordance with a further embodiment of the disclosed technique.
Figure 5B:
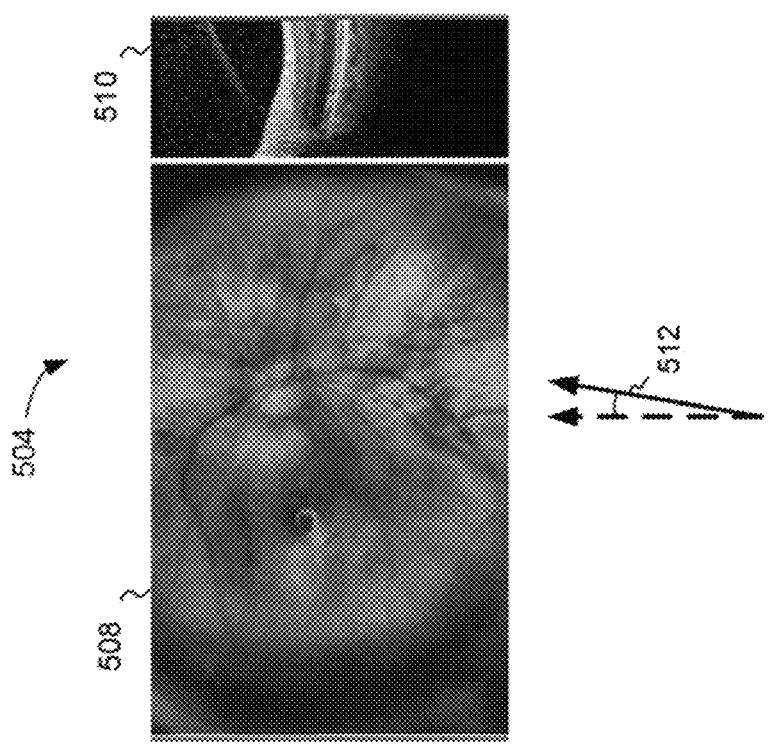

Reference is now made to FIGS. 5B-5C, which taken together, illustrate two views 504 and 506, respectively, that are displayed via HMD 102 in the virtual-screens, world-stabilized state, each view corresponding to a different position and orientation of the head of surgeon 120, constructed and operative in accordance with a further embodiment of the disclosed technique. In the views shown in FIGS. 5B-5C, two adjacent virtual screens 508 and 510 are displayed having the same (virtual) size and from the same distance from surgeon 120. In other embodiments multiple virtual screens having various (virtual) sizes, locations and distances may be used. Surgeon 120 sees images displayed via both of world-stabilized virtual screens 508 and 510, simultaneously. Virtual screen 508 displays a live video of the surgical field, and virtual screen 510 displays pre-operative data.

Views 504 and 506 each include the live image feed displayed via virtual screen 508, and corresponding pre-operative data displayed via virtual screen 510. Virtual screens 504 and 506 appear as though they are monitors positioned in a fixed location in the operating room (OR). As in FIG. 5A, elements 512 and 514 of FIGS. 5B-5C, respectively, indicate the orientation of the head of surgeon 120. The dashed arrows of elements 512 and 514 indicate a front-facing orientation. The solid line arrow of element 512, respective of view 504 (FIG. 5B), indicates that the orientation of surgeon 120 is 5° to the right of the front-facing orientation. The solid line arrow of element 514, respective of view 506 (FIG. 5C), indicates that the orientation of surgeon 120 is 25° to the right of the front-facing orientation.

As can be seen, view 506 of FIG. 5C appears as though shifted to the left relative to view 504 of FIG. 5B, corresponding to the rightwards head motion of surgeon 120. Virtual screen 508 in view 506 (FIG. 5B) shows less of the live video than virtual screen 508 in view 504 (FIG. 5C), and virtual screen 510 in view 506 (FIG. 5C) shows more of the pre-operative data than virtual screen 510 in view 504 (FIG. 5B). By moving his head left and right, surgeon 120 scrolls through the data displayed simultaneously in virtual screens 508 and 510, allowing him to view more or less within each, as required. The implementation of accurate world stabilized screens may be implemented with a 6 degrees-of-freedom (DOF) head gesture tracker comprising tracking components 134 for implementing full position and orientation tracking. In some embodiments, the virtual screens mode may be implemented using a 3-DOF tracker supporting head orientation alone, such as when an absolute position of the screens is not required.

Figure 5D:
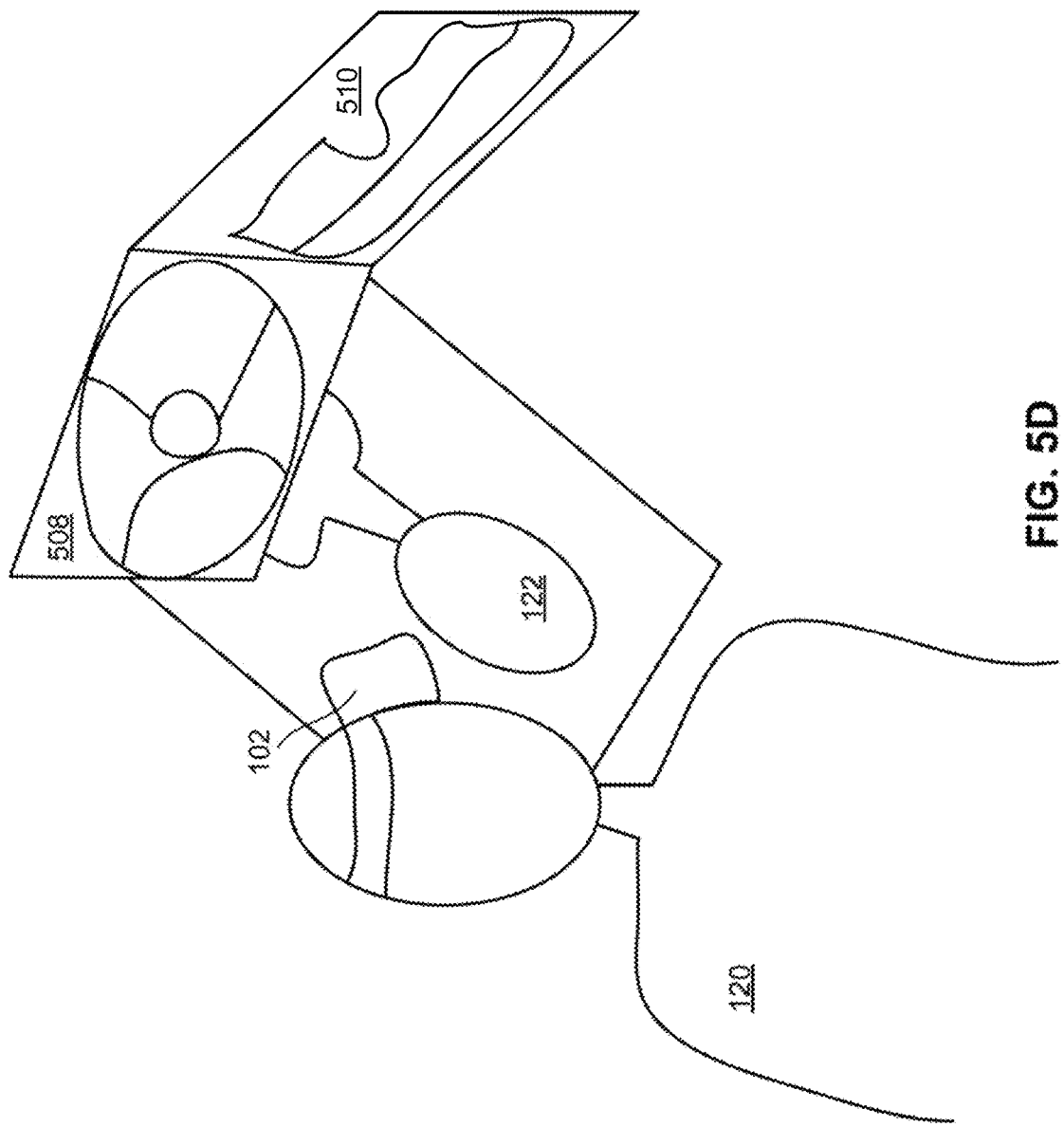
FIG. 5D illustrates an exemplary implementation of the Virtual screens state, as seen by the surgeon, constructed and operative in accordance with another embodiment of the disclosed technique.

Reference is now made to FIG. 5D which illustrates an exemplary implementation of the Virtual screens state, constructed and operative in accordance with another embodiment of the disclosed technique. Surgeon 120 of FIG. 1A wears HMD 102 and observes the two virtual screens 508, and 510 of FIGS. 5B-5C while operating on patient 122. Virtual screen 508 displays the live image feed acquired by cameras 140A and 140B (FIG. 1E), and virtual screen 510 projects pre-operative data, appearing as though displayed on another monitor positioned in the operating theatre. The content displayed via HMD 102 may be determined by the system modes. Options for displayed content may include: the live image stream acquired via camera system 112 (default); and pre-operative data (e.g. medical imageries and/or data related to the patient); Intraoperative data (i.e. data from other devices such as a phacovitrectomy system); a live image stream provided from an endoscope camera (not shown). In some embodiments, the options additionally provide for viewing a live image stream acquired from a similar system in an adjacent operating room, allowing surgeon 120 to follow the progress of a parallel operation; a live image stream provided from a Wi-Fi camera positioned in the waiting room, browsing a cloud-based library of images and videos, for reference during the surgery, and the like. The video acquired by cameras 140A and 140B and projected via HMD 102 is 3D. Each eye of surgeon 120 sees the video feed from the corresponding camera. Other videos and images display via HMD 102 may be either 2D or 3D. For instance, a video from a cloud-based library may be 3D, and pre-op images may be 2D.

The shutter state for shutter 132 of HMD 102 (FIG. 1C) may be open or closed, where the default state in microsurgery procedures is closed. When shutter 132 is closed, display module 130 is opaque, allowing surgeon 120 to see images displayed via HMD 102 without seeing the ambient light behind the displayed image that degrades the contrast of the displayed image. When shutter 132 is open, display module 130 is transparent, allowing surgeon 120 to see the real world view. When shutter 132 is partially open, display module is transparent where shutter 132 is open, and opaque where shutter 132 is closed, such as for hiding the background behind a picture-in-a-picture (PIP) and enhancing the contrast of the image in the PIP, when displaying one or more features in a PIP during a VGS procedure, in an augmented reality-type application.

The discrete illumination states for illumination system 114 include selecting flood illumination on, off, or low; selecting coaxial illumination on, off, or low; selecting the auto illumination state. Illumination system 114 additionally includes continuous illumination states. When the auto illumination is enabled, system 100 automatically adjusts the illumination as a function of image histogram analysis, other image processing analyses, the position and orientation of HMD 102, the progress of the surgical procedure, and additional parameters. The settings for auto illumination include: Enabled and Disabled (default).

When the auto centering state is enabled, system 100 automatically centers the magnified image according to predefined settings that depend on the system mode. For instance, in anterior-segment mode the centering may be performed using the XY motors, and in posterior mode the centering may be performed either digitally by changing the displayed ROI taken from the full imaged frame, or using the XY motors when the patient's eye is moved. The centering is based on image analysis according to predefined settings that dictate the characteristics of the centering. The settings for auto centering include:

Enabled,
Disabled (default).

When auto focusing is enabled, system 100 automatically focuses the magnified image according to user preferences. The user may designate a point in the surgical field that the system then locks on (if the camera head or the patient are moved) and keeps in focus. The user may alternatively choose to automatically focus on a tip of a tool. In posterior procedures, the user may choose to automatically focus on the center of the illuminated region. The settings for auto focusing may include:

Lock,
Tooltip,
Center,
Disabled (default).

Various color correction schemes may be enabled through the system modes. For example, options include:

Correction for flood illumination (default),
Corrections for various fiber illumination sources,
Corrections for enhancement when using various dyes, and
User configurable color schemes.

The eye-inversion state is indirectly controlled via the system modes. In the Normal state (default), the video stream from the left camera 140B is streamed to the left eye of surgeon 120 and the video stream from the right camera 140A is streamed to the right eye. The inverted state is typically used for posterior segment ophthalmic procedures using a non-contact lens. In the inverted state, the video stream from the left camera 140B is streamed to right eye of surgeon 120 and the video stream from the right camera 140A is streamed to the left eye. The images are also rotated by 180 degrees.

The motor velocity state defines parameters for various motors of system 100 that control the cameras focus for camera system 112, the X, Y, and Z position for camera head 110, and the like. The options for this state include: high/low speed.

The motor boundaries state confine the degrees of freedom for each of the motors integrated within camera head positioner 111. The options include: Full motion, and Limited motion.

The display of picture-in-picture (PIP) is controlled by surgeon 120. The options for each PIP include: Off (default); On; Other. Surgeon 120 may define several predefined options for the number of PIPs and PIPs locations, determine which option is effective in each system mode and what content is displayed in each PIP in each system mode.

The user interface settings defining which action corresponds to which user input may be customized, i.e. by surgeon 120, or by another operator. In some embodiments, the various settings for the user interface are controlled via touchscreen 108. The options for the user interface settings include:
- Settings for footswitch 104. These settings define which command is attributed to each button or pedals 104A, 104B, and 104C of footswitch 104.
- Head gesture definitions. These setting define which command is attributed to each head gesture by surgeon 120.
- Menu definitions. These settings define which options appear when menus are invoked by surgeon 120.
- Voice command settings. These settings switch the voice command functionality state (on/off), allowing surgeon 120 to switch the voice control features of system 100 on or off, as needed. Voice command settings may be personalized using known techniques, such as machine learning, to familiarize system 100 with commands preferred by surgeon 120. It is to be understood that this list is exemplary only, and is not meant to be exhaustive.

Computer 118 controls the display of various overlaid symbols to guide surgeon 120 during the surgical procedure. The display overlay settings define which symbols are overlaid on the image displayed via HMD 102, and may be customized by surgeon 120.

Additional settings may control other system characteristics, such as pertaining to additional cameras or sensors (not shown) in camera head 110. For example, through the iOCT settings, surgeon controls iOCT image acquisition. Settings include: off (default), on, iOCT scanner operation, mode specific settings, such as for anterior segment vs. posterior segment modes, and other.

System 100 enables surgeon 120 to view anatomy-based data overlaying the live image feed displayed via HMD 102. Surgeon 120 can customize the overlaying of data on the live video feed such that it is not distracting. Settings allow for customization, such as toggling the overlaid data on and off, showing only part of an overlay and manually moving the overlay border.

The anatomy-based data can be displayed in registration with the live magnified image, where "registration" is understood to preserve the spatial relation between the anatomy-based data and the live magnified stereoscopic images acquired by cameras 140A and 140B. The use of the term 'registration' herein is intended to capture a broader meaning that what is understood in conventional contexts for image registration. Registration for images may relate to a transformation or alignment of at least a portion of one image onto at least a portion of another. The registration performed herein additionally includes accurately locating a corresponding location on two images using any suitable technique, such as identifying similar features, without necessarily aligning at least a portion of the two images.

Registration can be based on pre-calibrations and on matching features in the anatomy-based data to features detected in the images acquired in real-time by cameras 140A and 140B. The two cameras 140A and 140B are pre-calibrated, so the direction and depth (hence the location) of each feature imaged by cameras 140A and 140B can be calculated, and vice versa: a feature or symbol may be overlaid on each of the live images to appear at a desired location relative to cameras 140A and 140B. Registration as defined herein is not to be confused with registration for visor-guided surgery (VGS) or navigational procedures, in which models of the anatomy are registered to a tracker coordinate system. In some embodiments, the correspondence between the anatomical data and the live image is established using position-related data. The correspondence between the anatomical data and the displayed image may be preserved using techniques other than tracking, such as with position data mapping the pre-operative data with the real time data.

The anatomy-based features may include OCT images (both pre- and intraoperative), 2D maps of the retina such as a retinal thickness map, a 3D model of an epiretinal membrane derived from a volumetric OCT scan, a 3D model of a cornea generated by a corneal topographer, a desired orientation of a toric intraocular lens (IOL) relative to an eye, preplanning information as marked by a surgeon on a 2D image of the patient's retina, intraoperative markings made by a supervising surgeon, and the like.

In some embodiments, a snapshot of the retina taken at one stage of an operation with one magnification level is used as a mini-map for later stages of the operation performed at with a higher magnification level. During retinal surgery, a surgeon typically uses fiber illumination that when held close to the retina illuminates only a small portion of the retina. The mini-map allows for better spatial orientation when working with higher magnification levels. The mini-map is displayed in PIP, and a circular (or other) symbol overlaid on the mini-map indicates the location of the illuminated area on the snapshot. A real-time registration algorithm allows for maintaining the registration of the live video feed to the snapshot even when the eye or camera head are moved. This technique is also useful for endoscopic procedures in which a symbol representing the footprint of the video is overlaid on a mini-map displayed in PIP, while the endoscope video is presented in full-screen. The registration of the endoscope video to the snapshot may be based either on feature matching or on tracking the endoscope.

In some embodiments, symbols are overlaid on the live video to indicate data locations of images displayed in PIP. System 100 allows surgeon 120 to customize this feature, such as by controlling PIP transparency, and location of the PIPs on the FOV of HMD 102. For example, one such symbol may be a line overlaid on the live magnified image stream showing the location in the live image of the patient's anatomy corresponding to pre-op images that are displayed in PIP. The line represents the location and angle of the preoperative OCT B-scan that is displayed in a PIP, relative to the live image.

In some embodiments, symbols are overlaid on an image displayed in PIP to indicate locations of features that appear in the live video. One example is a symbol overlaid on a snapshot used as a mini-map, as described above. As another example, a line representing the angle of a toric IOL as appears in the live magnified image may be overlaid on a preoperative image of the eye displayed in PIP. The angle of the line is corrected in real-time for both the rotation of the eye and the instantaneous angle of the IOL within the eye.

User interface 160 provides for viewing multiple images displayed inside a PIP or PIPs overlaid on top of the display of a live image feed. For example, such images may relate to pre-operative data, OCT images, notes, intra-operative live data such as B-scan images from an iOCT, video acquired via endoscope, and the like. Through the menu, surgeon 120 controls the PIP position at a location of his choosing, such as at the upper left corner of the field of view. This feature allows surgeon 120 to view the pre-operative or live data alongside the live image feed, which occupies the central area of his field of view. The size and position of the PIP, as well as the content displayed therein is set by surgeon 120 via UI 160.

The figures described below are intended to illustrate an exemplary implementation for a user interface implemented as menus overlaid on the field of view, allowing surgeon 120 to enter and exit from the Pre-op system mode by maneuvering through the menu items of the displayed menu, and to browse pre-op data in PIP alongside with symbols registered to the live image. Some menu items represent actions that are performed when selected, and other menu items represent additional menus that lead to additional sets of actions. Surgeon 120 navigates the user interface through footswitch 104 and head gestures as described above.

Figure 6A:
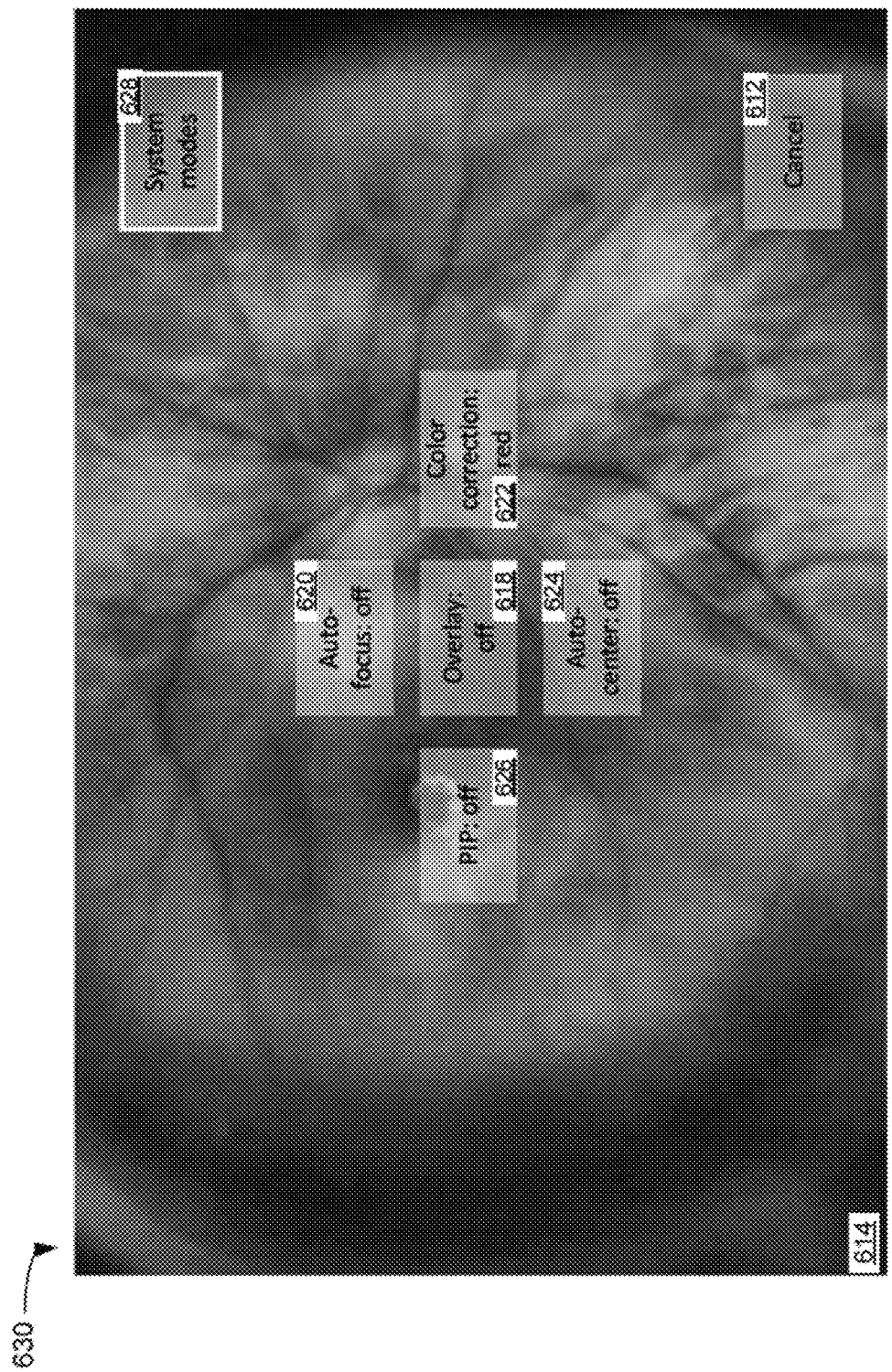
FIG. 6A shows menu overlaid on live image feed allowing the user to interact with the system and switch to different system modes, constructed and operative in accordance with a further embodiment of the disclosed technique.

Reference is now made to FIG. 6A, which shows a menu 630 overlaid on live image feed 614, allowing the user to interact with the system and switch to different system modes, constructed and operative in accordance with a further embodiment of the disclosed technique. Menu 630 displays the following menu items as system settings that are configurable by surgeon 120: Overlay 618, Auto-focus 620; Color correction 622; Auto-center 624; PIP 626; System modes 628, and Cancel 612.

The overlay setting is currently turned off as indicated by the 'off' displayed on menu item 618, indicating to surgeon 120 that by selecting item 618, the overlay may be switched on. The auto-focus setting is currently turned off as indicated by the 'off' displayed on menu item 620, offering surgeon 120 to switch overlay on by selecting item 620. Similarly, color correction is currently set to red, as indicated by 'red' displayed on color correction menu item 622, offering surgeon 120 the option of switching to a different color correction by selecting this menu item. The auto-center setting is currently set to "off", as indicated by "off" displayed on menu item 624, offering surgeon 120 the option of switching this setting on by selecting this menu item. The PIP setting is currently set to "off" as indicated by "off" displayed on menu item 626, offering surgeon 120 the option of switching this setting on by selecting this menu item. Cancel 612 and System modes 628 are provided to allow surgeon 120 to exit the menu and switch to a different system mode, respectively. System modes menu item 628 is currently highlighted, indicating that surgeon 120 may now select this menu item.

In one embodiment, when the "color correction" menu item is highlighted, a sub menu is opened that includes various color correction options, one of which allows switching off the color correction feature. In some embodiments, when a menu item of the color correction sub-menu is highlighted, before being selected by having the surgeon release footswitch 104, the effect of the color correction scheme corresponding to the highlighted menu item is implemented and displayed on the live image. This allows surgeon 120 to see the effect of the different color correction schemes before selecting one of them. This feature may be enabled for additional image processing functionalities, such as image sharpening, and the like.

In some embodiments, the opened menus are displayed at the periphery of the image, as opposed to the center, allowing surgeon 120 to evaluate the effects of the various image processing and color correction options without the menu covering and blocking portions of the image. The menu items may be displayed vertically at the periphery. However, navigating the menu does not require that surgeon 120 shift his gaze from the live image. To scroll through and highlight the various menu items, surgeon 120 moves his head up and down while keeping his focus on the center area of the live image.

Surgeon 120 navigates between the different menu items while pressing footswitch 104 and moving his head to orient his gaze from between the menu items. For example, to select system mode menu item 628, surgeon keeps menu item 628 highlighted for a predefined period of time (e.g. "long gaze") while pressing on footswitch 104. This will bring up the system mode menu, shown in FIG. 6B below, and collapse the advanced menu that is currently presented into item 616 in the periphery of the field of view, allowing surgeon 120 to revert back to this menu by orienting his gaze while pressing footswitch 104, accordingly. Thus, in one implementation, to navigate between different menus and open sub-menus, surgeon 120 highlights the different menu items that represent collapsed menus for the predefined time period while pressing on footswitch 104. Releasing footswitch 104 is not necessary to navigate between the various menus. However, to select a menu item for activating or deactivating the system setting associated with the selected menu item, surgeon 120 releases footswitch 104 while orienting his gaze at that menu item. Thus, footswitch 104 enablement is required for performing an action on system 100, but not for navigating between menu items representing possible actions that may be taken.

Figure 6B:
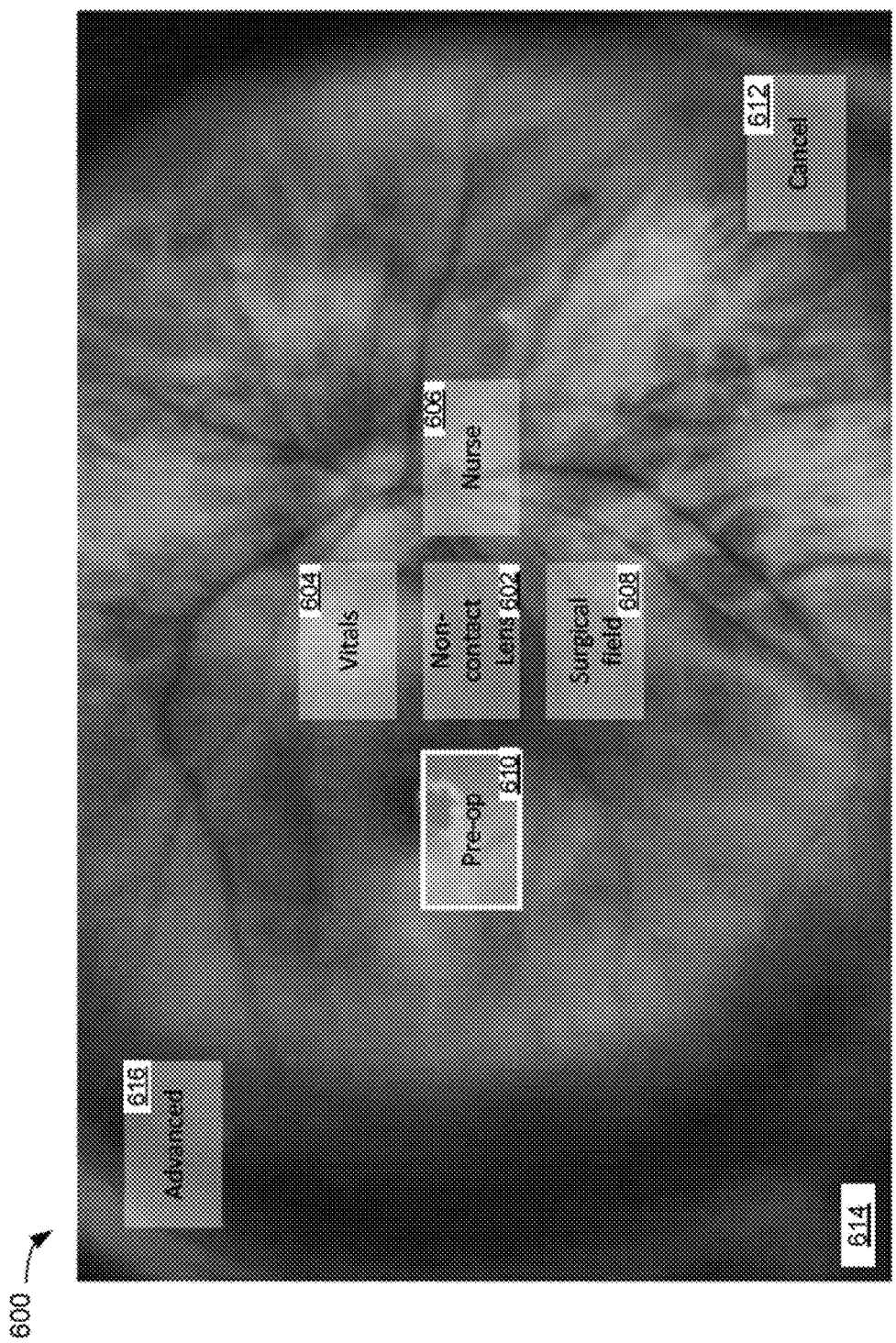
FIG. 6B shows a system modes menu overlaid on the live image feed after selecting the system modes menu item from the menu of FIG. 6A, constructed and operative in accordance with another embodiment of the disclosed technique.

Referring to FIG. 6B, a system modes menu 600 is shown overlaid on the live image feed, after the system modes menu item 628 of menu 630 of FIG. 6A was selected, constructed and operative in accordance with another embodiment of the disclosed technique. On selecting menu item 628 of FIG. 6A by gazing at menu item 628 for a period of time while pressing on footswitch 104, system modes menu 600, corresponding to system modes menu 400 of FIGS. 4A-4D, is displayed in place of menu 630 of FIG. 6A. The previously displayed "Advanced" menu 630, shown in FIG. 6A, is collapsed to a menu item 616 displayed in the periphery of the field of view, such as at the upper left corner, as shown in FIG. 6B. System modes menu 600 displays a Non-contact lens menu item 602, a Vitals menu item 604, a Nurse menu item 606, a Surgical field item 606, a Pre-op menu item 610, and a cancel menu item 612 overlaid on live image 614. Pre-op menu item 610 is highlighted, indicated this menu item may now be selected by surgeon 120.

Figure 6C:
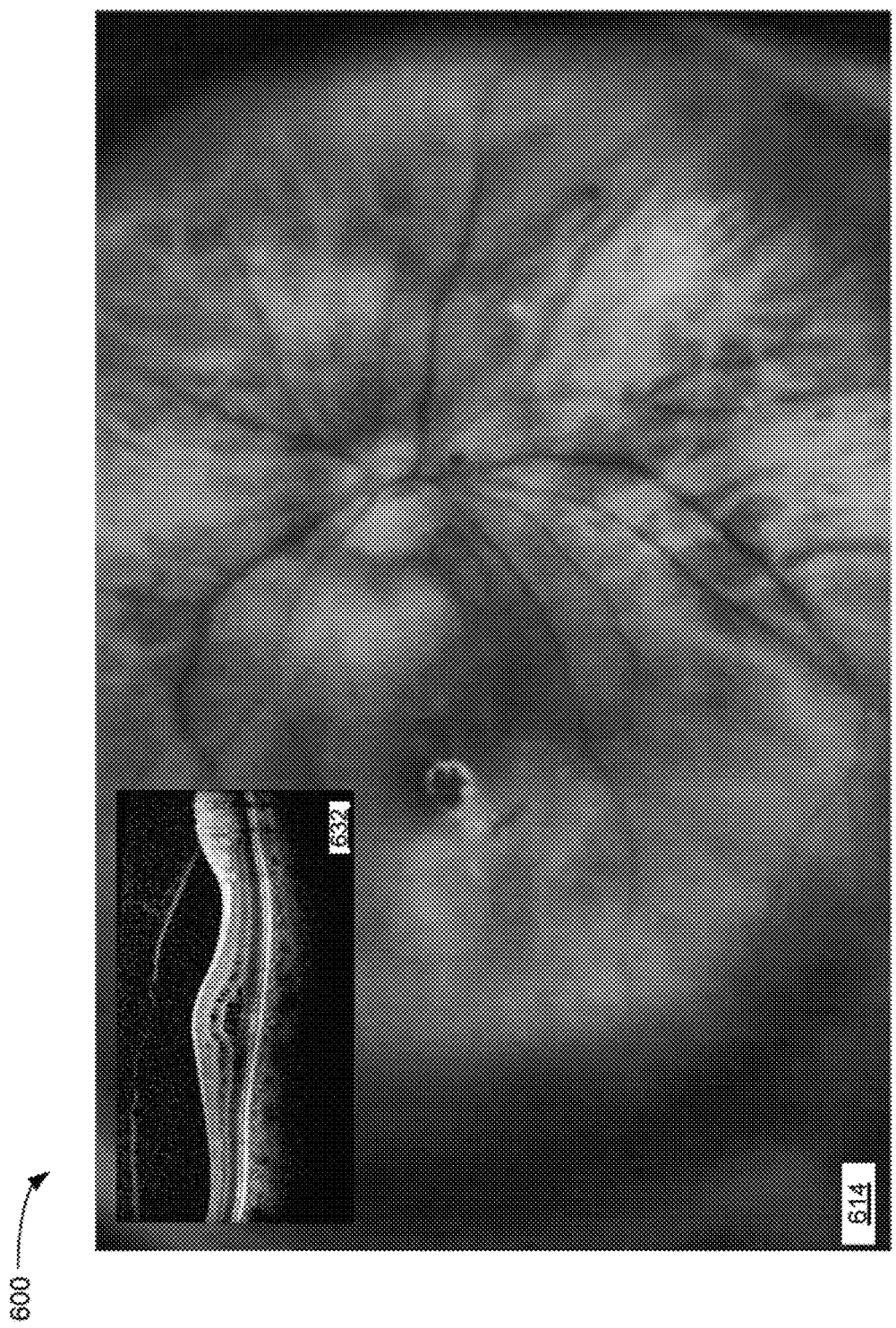
FIG. 6C shows a preoperative image displayed in a PIP overlaid on the live image feed, constructed and operative in accordance with a further embodiment of the disclosed technique.

Referring to FIG. 6C, a preoperative image is displayed in a PIP overlaid on the live image feed, constructed and operative in accordance with a further embodiment of the disclosed technique. On selecting menu item 610 ("Pre-op") of FIG. 6B by releasing footswitch 104, the system mode switches to the Pre-op mode. In this mode the user selects a folder of pre-operative OCT images to be displayed in a PIP. In some embodiments, this mode allows surgeon 120 to adjust and define the PIP according to user-defined settings, such as size and position. After selecting which pre-operative images to view in the PIP, surgeon 120 returns to the non-contact lens mode using footswitch 104 and the menu navigation technique described above. Upon returning to the Non-contact lens mode, a preoperative image 632 is displayed in a PIP in the upper left hand corner of the display of live image 614 as shown in FIG. 6C. The preoperative OCT image is of the same tissue displayed in live image 614. It is to be noted that the position and size of the PIP is exemplary only and may be user-defined by surgeon 120.

Figure 6D:
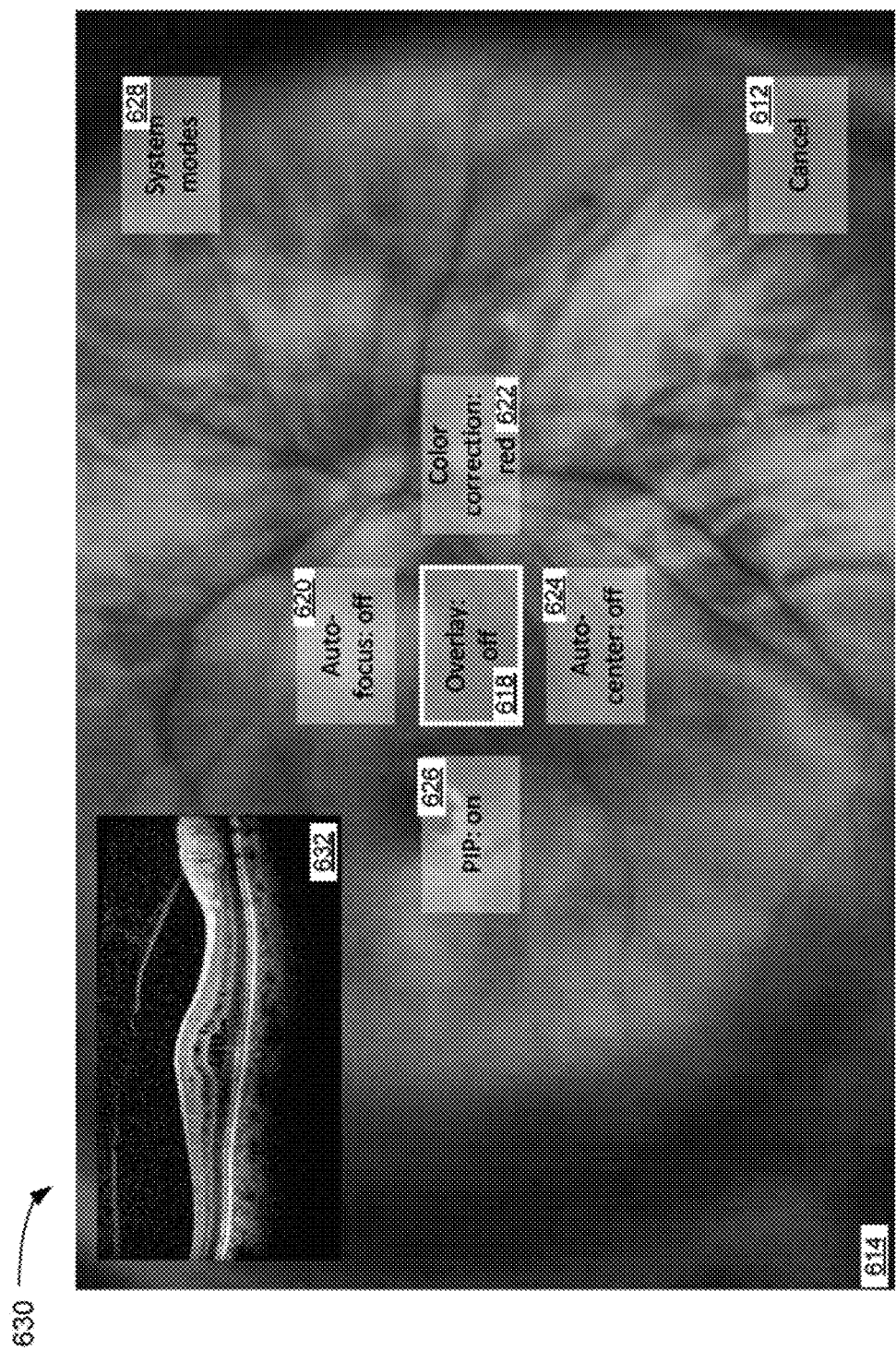
FIG. 6D shows the menu of FIG. 6A overlaid on the live image feed together with the PIP, constructed and operative in accordance with another embodiment of the disclosed technique.
Figure 6E:
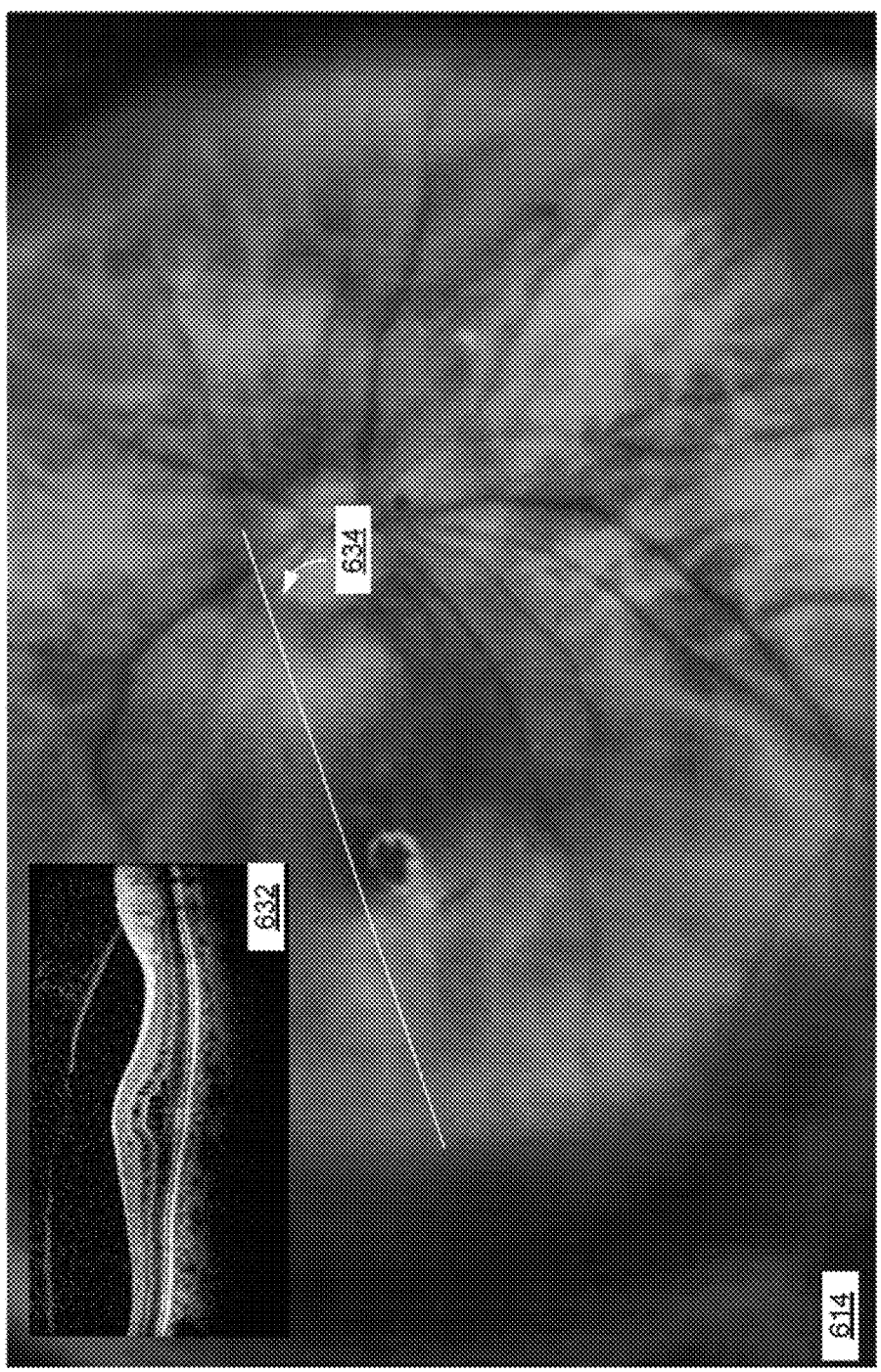
Figure 6F:
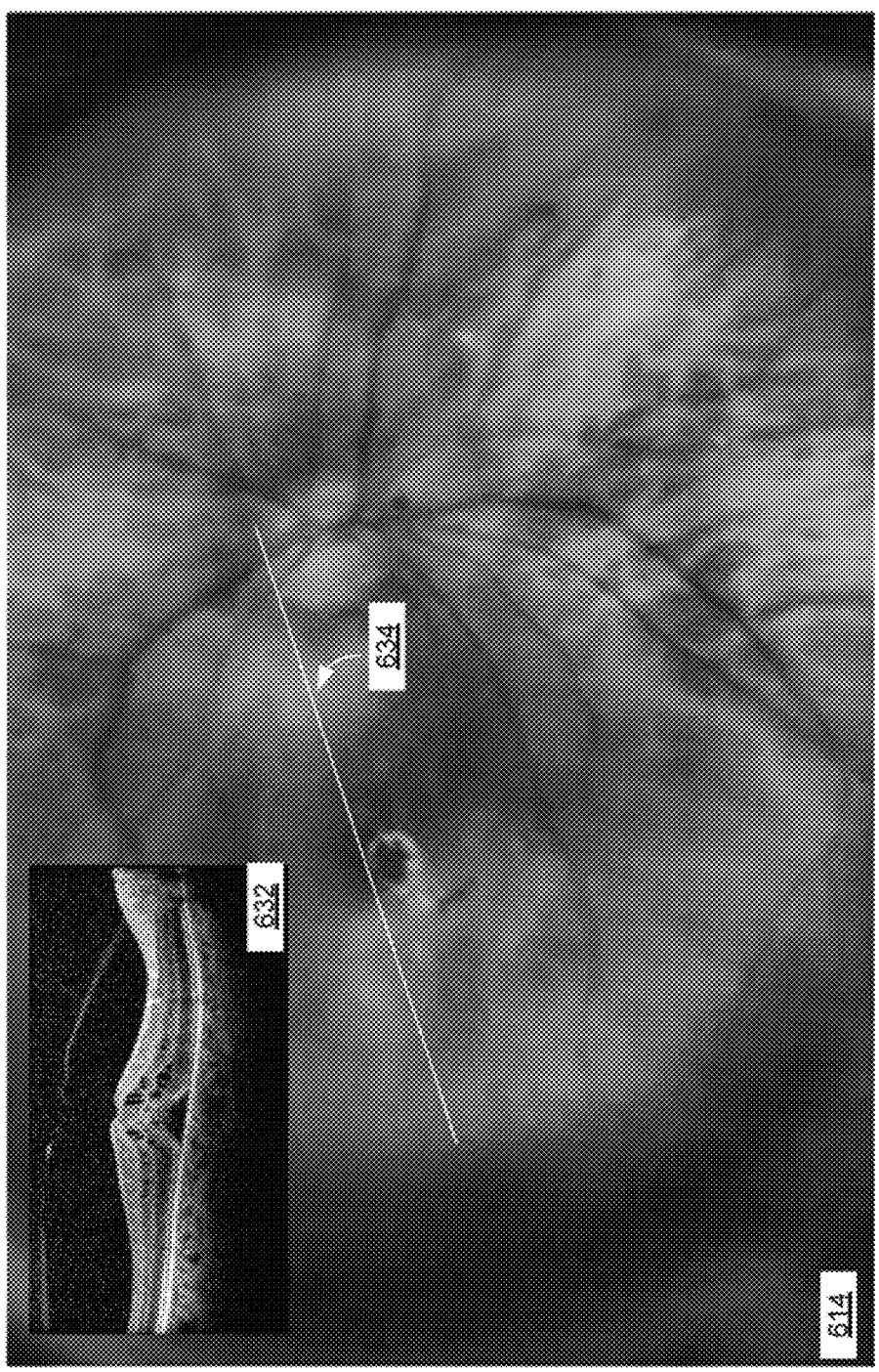
Figure 6G:
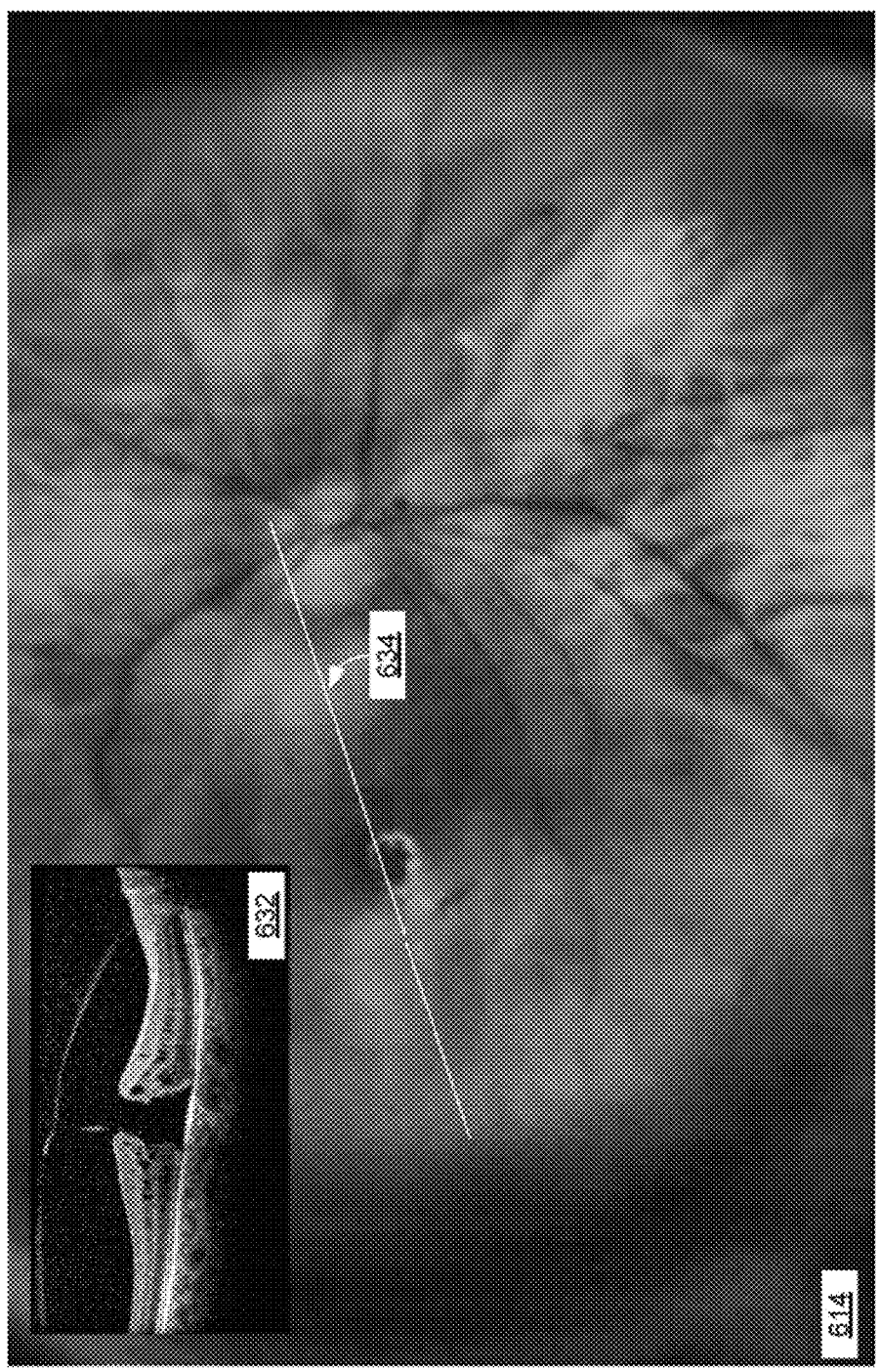
Figure 61:
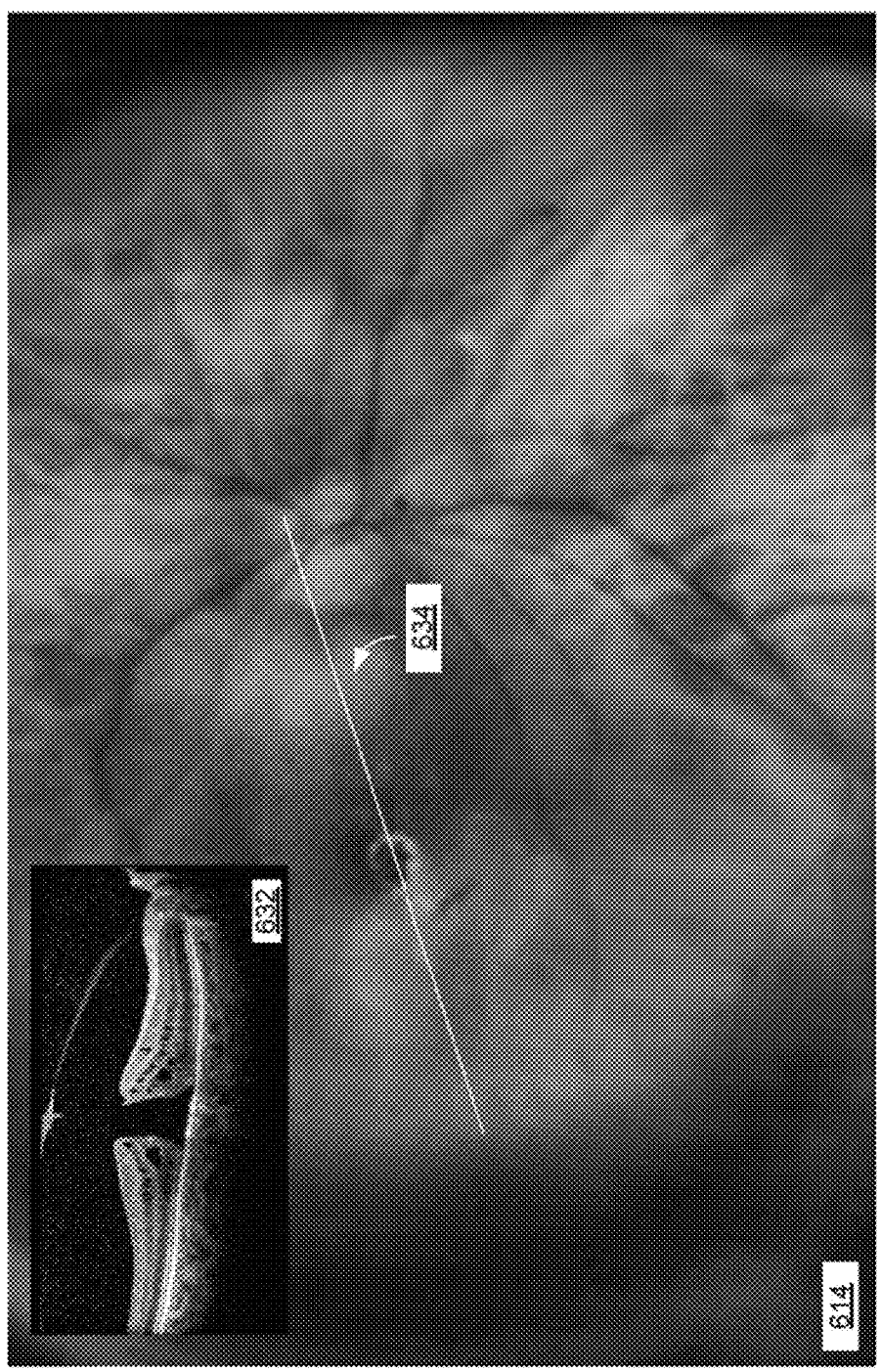
Figure 6J:
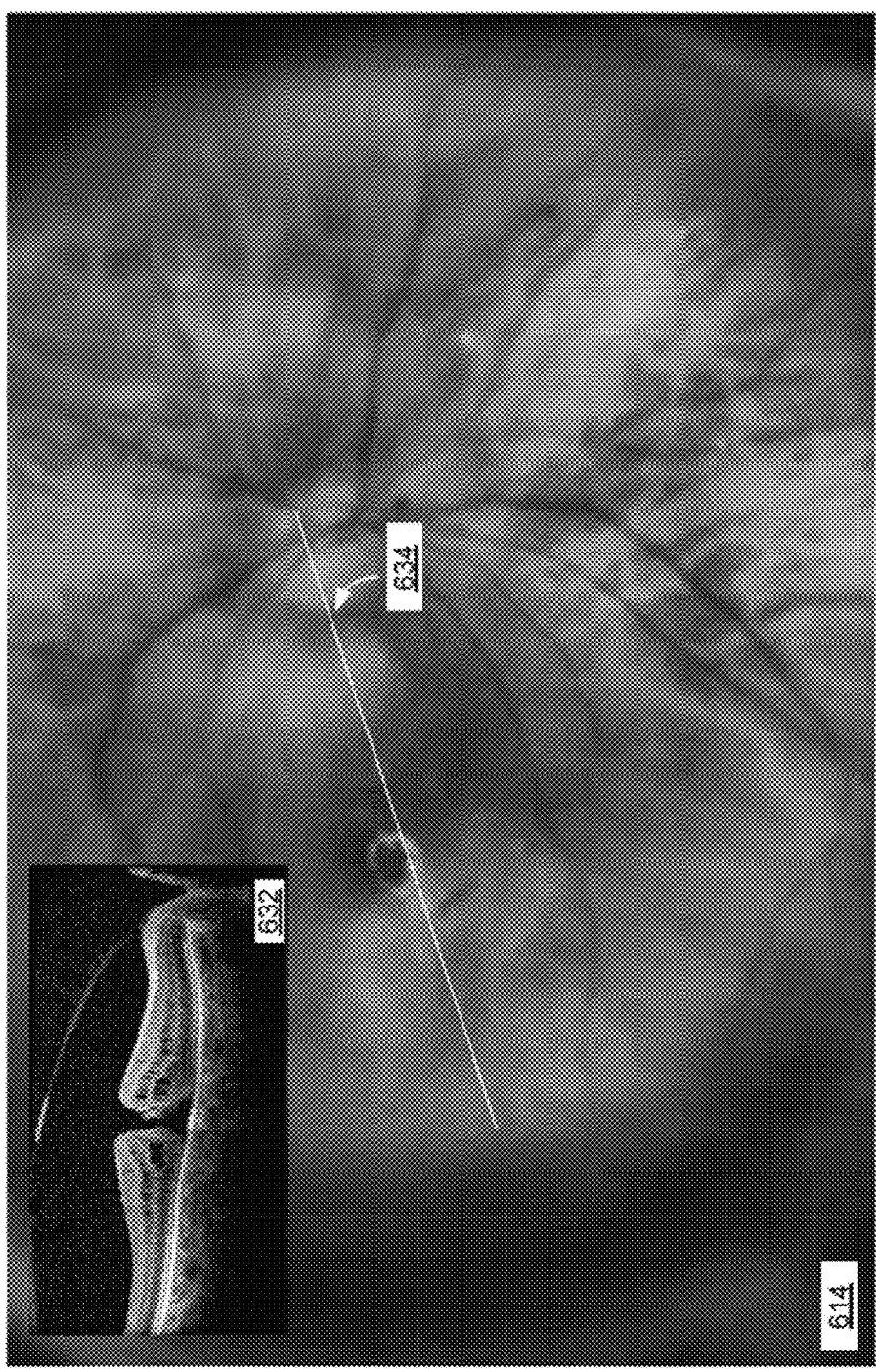
Figure 6K:
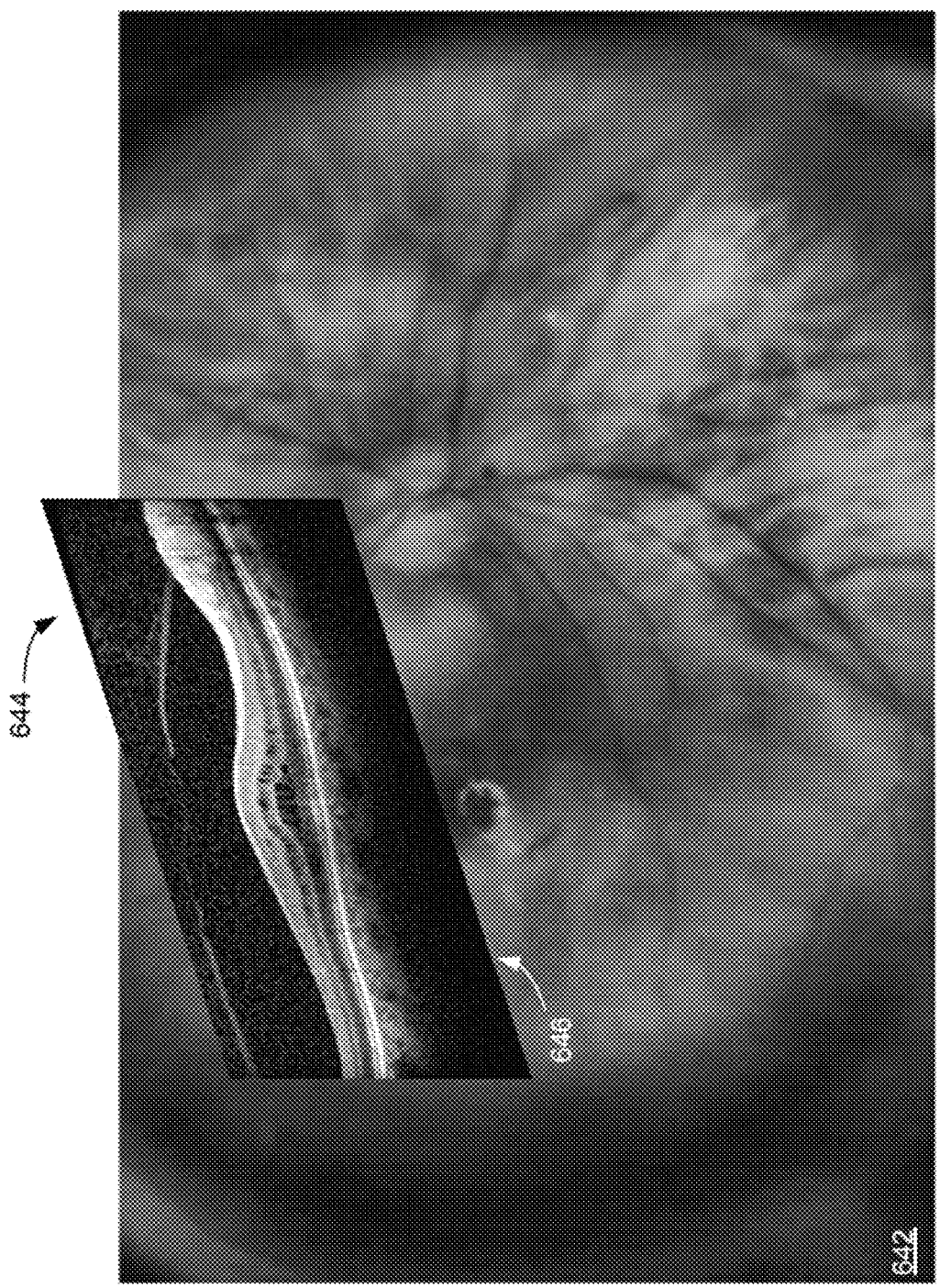
Figure 6L:
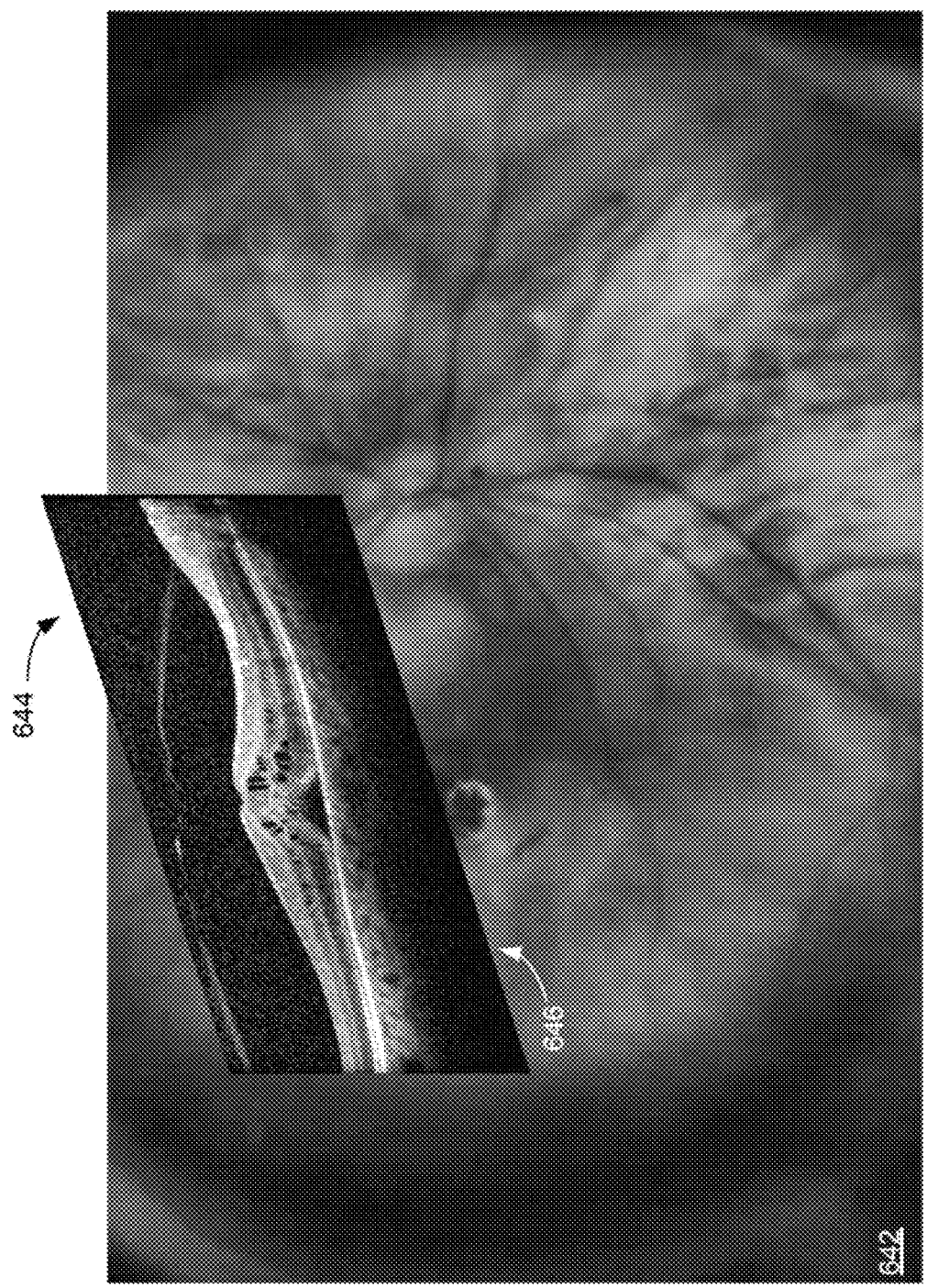
Figure 6M:
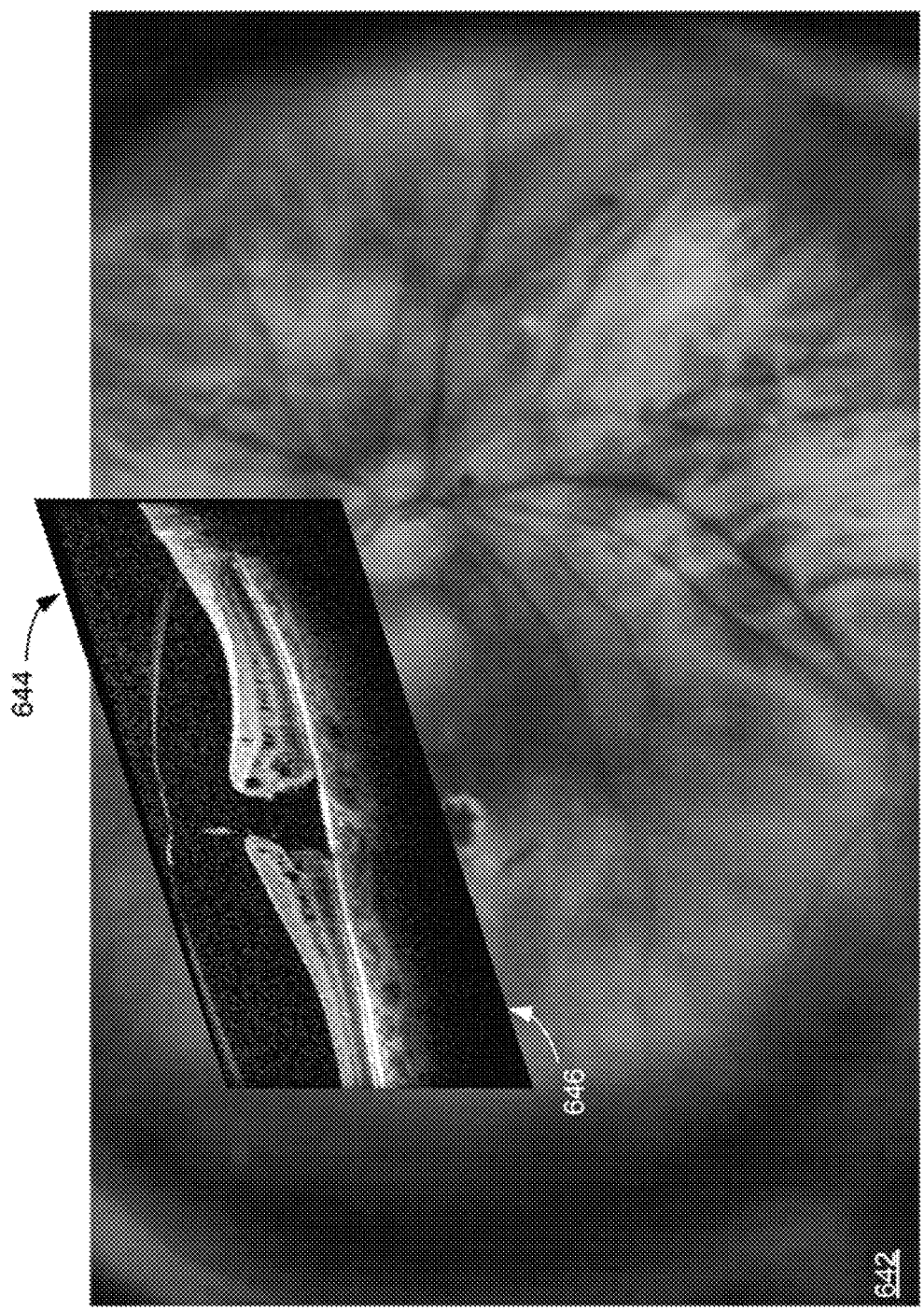
Figure 6N:
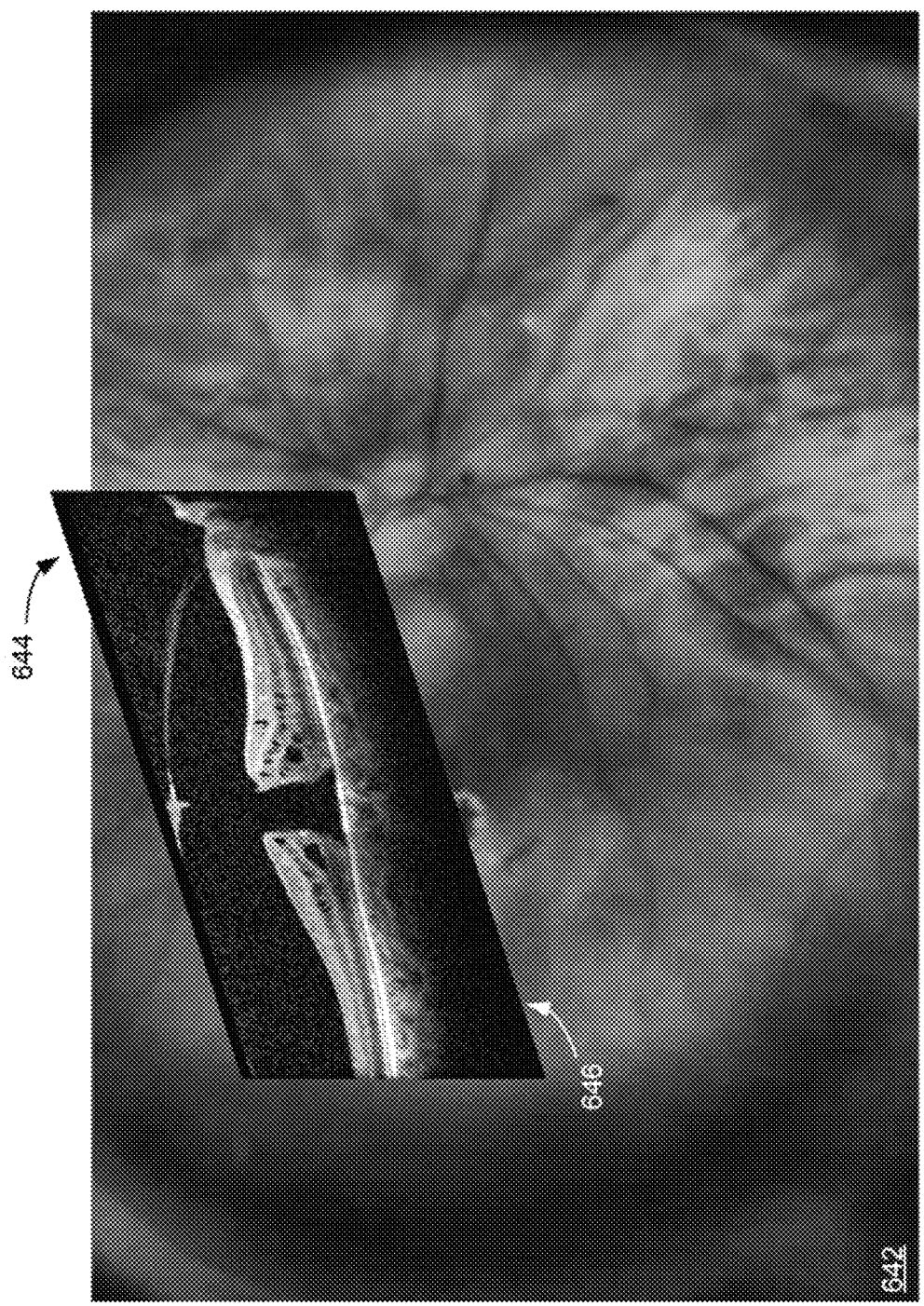
Figure 60:
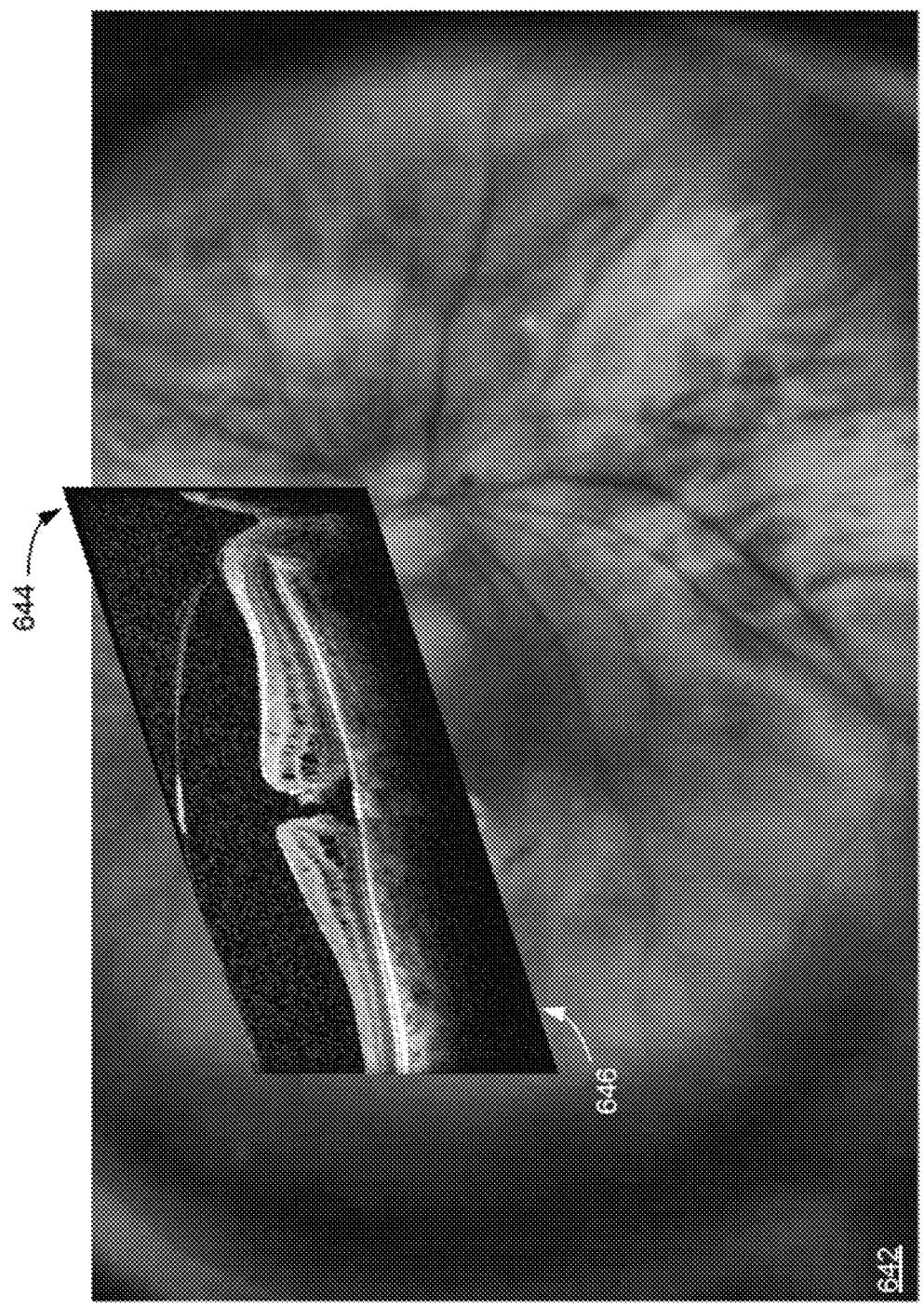
Figure 6P:
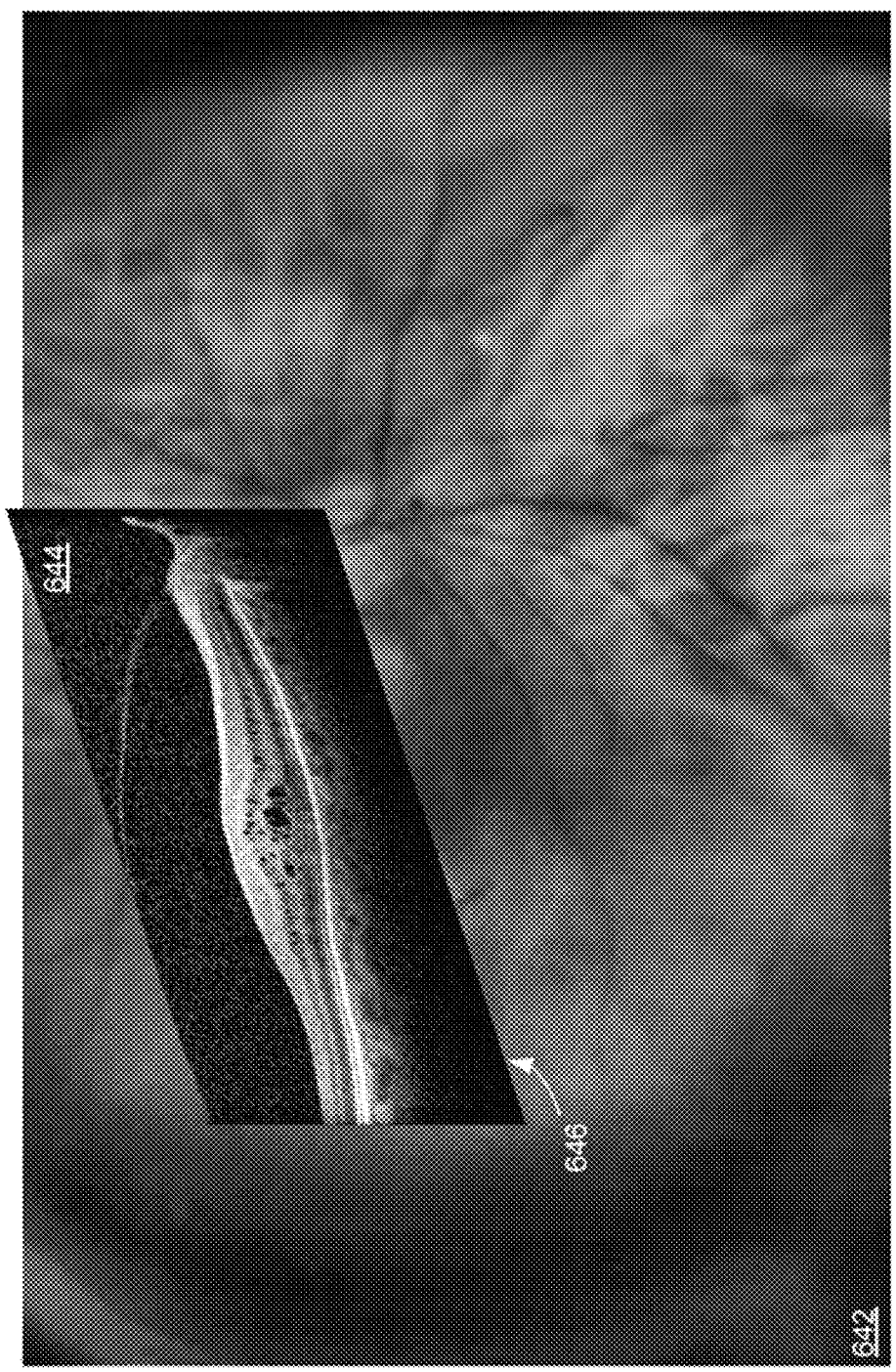

Referring to FIG. 6D, menu 630 of FIG. 6A is shown overlaid on the live image feed together with the PIP, constructed and operative in accordance with another embodiment of the disclosed technique. Surgeon 120 causes menu 630 to reappear, such as by pressing footswitch 104. Menu 630 is displayed overlaid on live image 614 with PIP 632 displayed in the upper left hand corner. Overlay menu item 618 is highlighted, indicating that surgeon 120 has selected this menu item by performing head gesture while pressing on footswitch 104. Currently the state of the overlay setting is off, as indicated by the 'off' displayed on menu item 618, inviting surgeon 120 to switch this setting on by selecting menu item 618.

Reference is now made to FIGS. 6E-6J, which taken together, show a series of live images 614 with corresponding content displayed in PIP 632, constructed and operative in accordance with another embodiment of the disclosed technique. FIGS. 6E-6J show an overlay 634 superimposed on live image 614. Overlay 634 is a line indicating the location on the live image 614 corresponding to the preoperative OCT image displayed in PIP 632. Since live image 614 is a 3D image, i.e. each eye of surgeon 120 sees a slightly different image that together form 3D image 614, line 634 is independently overlaid on each of the two images projected to the eyes of surgeon 120. As a result, surgeon 120 sees line 634 overlaid with the correct depth perception on the surface of 3D image 614, which shows a retina.

In some embodiments, computer 118 stores multiple pre-operative images in a library. As each image is displayed in PIP 632, the location on live image 614 corresponding to the image is indicated by an overlay, such as line 634. The location on the tissue indicated by each overlay 634 corresponds to the preoperative OCT image concurrently displayed in PIP 632. The user scrolls within the set of preoperative images by pressing on a pedal of footswitch 104 while simultaneously making a head gesture, (e.g. a head down rotation for scrolling down and a head-up rotation for scrolling up). As the preoperative OCT image displayed in PIP 632 changes, the corresponding location on the real-time image is calculated and displayed with overlaying line 634. In the images shown, the location on the real-time image shifts correspondingly downwards. The calculation for the corresponding location on the real-time image may be performed on a frame-by-frame basis, even when the preoperative OCT image displayed in PIP 632 has not been changed by surgeon 120, as image 614 is live and the overlay requires dynamic updating. The calculation is based on data generated by the preoperative OCT imager, comprising a preoperative image of the retina and locations on the image corresponding to all the preoperative OCT images. Using this preoperative image of the retina, the corresponding locations on the real-time image 614 can be calculated. This feature allows surgeon 120 to scroll within the pre-operative data in PIP 632 alongside the corresponding overlay on the live image feed 614 using handless gestures. It may be noted that the display of OCT images in PIP 632 is intended to be illustrative only, and does not limit the invention. PIP 632 may display other relevant content corresponding to the location on live image 614 indicated by line 634.

In some embodiments, surgeon 120 may freeze the live image while viewing preoperative data in PIP. This may be useful for drawing a feature or symbol on the live image while the PIP is displaying the preoperative data alongside the live image feed. Freezing the image while drawing is useful if the live video displays motion, for example due to involuntary saccadic eye movement, breathing, and the like. The drawn symbol may be used to guide surgeon 120 with subsequent actions, such as cutting an incision, after unfreezing the live image feed.

In some embodiments, surgeon 120 can designate a point in the image displayed via HMD 102 via UI 160. For example, a head gesture enabled by footswitch 104 may move a cursor to designate a point on the image. Alternatively, a point may be designated on the image by tracking the eye motion of surgeon 120. The designation may serve various purposes, such as:

Designating the point for manual registration. Corresponding points in both a PIP and in a live video can be designated for manually registering the image in the PIP.

Designating the point for locating a point in the registered image. After an image (or model) has been registered, surgeon 120 can designate a point in the live video and a corresponding point is highlighted in the registered image, and vice-versa.

Designating the point for invoking PIP. Small PIPs may be invoked near a point designated by surgeon 120, and the content of the PIPs may relate to the designated point, allowing surgeon 120 to focus on a point in surgical field 124 and see relevant data close to that point.

Designating the point to control the region of interest (ROI) of iOCT scanner 142. One or several 2D B-scan or 3D volumetric iOCT images are displayed alongside the live video, and the surgeon controls the exact ROI of iOCT scanner 142, by designating a symbol, e.g. a cross, on the video feed acquired by camera head 112.

Designating the point for auto-focus. Auto-focusing may be activated based on a ROI around a designated point.

In some embodiments, surgeon 120 controls a symbol overlaid on the live image feed via head gestures, and a pre-operative image corresponding to the location of the overlaid symbol is displayed in a PIP. As the location of the symbol changes, the corresponding image displayed in the PIP changes. In some embodiments, if there is no preoperative image corresponding to a selected location on the live image feed, computer 118 selects the closest preoperative image to the selected location, and indicates the distance to surgeon 120.

Reference is now made to FIGS. 6K-6P, which taken together illustrate a series of live images 642 with corresponding content displayed in a PIP 644, constructed and operative in accordance with another embodiment of the disclosed technique. The embodiment of FIGS. 6K-6P is substantially similar to that described above with respect to FIGS. 6E-6J, with the notable exception that border 646 of PIP 644 replaces line 634 of FIGS. 6K-6P, to indicate the correspondence between the content shown in PIP 644 and the tissue displayed in live image 642. In the example of FIGS. 6K-6P, PIP 644 displays an OCT cross-sectional view of the tissue shown in live image 642, however this is intended to be illustrative only, and does not limit the invention. Other content may be displayed in PIP 644, as may be relevant. The OCT images shown in PIP 644 were obtained either in a pre-operative or inter-operative stage, and stored in memory 118D (FIG. 1B) for subsequent use. During the procedure, HMD 102 displays the surface of the live tissue as live image 642. Live image 642 may be a real time video display of the tissue of patient 122, or may be a frozen portion of the real time video, such as to allow surgeon to draw features for further use, as described herein below with respect to FIGS. 6R-6V.

Superimposed on live image 642, HMD 102 displays in PIP 644 the previously acquired OCT cross-sectional view of the live tissue at the location indicated by border 646. FIGS. 6K-6P show PIP 644 overlaid at multiple different locations on live image 642, starting from a top left location on live image 642 (FIG. 6K) moving downwards and rightwards on live image 642 (FIGS. 6L-6P). For each location of PIP 644 on live image 642, the OCT image displayed in PIP 644 at that location corresponds to the cross section of the tissue indicated by border 646. In this manner, by manipulating the location of PIP 644 over live image 642, surgeon 120 may view different cross-sectional slices of the tissue.

Figure 6Q:
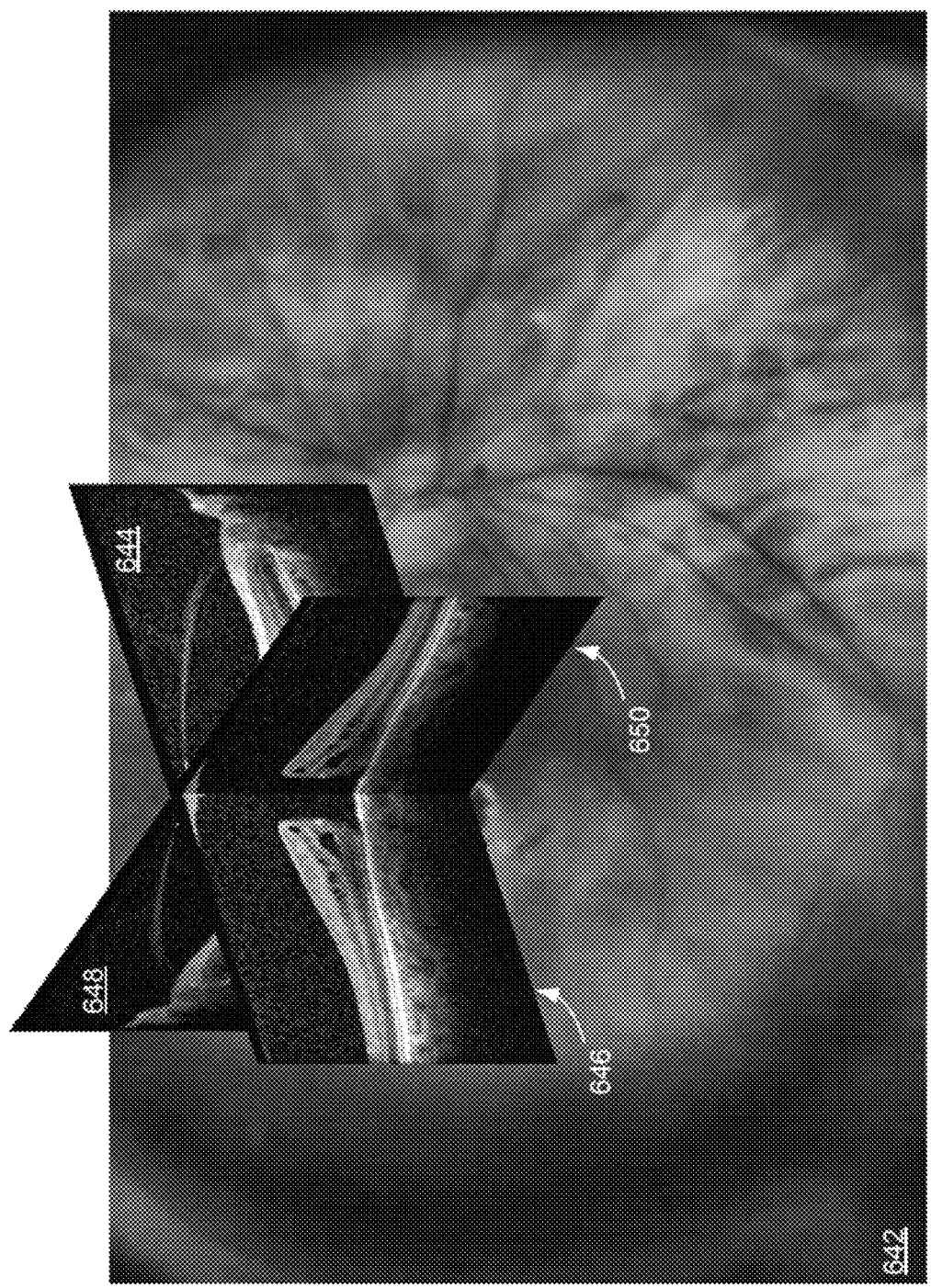
FIG. 6Q illustrates the live image of FIGS. 6L-6P with corresponding content displayed in two PIPs, constructed and operative in accordance with a further embodiment of the disclosed technique.

Reference is now made to FIG. 6Q which illustrates live image 642 of FIGS. 6L-6P with corresponding content displayed in two PIPs 644 and 648, constructed and operative in accordance with a further embodiment of the disclosed technique. The embodiment of FIG. 6Q is substantially similar to that described above with respect to FIGS. 6L-6P, with the notable that two PIPs 644 and 648 are superimposed on live image 642, each PIP showing content corresponding to the tissue indicated by borders 646 and 650, respectively. PIP 644 shows an OCT cross-sectional slice of the live tissue at the location indicated by border 646, and PIP 648 shows an OCT cross-sectional slice of the tissue at the location indicated by border 650. As above, surgeon may manipulate the locations of PIPs 644 and 648 over live image 642 to display the cross-sectional slices of the tissue at different locations.

Reference is now made to FIGS. 6R-6V which taken together, illustrate an implementation of a drawing function, constructed and operative in accordance with an embodiment of the disclosed technique. FIGS. 6R-6V illustrate the results of drawing a symbol using the drawing function displayed via HMD 102. In one embodiment, the drawing is implemented while wearing an HMD displaying the live image of patient 122, such as HMD 102. The drawing function is activated via one or more menus displayed via the HMD, allowing the wearer of the HMD to select the drawing tool (not shown) using the techniques described herein. The drawing tool is displayed over the live image, allowing the wearer of the HMD to draw the symbol overlaid on the live image by manipulating the drawing tool using one or more of: head gestures, footswitch 104, manipulating a wand, tracking eye motion, and the like. Alternatively, the drawing may be implemented via a touchscreen user interface (not shown), mouse or wand, and the like, provided with system 100.

In one mode of operation, surgeon 120 draws the feature during the pre-operation planning stage, such as for subsequent use as a guide during a medical procedure. In this case surgeon 120 sees the drawing menu and tools displayed over the live image via HMD 102, together with any pre-operative data. Surgeon 120 draws one or more preparatory symbols on the live image. In one embodiment, the live image feed is frozen during the drawing to improve accuracy. The drawn symbol remains displayed with the live image once the drawing is complete, after the live image feed is un-frozen and the pre-operational data is no longer displayed, allowing surgeon 120 to see the drawn symbol overlaid on the live image feed while performing the medical procedure.

In another mode of operation, such as in the teaching mode, a supervising surgeon (not shown) draws the symbol to guide surgeon 120 to subsequently perform the procedure. In the teaching mode, the supervising surgeon may be present in the operating room with surgeon 120 and draws the symbol locally. Alternatively, the supervising surgeon may be located elsewhere and draws the symbol remotely. The supervising surgeon may draw the symbol either via another HMD, via a smartphone, tablet or other touchscreen, or alternatively, via a mouse or wand with a standard monitor, and the like.

Figure 6R:
FIGS. 6R-6V, taken together, illustrate an implementation for drawing a symbol on the display of the live image, constructed and operative in accordance with an embodiment of the disclosed technique.
Figure 6S:
Figure 6T:
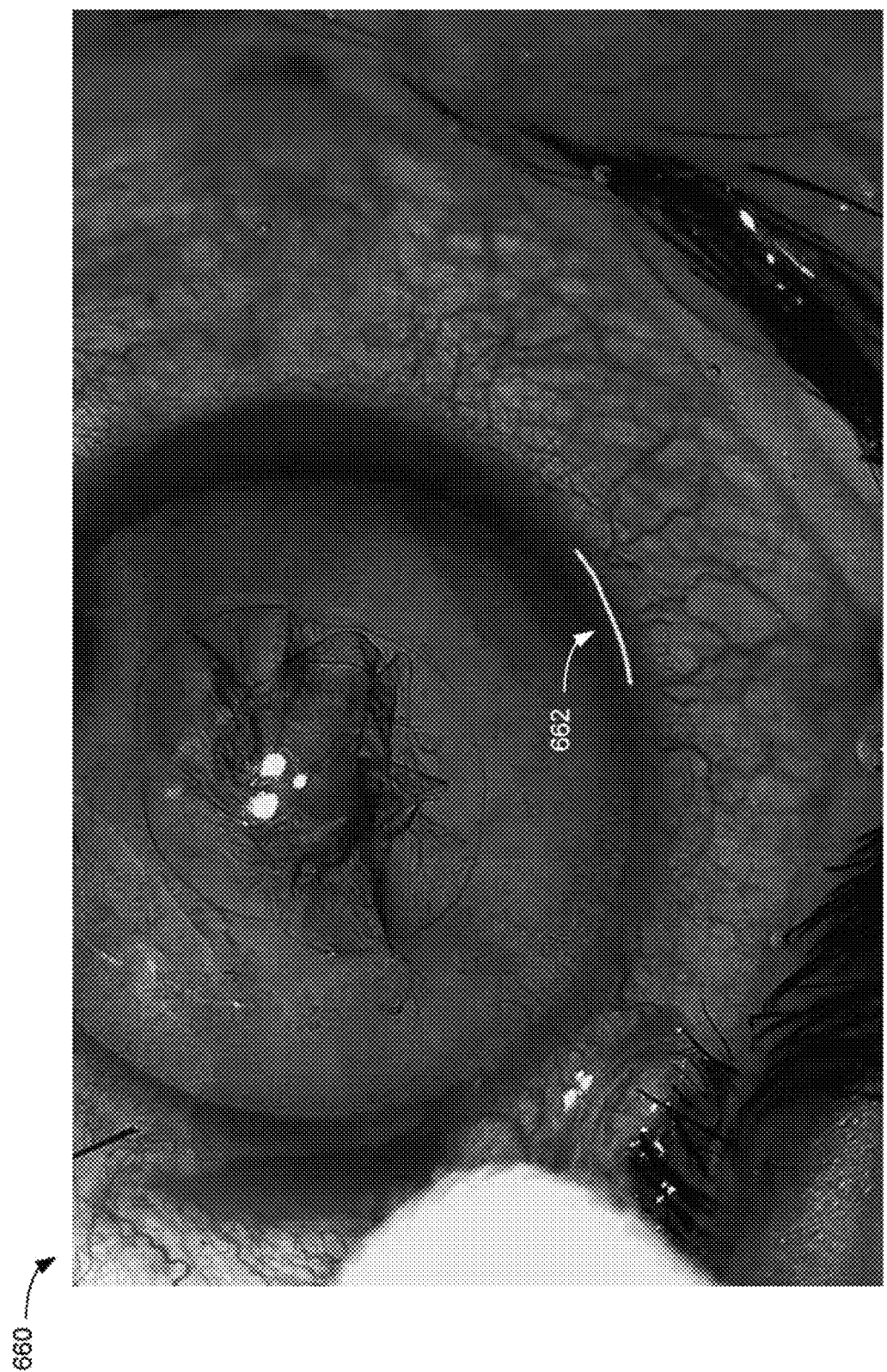
Figure 6U:
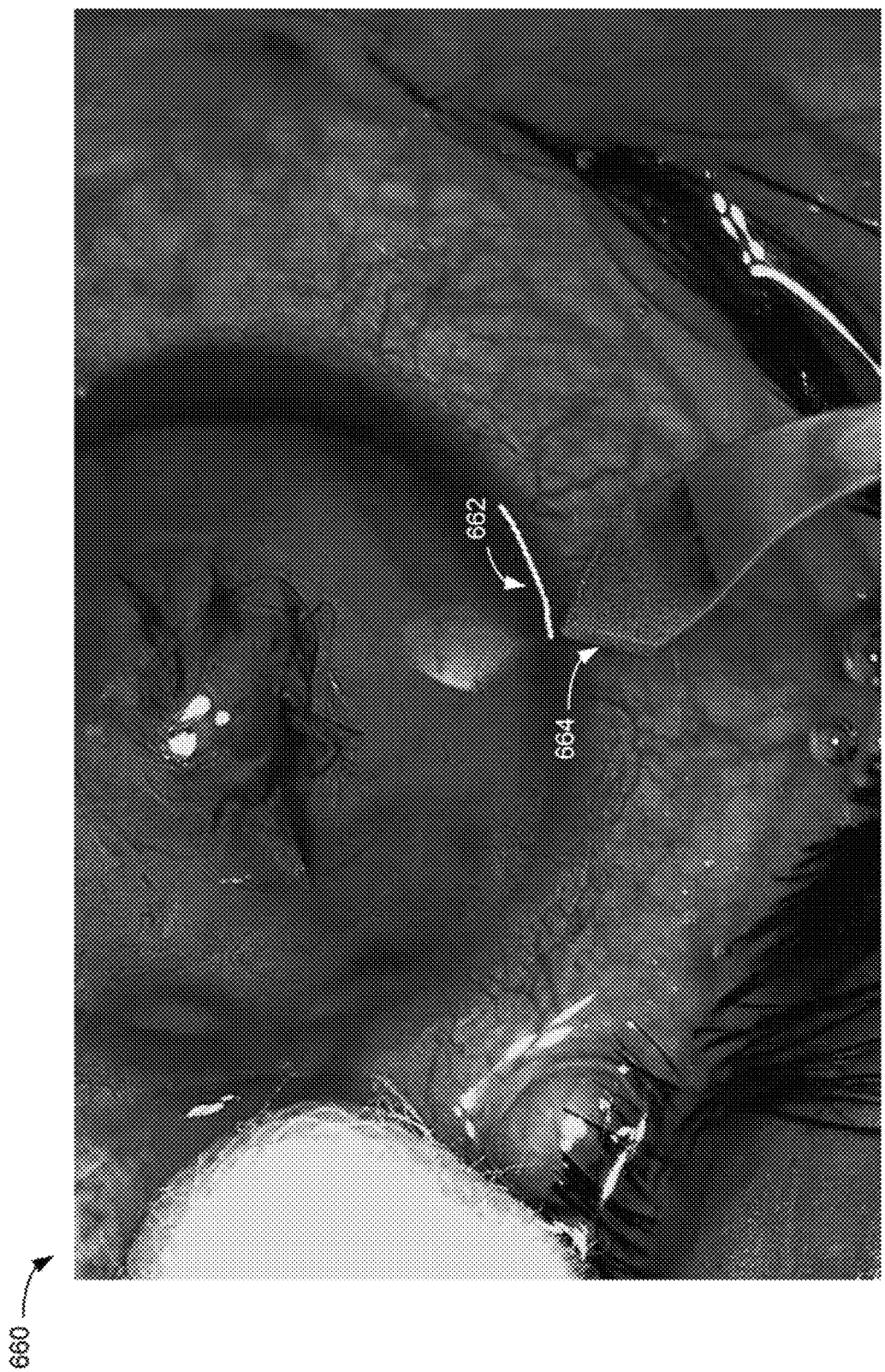
Figure 6V:
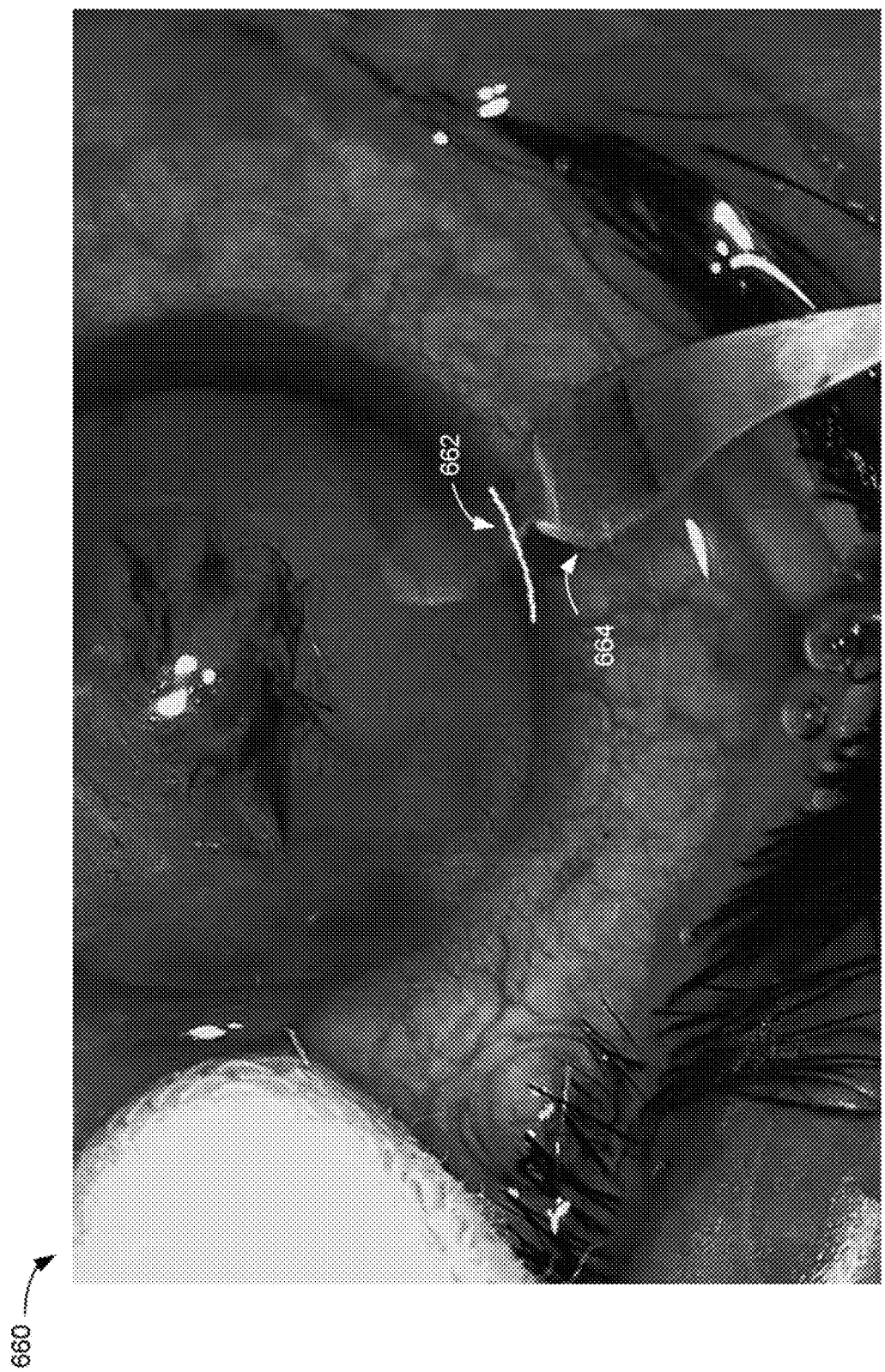

Referring to FIG. 6R, a live image 660 of the eye of patient 122 is shown, prior to virtually drawing a symbol. Referring to FIGS. 6S-6T, after selecting a virtual drawing tool from the paint menu (not shown), the surgeon virtually draws a symbol 662 on live image 660, such as to indicate the location for an incision. Symbol 662 is shown partially drawn on FIG. 6S and fully drawn on FIG. 6T. As noted, symbol 662 may be drawn by a senior surgeon wearing a second HMD while in teaching mode, or by surgeon 120 wearing HMD 102. Symbol 662 is drawn using any suitable UI technique, such as referenced herein. For example, to draw symbol 662, surgeon 120 presses footswitch 104 while moving a virtual drawing tool using head gestures that follow a trajectory corresponding to the shape of symbol 662, and releases footswitch 104 when the drawing of symbol 662 has been completed (not shown). Alternatively, a surgeon may use a mouse or her finger to draw on the live image displayed via the touchscreen. The surgeon drawing on the live image may optionally not be present in the operating room, and may be using any of various UI methods for drawing from a remote location (using an HMD displaying a 3D live image and a footswitch in her office, drawing on a tablet displaying a 2D live image, and the like). Referring to FIG. 6U, surgeon 120 uses symbol 662, drawn and overlaid on live image 660, as a guide to create an incision on the eye of patient 122. Surgeon 120 positions surgical instrument 664 at the physical location on the eye of patient 122 corresponding to the location indicated by symbol 662 on live image 660. Referring to FIG. 6V, surgeon 120 moves surgical instrument 664 along a path corresponding to symbol 662 to create an incision on the eye of patient 122. In this manner, surgeon 120, or alternatively a senior surgeon, can draw a virtual path on live image 660 prior to making the incision, to ensure that the subsequent incision is performed correctly.

After surgeon 120 has drawn one or more symbols or markings to highlight certain features, surgeon 120 may select which markings to display while viewing the live image in order to proceed with performing the procedure, using the markings for guidance. Surgeon 120 may scroll between any number of pre-drawn markings during the procedure, according to need and relevance. Once a marking becomes obsolete, to prevent these from obstructing the display of the live image, system 100 may be configured to cause the markings to fade after a predetermined time period. In one embodiment, a symbol automatically fades according to a default setting (e.g. after ten seconds). In another embodiment, a dedicated preplanning application menu allows surgeon 120 to disable (i.e. turn off) each of the markings.

Reference is now made to FIGS. 7A-7E which taken together illustrate an exemplary implementation of a menu-driven user interface for focusing on a selected area of the field of view, constructed and operative in accordance with a further embodiment of the disclosed technique. In the figures described below, the user interface is implemented as a series of menus that are overlaid on the live image stream. Surgeon 120 navigates the menus using footswitch 104 combined with head gestures, as described above.

Figure 7A:
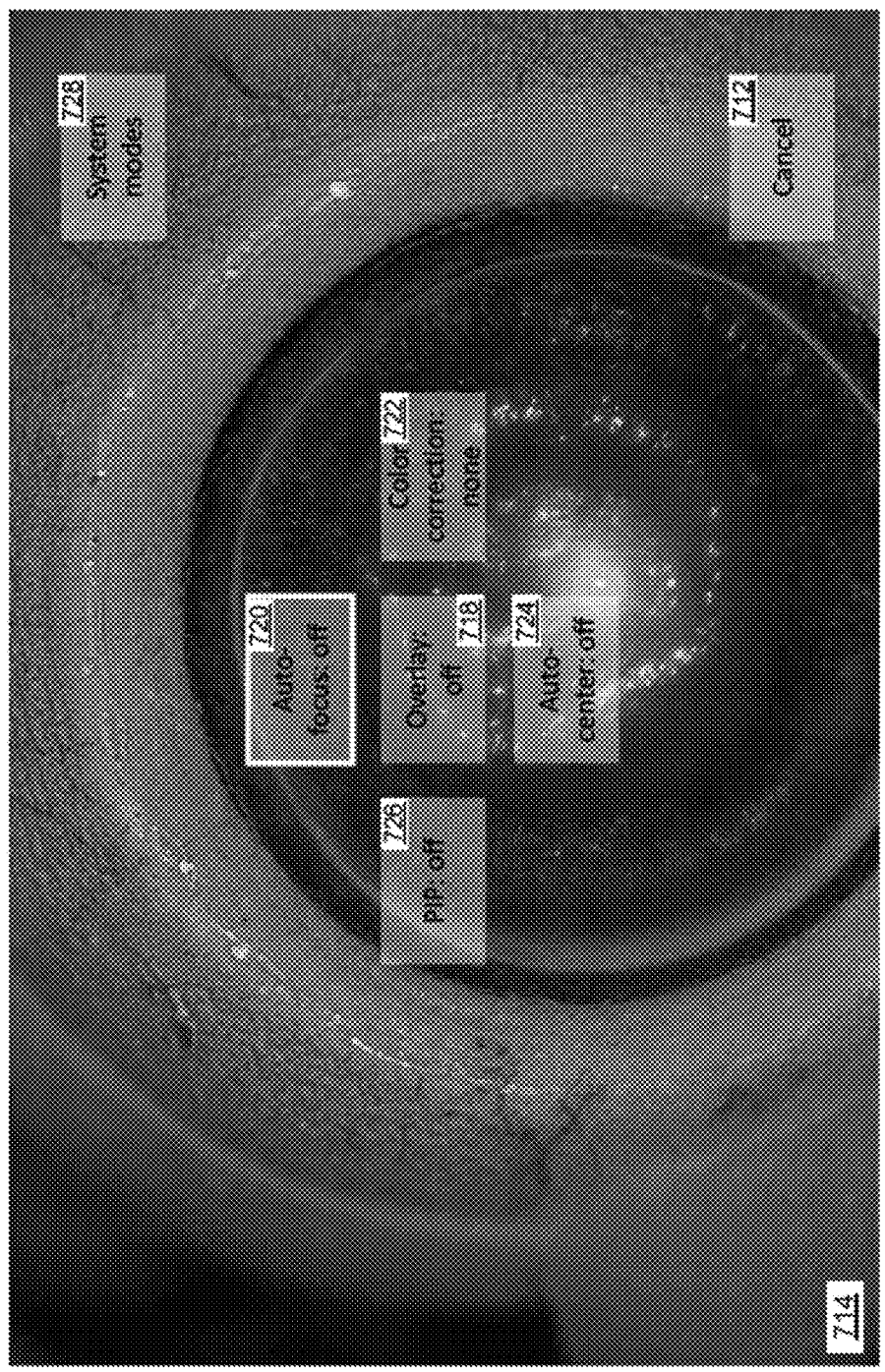
FIG. 7A illustrates a menu displayed overlaid on a live image, constructed and operative in accordance with an embodiment of the disclosed technique.

Referring to FIG. 7A, a menu 730 is displayed overlaid on a live image feed 714 for focusing on a selected area of the field of view, constructed and operative in accordance with an embodiment of the disclosed technique. Menu 730 corresponds to menu 630 illustrated in FIG. 6A described above. As with menu 630, menu 730 includes menu items: Overlay 718, Auto-focus 720, Color correction 722, Auto-center 724, PIP 726, System modes 728, and Cancel 712. Menu item 720 relating to the auto-focus features is highlighted, indicating this item may now be selected by surgeon 120. Currently the auto-focus feature is off, as indicated by the 'off' setting displayed on menu item 720, inviting surgeon 720 to switch on the auto-focus feature by 'pressing' on menu item 720 to activate it. In some embodiments, surgeon 120 turns on the auto-focus by gazing at menu item 720 (FIG. 7A) for a predefined time period, e.g. 0.5 seconds, while pressing on footswitch 104 without releasing footswitch 104, thereby highlighting menu item 720 for the predefined time period. In other embodiments, surgeon turns on the auto-focus after highlighting menu item 720 and releasing footswitch 104.

Figure 7B:
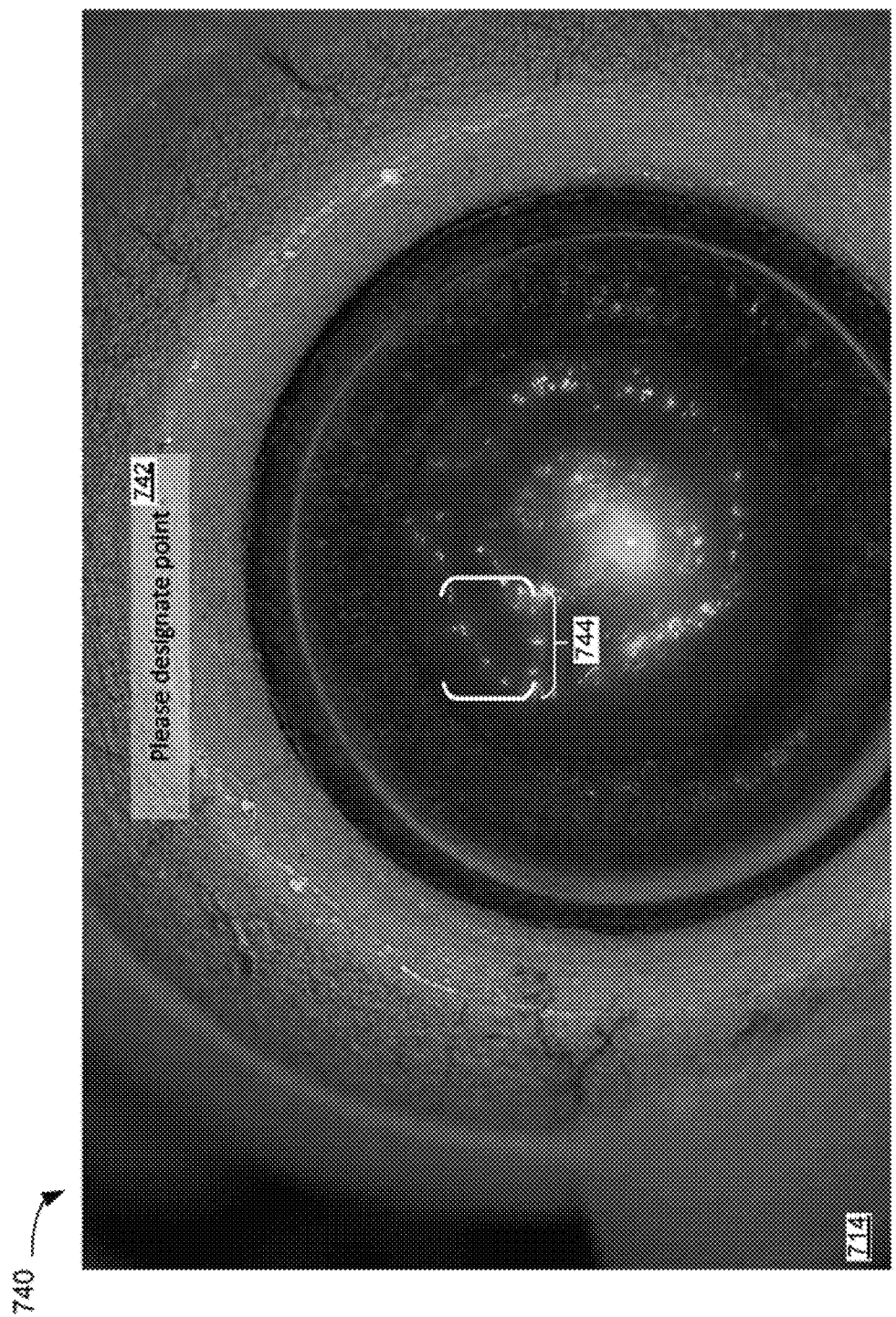
FIGS. 7B-7D, taken together, illustrate an exemplary implementation of a user interface screen that allows designating a selected area of the field-of-view for focus, constructed and operative in accordance with a further embodiment of the disclosed technique.
Figure 7C:
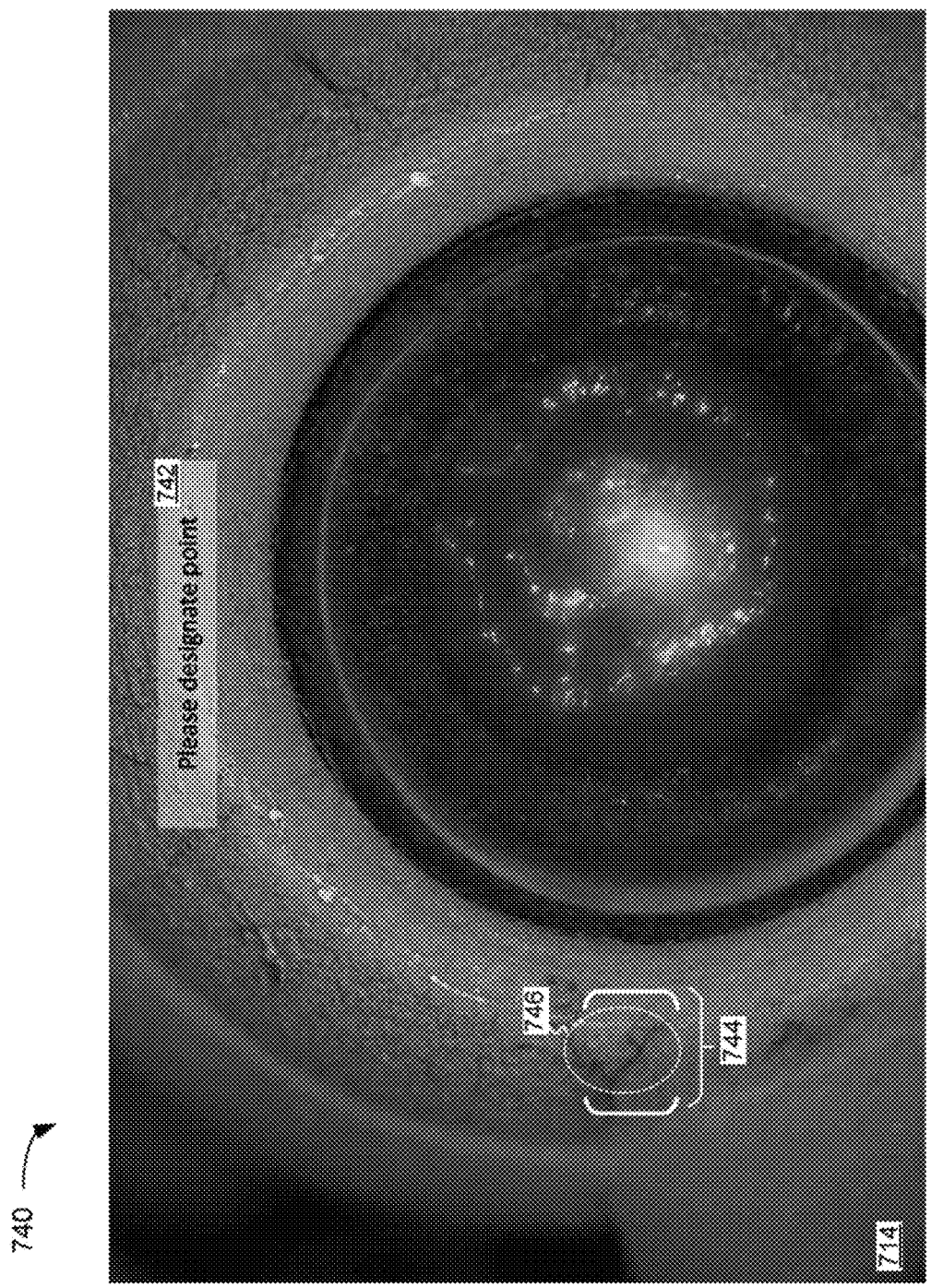
Figure 7D:
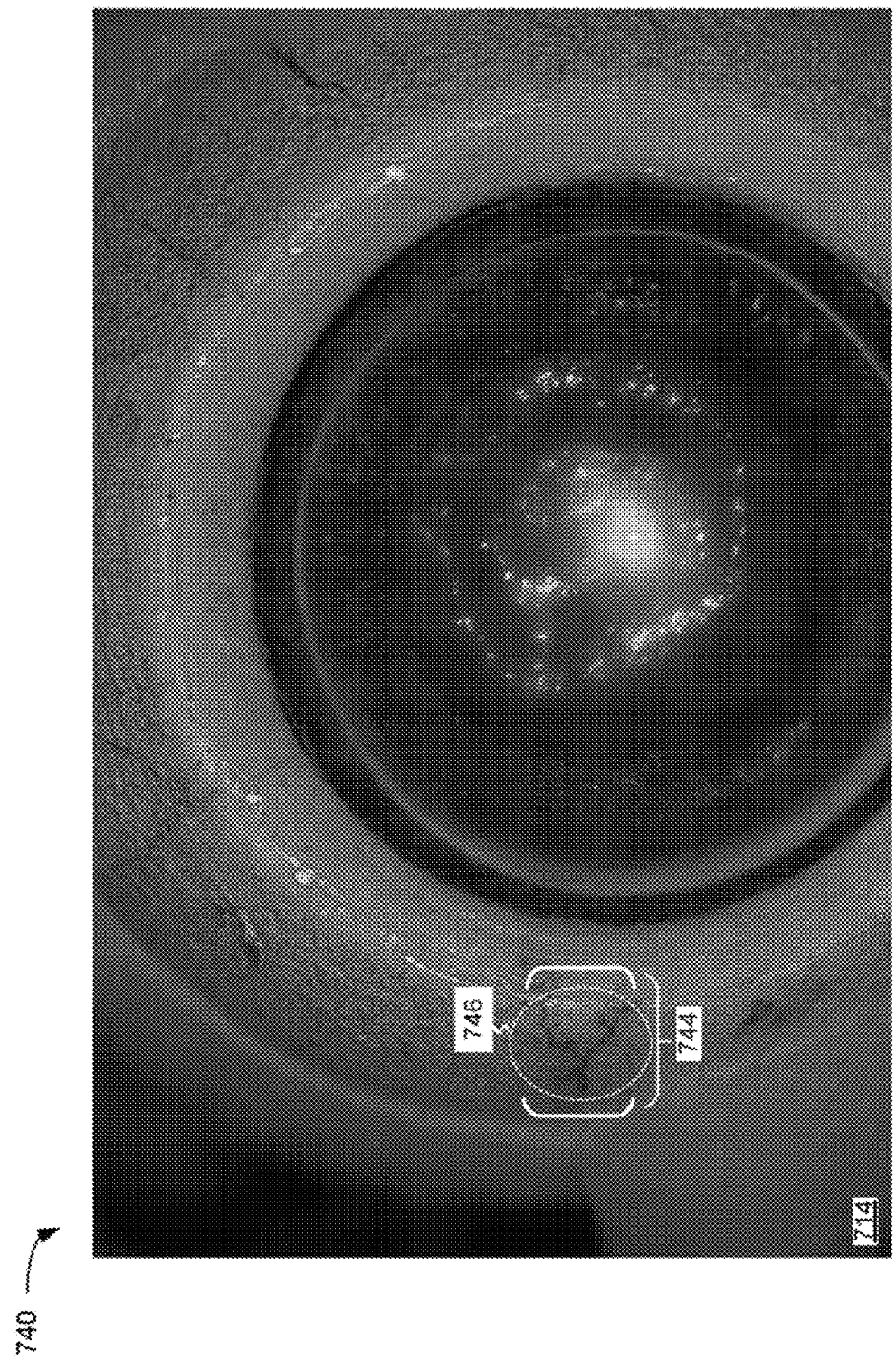

Referring to FIGS. 7B-7D, an exemplary implementation of a user interface screen that allows for designating a selected area of the field of view for focus, is shown, constructed and operative in accordance with a further embodiment of the disclosed technique. Upon activating auto-focus 720 to turn on this feature, a UI screen 740 is overlaid on the display of image 714, replacing menu 730 shown in FIG. 7A. UI screen 740 includes a prompt 742 and a designation symbol 744, shown in this implementation as a set of brackets. In some embodiments, surgeon 120 turns on the auto-focus by releasing footswitch 104. Prompt 742 requests that surgeon 120 manually designate an area within live image 714 on which to perform the auto-focus. Surgeon 120 designates the area by maneuvering designation symbol 744 over the display of image 714. The position of designation symbol 744 may be maneuvered using any of the techniques described above, such as by performing head gestures combined with footswitch 104. Optionally, surgeon 120 designates the area to focus on by gazing at the desired area for a predefined time period, such as 0.5 second. Eye tracker components 136 (FIG. 1C) tracks the gaze of surgeon 120 to detect the designation and the area selected. In some embodiments, system 100 continuously performs automatic auto-focus on designated areas based on tracking the eye motion of surgeon 120. It is to be noted that other symbols may be used as a designation symbol according to the preferences of the user, and context. For example, to accurately designate a specific point, the designation symbol may be an arrow, or cursor symbol, and the like.

Referring to FIG. 7C, surgeon 120 moves designation symbol 744 to a region 746 on the left side of image 714 that is not sufficiently focused. Region 746 is indicated by a dashed circle. Surgeon 120 moves designation symbol 744 using any suitable UI technique, such as by rotating his head leftwards while pressing on footswitch 104. Surgeon 120 designates region 746 on which to improve the focus. When the auto-focus is activated by highlighting menu item 720 for the predefined time period without releasing footswitch 104, surgeon designates region 746 for auto-focus by positioning designation symbol 744 at region 746 by staring at region 746 and releasing footswitch 104. When the auto-focus is activated by releasing footswitch 104, surgeon 120 designates region 746 for auto-focus by positioning designation symbol 744 at region 746 for a predefined time period, such as 0.5 second. System 100 may tolerate minor movements while designation symbol 744 is positioned at region 746.

Referring to FIG. 7D, computer 118 digitally focuses region 746 designated by designation symbol 744. Comparing region 746 of FIG. 7C before focus with region 746 of FIG. 7D after focus, the results of the digital focus can be seen.

Autofocus may be implemented in various modes. In one mode, once auto-focus has been activated and a focus point has been selected, (i.e. region 746), the auto-focus locks onto the selected region, keeping it in focus until the auto-focus feature is deactivated. This may be useful in applications when the position and orientation of the camera-head changes to capture different parts of the patient's anatomy. As long as the selected region is within the live image feed, it remains in focus.

In another mode, "auto-focus" is a one-time action. Each time the auto-focus feature is activated selecting menu item 720, designation symbol 744 is displayed and surgeon 120 is prompted to designate a region on which to focus. System 100 does not lock onto the designated region, rather focuses the designated region as a one-time action. In this implementation, menu item 720 read "Auto-focus", without stipulating "off" or "on".

Figure 7E:
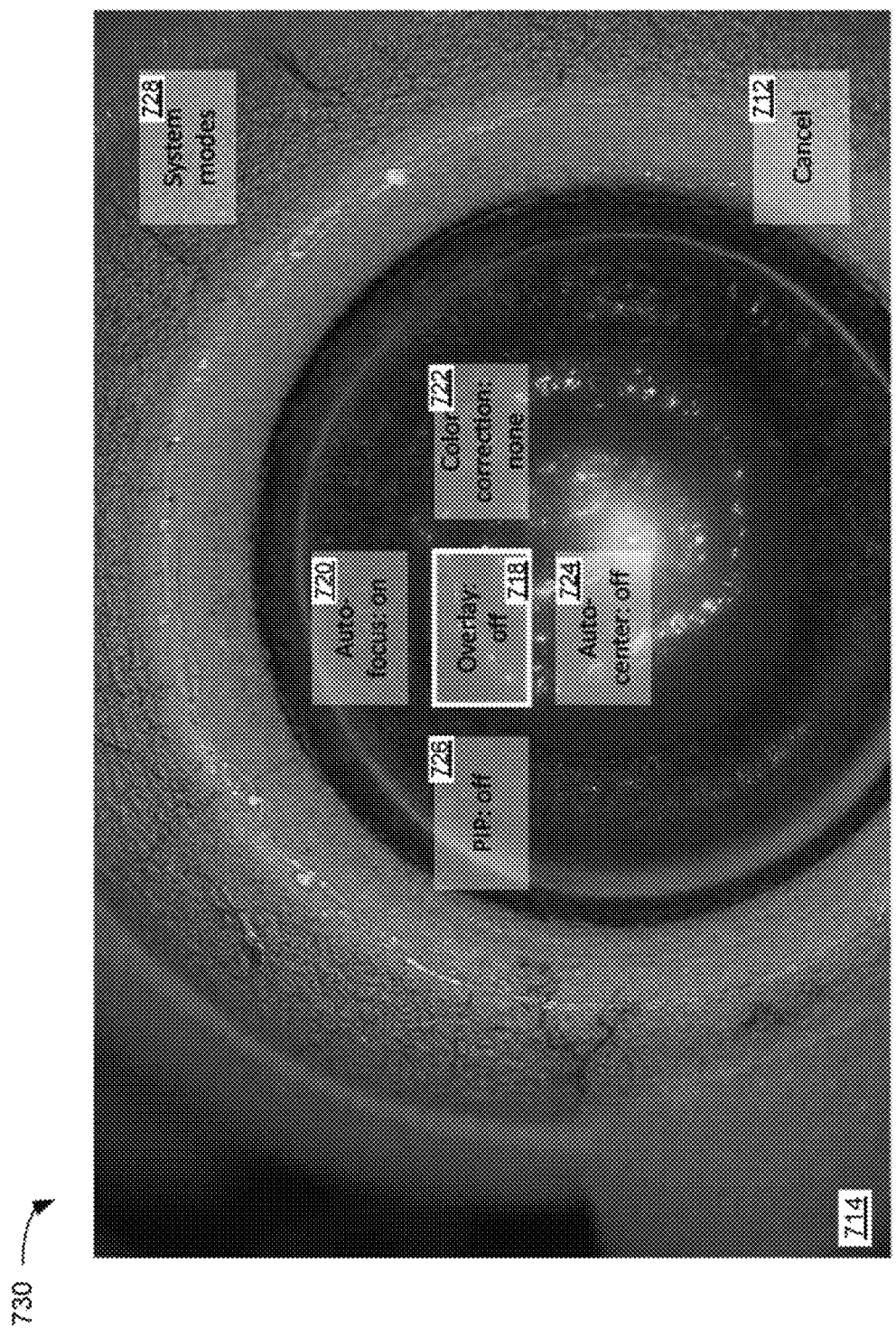
FIG. 7E illustrates another view of the menu of FIG. 7A overlaid on the live image, constructed and operative in accordance with an embodiment of the disclosed technique.

Reference is now made to FIG. 7E, which is another illustration of the menu of FIG. 7A, overlaid on the live image feed, constructed and operative in accordance with an embodiment of the disclosed technique. Menu 730 is one again displayed after being invoked using the techniques described herein. However, this time menu item 720 indicating the auto-focus feature displays "on", indicating that the auto-focus is currently turned on. To switch off the auto-focus, surgeon 120 selects menu item 720, using the techniques described above.

Figure 7F:
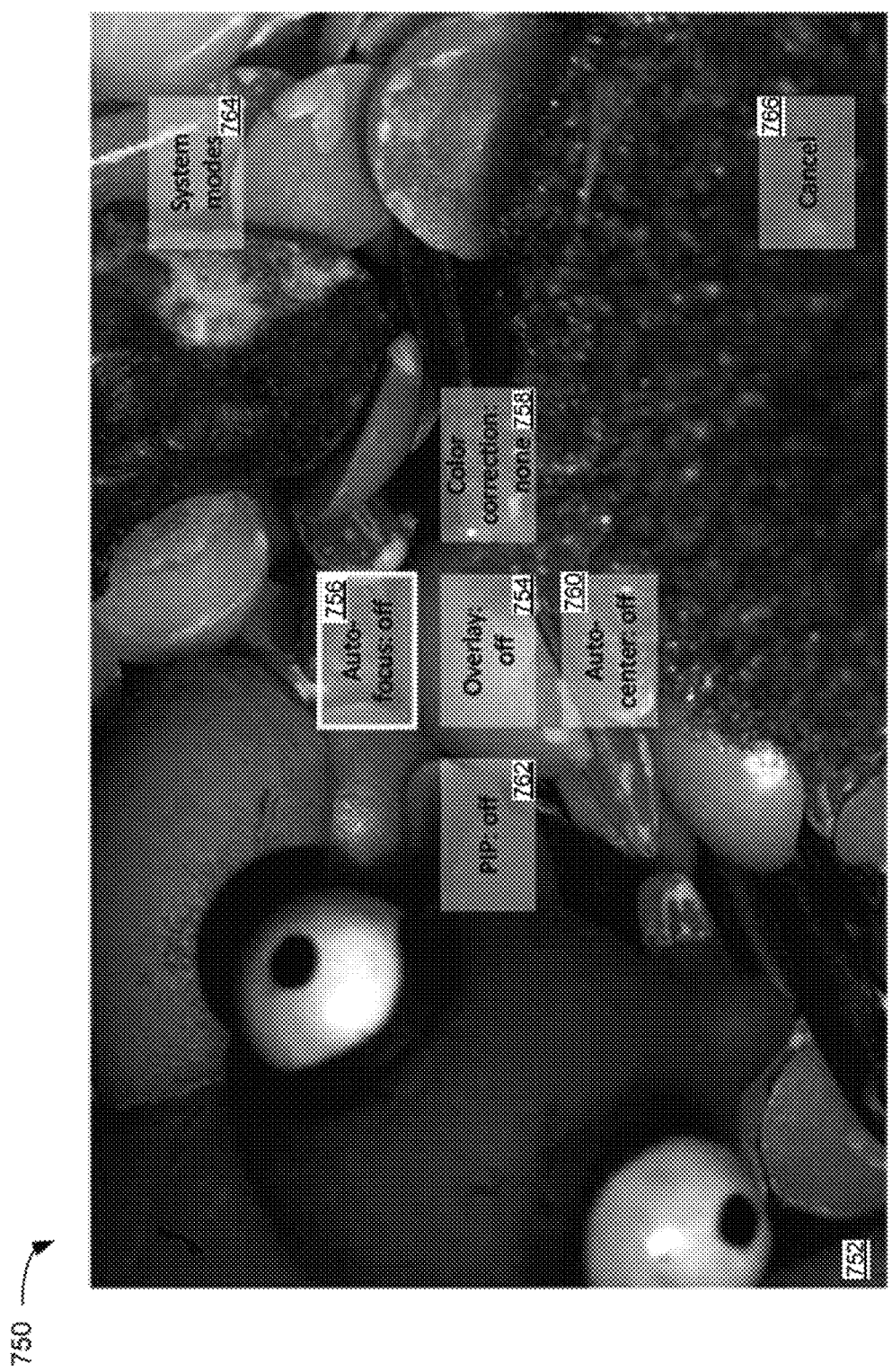
FIGS. 7F-7I, taken together, illustrate another exemplary implementation of a menu-driven user interface for focusing on a selected area of the field of view, constructed and operative in accordance with another embodiment of the disclosed technique.
Figure 7G:
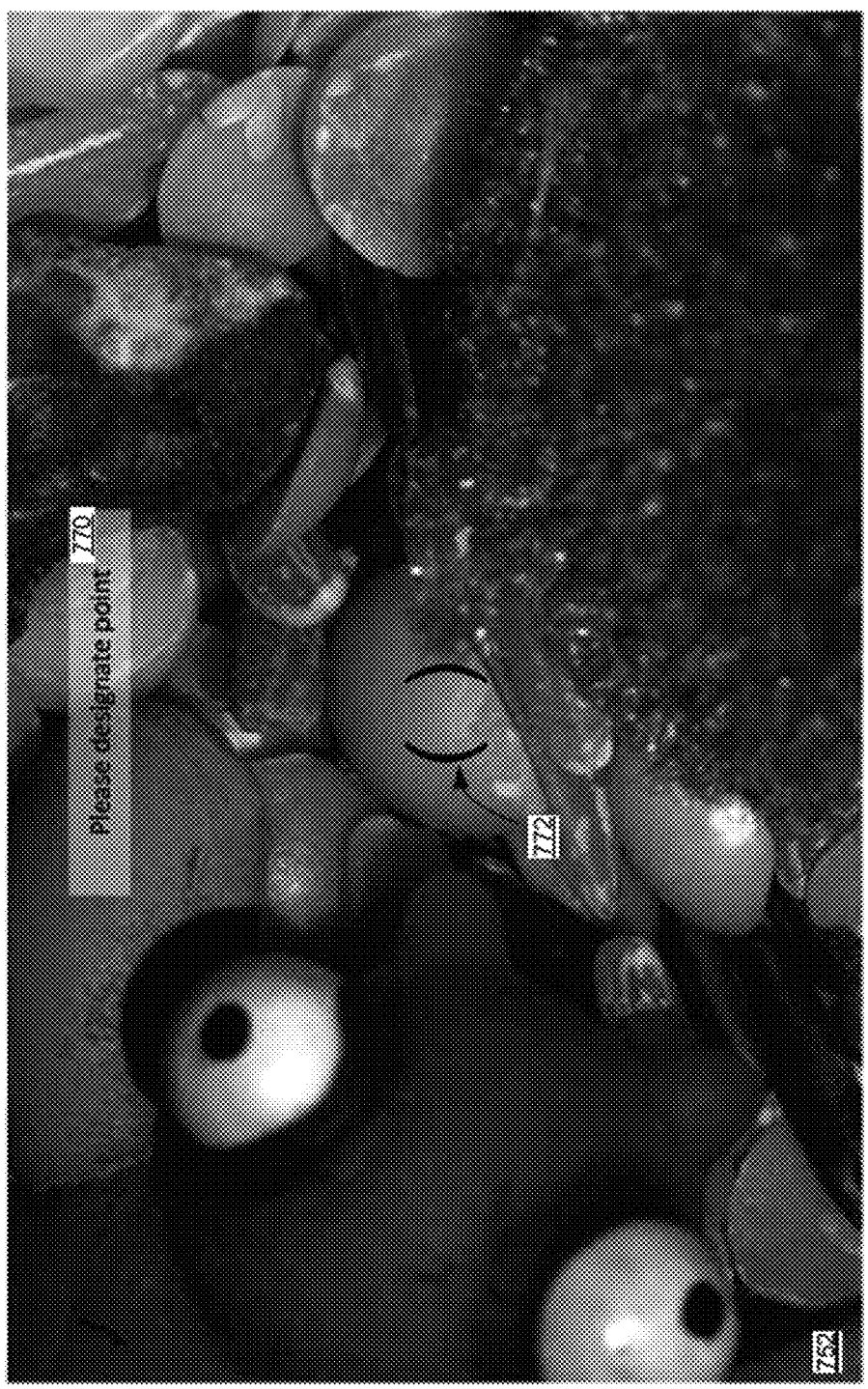
Figure 7H:
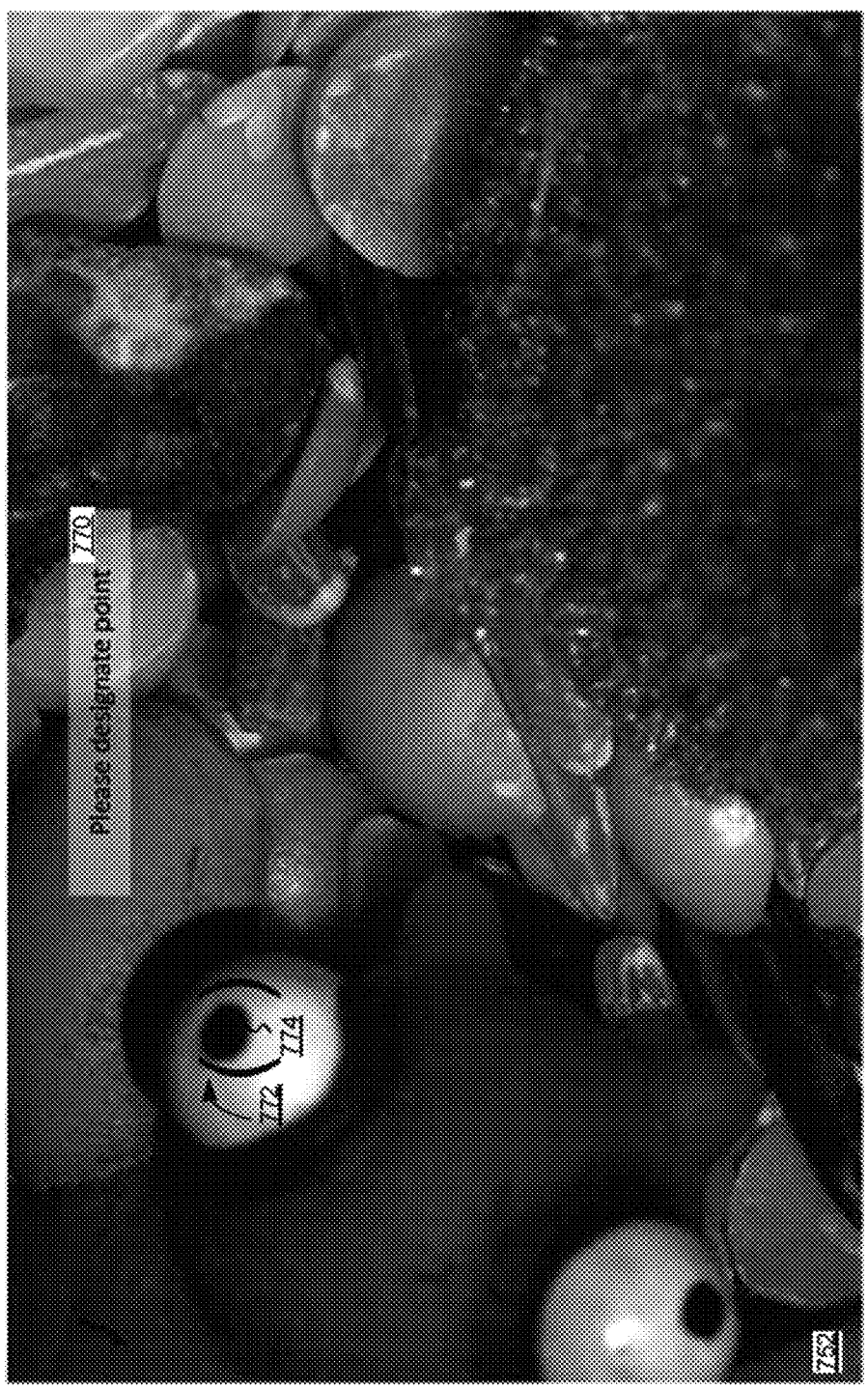
Figure 7I:
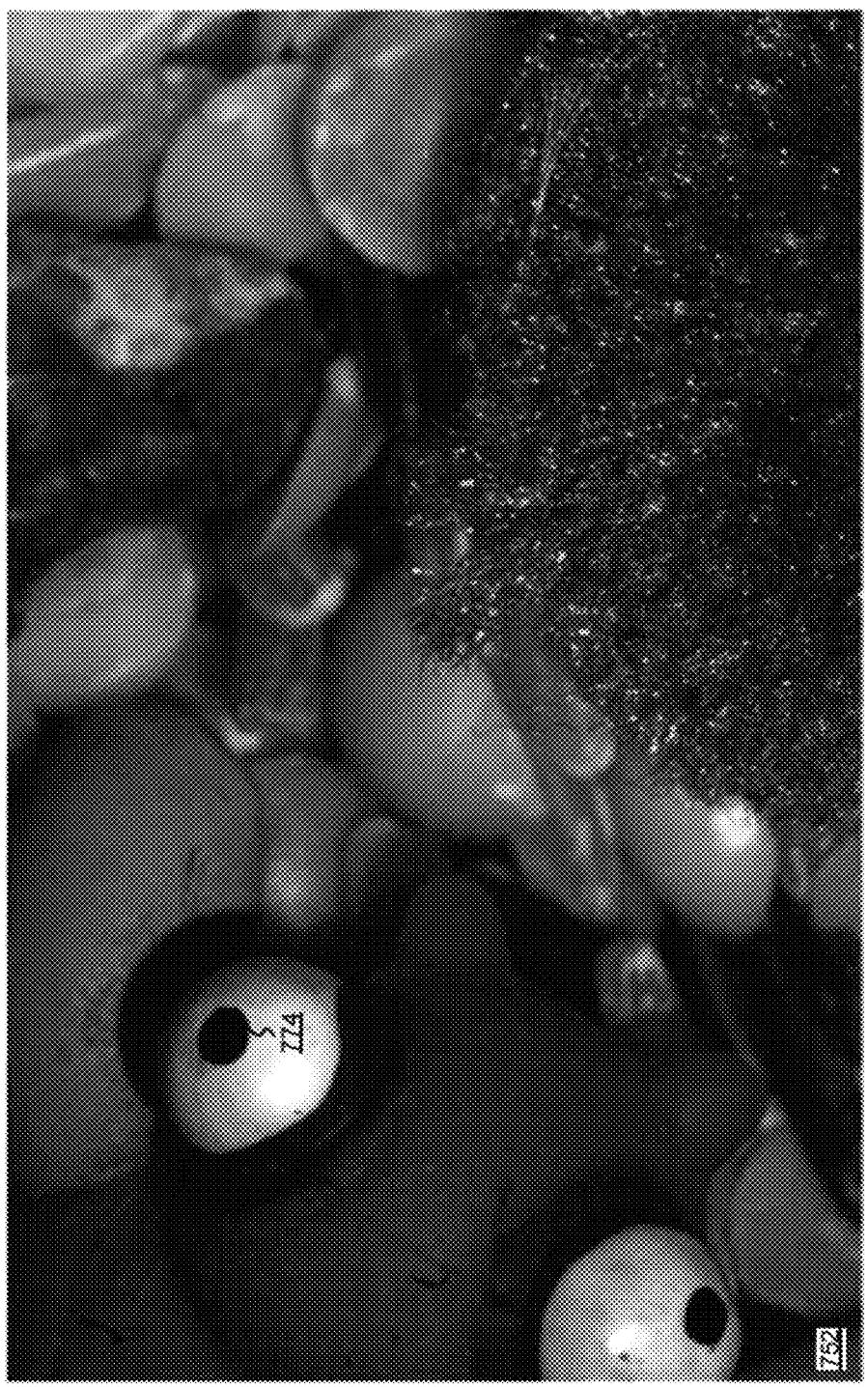

Reference is now made to FIGS. 7F-7I, which, taken together, illustrate another exemplary implementation of a menu-driven user interface for focusing on a selected area of the field of view, constructed and operative in accordance with another embodiment of the disclosed technique. FIGS. 7F-7I are substantially similar to FIGS. 7A-7D described above. Referring to FIG. 7F, a menu 750 is shown overlaid on a live image 752. Menu 750 corresponds to menu 630 of FIG. 6A, and includes menu items: Overlay 754, Auto-focus 756, Color correction 758, Auto-center 760, PIP 762, System modes 764, and Cancel 768. Surgeon 120 turns on the auto-focus via UI 160, as described above. Referring to FIG. 7G, a UI screen 768 is overlaid on live image 752. UI screen 768 displays a prompt 770 and a symbol 772 (e.g. a pair of round brackets). Prompt 770 requests surgeon 120 to designate a focus point on live image 752 by manipulating symbol 772. Referring to FIG. 7H, surgeon 120 moves symbol 772 to designate a feature 774 that is not well focused (e.g. a blurred black circle on a white background). Referring to FIG. 7I, feature 774 of live image 752 is displayed in sharper focus than in FIG. 7H. Surgeon 120 can continue the surgical procedure while viewing feature 774 at a better resolution than before.

System 100 additionally provides for a preplanning phase, allowing surgeon 120 to customize the display of data via HMD 102 to include one or more overlays. Prior to performing the surgical procedure, surgeon 120 may add one or more symbols and notes on the preoperative images. During the surgical procedure, the added symbols and notes are displayed in an overlay that is registered to the live video acquired by camera system 112. For example, marks indicating optimal locations for photocoagulation are displayed, overlaid, and registered to the live image feed. As another example, surgeon 120 colors areas of the preoperative images to create a color map, such as blue for an attached retina, and red for a detached retina. The color map is subsequently overlaid on the live video during the surgical procedure.

System 100 additionally allows surgeon 120 to control the acquisition of snapshots of any live images acquired by camera head 110 throughout the surgical procedure. The snapshots are stored at computer 118. The stored snapshots may be recalled from memory and viewed by surgeon 120 in a separate screen or PIP on display module 130 at a later stage of the surgical procedure, to monitor the progress or for assisting in guidance. The snapshots may be stored in 2D or 3D format. The snapshots may also be stored as a short video clip, or "GIF" format, that is repeatedly rendered on display module 130 in a PIP. This GIF format is advantageous for viewing membranes. When in PIP mode (i.e. after "selecting" the PIP), activating snapshot may save the PIP image only. This may be useful for saving an iOCT image or an endoscope image displayed in PIP.

For example, a snapshot may be taken after a dye was administered to enhance a membrane. Even after the dye has been absorbed and disappears, surgeon 120 can still see the dyed areas in the PIP displayed alongside the live video feed. Since the snapshot is registered to the live video, surgeon 120 can designate points in the PIP as described above, and corresponding points in the live video are automatically highlighted, colored, or marked by a symbol.

The disclosed technique additionally allows surgeon 120 to create a GIF. Surgeon 120 starts recording the images acquired by camera head 110, such as by using pedal 104 in conjunction with a head gesture, and uses a similar set of UI inputs to stop the recording. For example, system 100 displays a GIF menu item (not shown) that when selected, causes system 100 to record images for the GIF. To select the GIF menu item, surgeon 120 gazes at the GIF menu item for a predefined time period, such as 2 seconds while pressing footswitch 104. To terminate the recording of images for the GIF, surgeon 120 releases footswitch 104. Surgeon 120 assigns a name, either by head gesturing to a menu item listing identifying details, such as a timestamp with the identity of patient 122, or alternatively through voice control. In some embodiments, system 100 automatically assigns a name to the snapshot or GIF, using known techniques. The GIF is stored to memory 118D (FIG. 1B), and may be subsequently recalled and displayed in a separate screen, or in a PIP by selecting a menu item, accordingly.

When system 100 is activated, surgeon 120 may manually position camera head 110 close to the designed location with the aid of coaxial/red-eye illumination beams that overlap around the patient's eye only when camera head 110 is correctly positioned. Surgeon 120 may then instruct the system to automatically fine-tune the position of camera head 110 to the correct working distance. Computer 118 automatically brings high res cameras 140A and 140B to the appropriate height above the area of interest of surgical field 124, i.e. mechanical arm controller 118G manipulates the z-axis motor, camera system controller 118H manipulates the XY-motors to center the patient's eye in the image and sets the lenses of cameras 140A and 140B to nominal shutter, focus, and zoom values, and illumination system controller 118I controls the illumination system 114 to anterior-eye settings.

System 100 can be configured to save system settings for subsequent use. After the surgical procedure is completed, surgeon 120 may edit the system settings via a touchscreen 108 and name the settings for future use. The setting may override the "Default settings", or may subsequently appear as a menu item displayed via a menu on HMD 102. Touchscreen 108 allows surgeon 120 to choose any saved settings subsequently displayed via HMD 102.

In some embodiments, system 100 identifies surgeon 120 when donning HMD 102. The user, such as surgeon 120, or alternatively a nurse may select surgeon 120 from an existing list of surgeons, where each surgeon in the list is associated with a set of pre-configured settings, as described above. System 100 may automatically identify surgeon 120 using any suitable technique, such as voice recognition, or using biometric data, such as by using an eye-tracker camera integrated within HMD 120 to compare acquired images of the eye of surgeon 120 with previously acquired images. Once surgeon 120 has been correctly identified, system 100 is configured with the pre-configured settings associated with surgeon 120.

Similarly, in some embodiments, system 100 automatically comparing the real-time images of the eye of patient 122 with pre-operative images acquired (assumedly) of patient 122 to verify that patient 122 corresponds to the surgical procedure planned. For example, to eliminate errors and verify that the preoperative data that the surgeon is using belongs to patient 122, and that the correct surgical procedure is being performed, and on the correct eye. System 100 alerts surgeon 120 of any disparity between the pre-operative data being used and the live image stream acquired of patient 122.

In some embodiments, system 100 displays a checklist to surgeon 120 at any of: the beginning, throughout, or the end of the surgical procedure. Surgeon 120 may manually check off items from the checklist as these are actions executed, or system 100 may detect execution of these actions, and check the items off the list automatically. The checklist may be customized for each surgeon, and may be displayed on identifying surgeon 120, as described above. The checklist may be displayed in a side screen or as a PIP in the real time image, and the surgeon may choose to turn it on or off. In some embodiments, computer 118 (FIG. 1B) displays a centering symbol via HMD 102 to assist surgeon 120 to correctly position HMD 102 to allow surgeon 120 to view the entire FOV. For example, the centering symbol may be a frame, or other suitable symbol that indicates the borders of the FOV. The symbol may be displayed automatically when surgeon 120 first dons HMD 102, as detected by the HMD tracker when the HMD is moved after being still, or per user command (via any UI method), if HMD 102 moves or becomes misaligned. If HMD 102 comprises a capability to change the inter-pupillary distance (IPD) of the display, this feature may also to assist in verifying that it was set correctly, and adjust it as necessary.

In some embodiments, system 100 detects and corrects for effects related to non-overlapping images in a 3D digital microscope. The problem arises when the cameras capture an object that is not at the designed working distance, and the surgeon sets the focus using the lenses focus motors. When this occurs, the images that are generated by the two cameras 140A and 140B (FIG. 1E) are not completely overlapping. If these images are streamed to the two eyes of surgeon 120 via displays 130A and 130B (FIG. 1C) it may cause eye strain. The overlapping parts of the images are not displayed as though they are coming from the same direction in space. In order for his brain to merge the two images to a single 3D image, surgeon 120 must squint.

This situation can be detected automatically, for instance by using image processing to calculate the boundaries of the overlapping parts of the two 2D images, or by using calibration data to derive the actual working distance from the state of the focus motors. Each camera lens focus-motor state has a corresponding pre-calibrated working distance. By comparing the actual working distance with the designed working distance this discrepancy can be calculated and accounted for.

One solution is to shift the two images and fill the missing parts of the images with black bars. This way both eyes of surgeon 120 see the overlapping parts of the images as originating from the same direction, and the two edges of the FOV, which are not overlapping, are seen each by one eye only (note that when the displayed image comprises a black area the display unit doesn't emit any light at the corresponding area of the display).

Figure 8B:
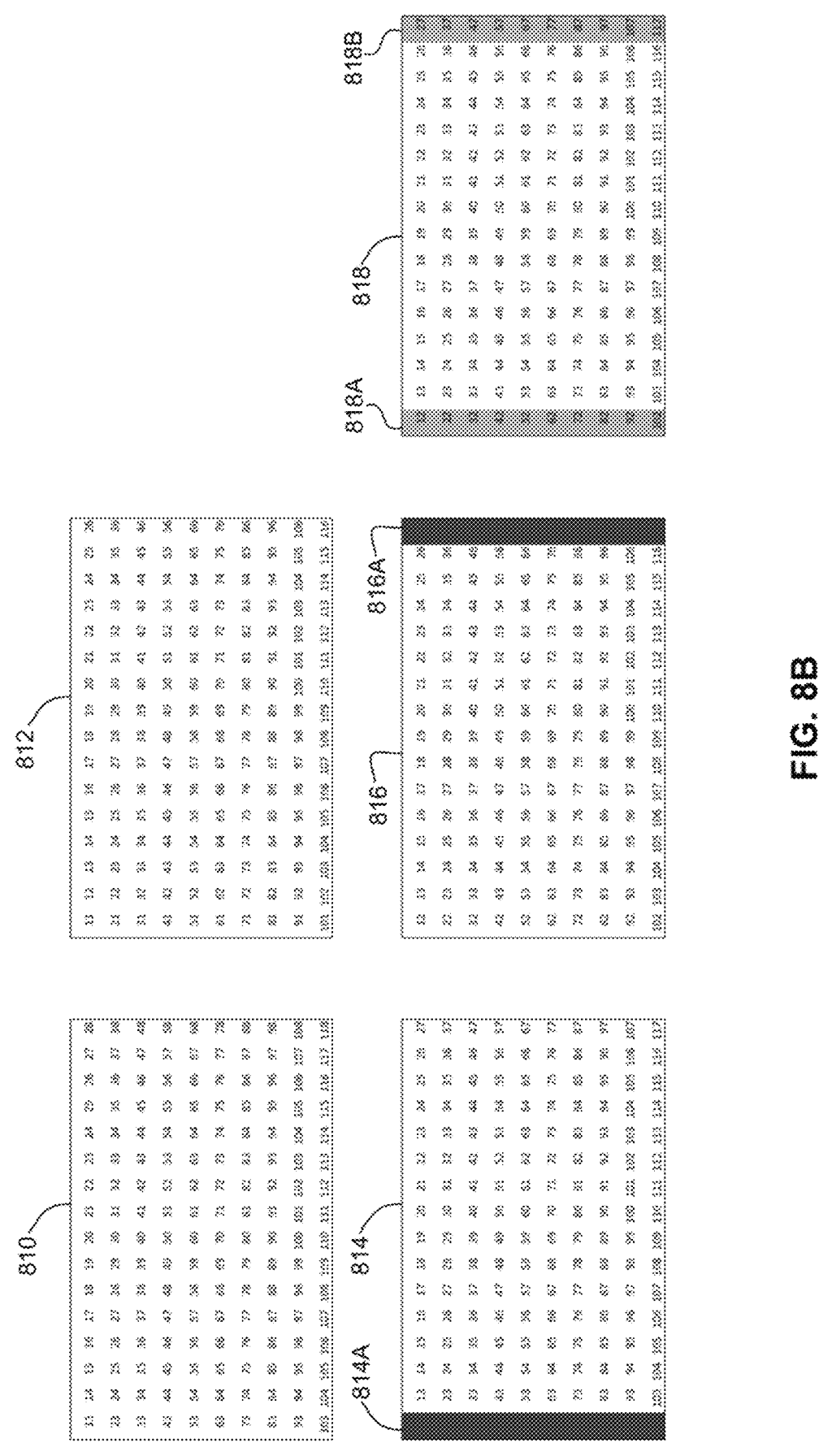

Reference is now made to FIGS. 8A-8B, which taken together, show a technique for correcting effects related to non-overlapping images caused by a discrepancy between the actual working distance and designed working distance of the cameras, constructed and operative in accordance with the disclosed technique. FIG. 8A shows an optical setup 800, indicating a discrepancy between the actual working distance 802 and the designed working distance 804. As a result of the discrepancy, the images acquired by cameras 140A and 140B (FIG. 1E), represented by lines 28 and 11, respectively, are shifted and do not completely overlap, such that the images appear as though they originate from different directions.

Referring to FIG. 8B, the shift of the images acquired by cameras 140A and 140B, and the results of the correction are shown. Grid 810 shows a numerical depiction of the image acquired by camera 140A, displayed to the left eye of surgeon 120 and grid 812 shows a numerical depiction of the image acquired by camera 140B, displayed to the right eye of surgeon 120. The two rightmost columns of grid 810 are not included in grid 812, and the two leftmost columns of grid 812 are not included in grid 810, resulting from the discrepancy between the actual working distance and the designed distance for cameras 140A and 140B. Referring back to FIG. 8A, the endpoint of the line corresponding to the image acquired by camera 140A, labelled 28, and which does not overlap with the line corresponding to the image acquired by camera 140B, corresponds to the top rightmost corner of grid 810 which is not included in grid 812. The endpoint of the line corresponding to the image acquired by camera 140B, labelled 11, and which does not overlap with the line corresponding to the image acquired by camera 140A, corresponds to the top leftmost corner of grid 812 which is not included in grid 810.

To correct for this discrepancy, grid 810 is shifted to the right by one column, indicated as grid 814, and grid 812 is shifted to the left by one column, indicated as grid 816. The leftmost column 814A of grid 814 is blacked out as this part of the image will not be displayed to surgeon 120, and the rightmost column 816A of grid 816 is blacked out as this part of the image will not be displayed to surgeon 120. Grid 818 shows the overlapping features of both grid 810 and 812 in the center (white background) seen by both eyes of surgeon 120. The leftmost column 818A, indicated with the gray background is only seen by the right eye of surgeon 120, and the rightmost most column 818B, indicated with the gray background is seen only by the left eye of surgeon 120.

The shifting technique described above may be performed continuously while the focus of cameras 140A and 140B is adjusted. Alternatively, the shifting technique may be performed only once the focus adjustment is complete, e.g. once the enable pedal of footswitch 104 is released. In this case, the shifting technique is performed gradually over a short period of time, e.g. a few seconds, such that surgeon 120 does not experience an abrupt change in the displayed image. Surgeon 120 may switch on or off the shifting technique and may set its duration via UI 160. Note that in the example of FIG. 8B the combined image has the same magnification factor as each of the separate images. However, this is not mandatory, and the magnification could be reduced somewhat, such that the combined image, represented by grid 818, comprises the entire imaged FOV. For example, the numerical representation of the combined image would have included all the columns of each acquired image, and the leftmost column would correspond to the leftmost column of grid 812 (with the number 11 as the top, leftmost grid entry) and the rightmost column would correspond to the rightmost column of grid 810 (with the number 28 as the topmost grid entry). Effectively if this option is applied, when the user changes the focus, the zoom also changes slightly.

The non-overlapping images can occur in several scenarios. One such scenario that requires correcting using the shifting technique is in the beginning of the procedure when surgeon 120 positions camera head 110 at approximately the designed working distance. Surgeon 120 may manually adjust the height of cameras 140A and 140B housed in camera head 110 above the surgical site until two spots of light generated by the two flood lights of illumination system 114 overlap. These lights may be designed to overlap at the designed working distance. If camera head 110 is not perfectly positioned at the designed working distance, the images generated by cameras 140A and 140B, and projected to the two eyes of surgeon 120 via displays 130A and 130B do not completely overlap, as illustrated above in FIG. 8B.

Figure 8D:
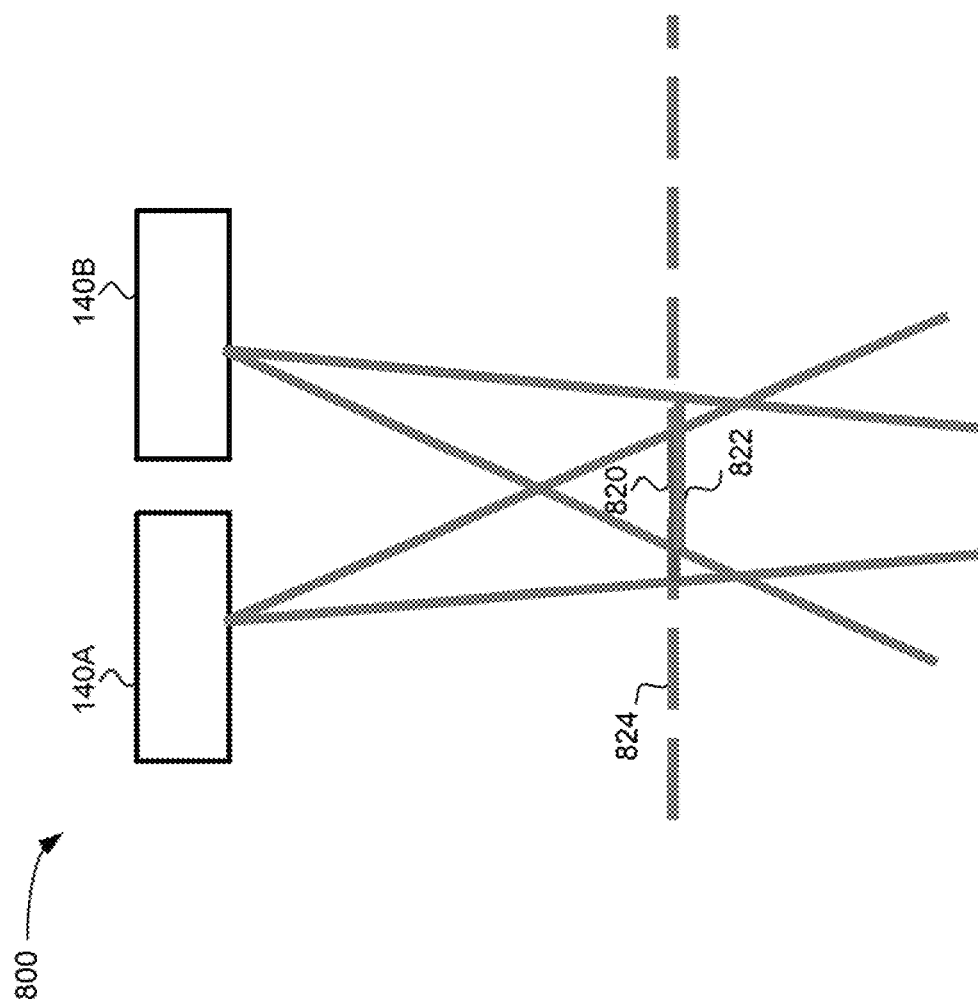

Reference is now made to FIG. 8C-8E which, taken together, illustrate optical system 800 of FIG. 8A at different working distances, constructed and operative in accordance with an embodiment of the disclosed technique. The top line 820 of FIGS. 8C-8E illustrates the image captured by left camera 140A (FIG. 1E) and displayed by display 130A (FIG. 1C) and the bottom line 822 of FIGS. 8C-8E illustrates the image captured by right camera 140B (FIG. 1E) and displayed by display 130B (FIG. 1C). Dashed line 824 of FIGS. 8C-8E indicates the object plane. The error in positioning of cameras 140A and 140B has been exaggerated for the illustration. FIG. 8C shows optical system 800 with the cameras positioned at the designed working distance. Consequently, there is no discrepancy between the actual and designed working distances. The images acquired from this configuration do not require shifting as they completely overlap, as indicated by overlapping lines 820 and 822.

Referring to FIG. 8D, optical system 800 is shown with cameras 140A and 140B (FIG. 1E) positioned below the designed working distance, resulting in a discrepancy between the actual working distance and the designed working distance. A consequence of this discrepancy is that the images acquired by each of cameras 140A and 140B and displayed via displays 130A and 130B, respectively, do not completely overlap. Line 820, indicating the image acquired by left camera 140A and displayed by display 130A, does not completely overlap with line 822, indicating the image acquired by right camera 140B and displayed via display 130B. As a result, the overlapping parts in the two images appear as originating from different directions, and the user's left and right eyes squint in an effort to generate a combined 3D image in the brain. This may cause eye strain, unless the images are corrected, such as by using the shifting technique described above.

Referring to FIG. 8E, optical system 800 is shown with cameras 140A and 140B positioned above the designed working distance, resulting in a discrepancy between the actual working distance and the designed working distance. A consequence of this discrepancy is that the images acquired by each of cameras 140A and 140B do not completely overlap. Line 820, indicating the image acquired by left camera 140A and displayed via display 130A, does not overlap with line 822, indicating the image acquired by right camera 140B and displayed via display 130B. As above, without applying the shifting technique, the left and right eyes will squint in an effort to generate a combined 3D image in the brain, causing eye strain.

In some embodiments, such as when system 100 includes a z-axis motor to control the height of camera head 110, UI 160 presents an initializing option, i.e. "Init" or "Home" menu item, to automatically adjust the height of camera head 110 to the designed working distance. In embodiments where system 100 is not configured with a Z motor to control the height of camera head 110, computer applies image processing techniques to determine the discrepancy between the actual and designed working distance, and notifies surgeon 120 to manually adjust the distance if the discrepancy is larger than an allowed threshold. For example, UI 160 displays a message guiding surgeon 120 to adjust the height either up or down, and by how much, i.e. in centimeters or inches. Note, however, that surgeon 120 may choose to continue working at a distance different from the designed working distance, for instance for increasing the imaged FOV (the downside being not seeing in 3D in all the FOV, but only where the images overlap).

Another scenario that requires correcting using the shifting technique is in when surgeon 120 uses the lens focus motors integrated with cameras 140A and 140B to change the focus plane, while cameras 140A and 140B are properly positioned at the designed working distance. For example, when surgeon 120 switches between the anterior and posterior modes, or focuses on different planes within the same mode, a discrepancy between the images acquired by camera 140A and 140B may be sufficiently large to cause eye strain. In such a case, the shifting technique described above may be applied to align the images acquired by camera 140A and 140B and reduce eye strain experienced by surgeon 120.

Reference is now made to FIG. 8F which illustrates optical system 800 of FIG. 8A configured to focus on two different focus planes 830 and 832, constructed and operative in accordance with an embodiment of the disclosed technique. The designed working distance is indicated by dashed line 834. Focus plane 830 is positioned above the designed working distance 834, and focus plane 832 is positioned beneath designed working distance 834. The top line 836 represents the image captured by left camera 140A and displayed via display 130A, and the bottom line 838 represents the image captured by right camera 140B and displayed via display 130B. Top line 836 is shown shifted to the left relative to bottom line 838, indicating a discrepancy between the two acquired images, which can be corrected using the shifting technique described herein. Similarly at focus plane 832, the top line 840 represents the image captured by left camera 140A and displayed via display 130A, and the bottom line 842 represents the image captured by right camera 140B and displayed via display 130B. Top line 840 is shown shifted to the right relative to bottom line 842, indicating a discrepancy between the two acquired images when cameras 140A and 140B are adjusted to focus plane 832. This discrepancy can also be corrected using the shifting technique described herein.

In the embodiments describes herein above, the shifting was performed to allow for comfortable stereoscopic vision when both eyes of the surgeon are gazing forward. In some embodiments, system 100 may be configured to intentionally generate a discrepancy between the two displayed images. The amount of shift may be tailored specifically to each user of system 100. The displayed images may be shifted horizontally, vertically, or both. The shifts may be unique for each of the surgeon's eyes. This shifting feature may be useful for decreasing eye strain in a surgeon who experiences phoria (i.e. a misalignment of the eyes). The amount and direction of the shifting may be configured to change as a function of head orientation (as indicated by the tracker) for phoria cases that depend on head orientation.

Figure 8G:
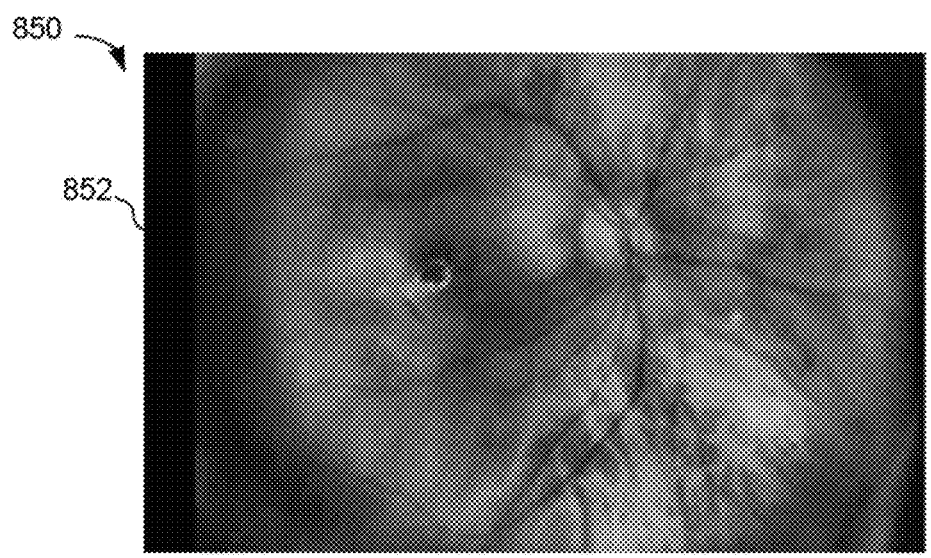
FIGS. 8G-8I, taken together, illustrate images displayed via an HMD after applying the shifting technique described according to FIGS. 8A-8B, constructed and operative in accordance with an embodiment of the disclosed technique.
Figure 8H:
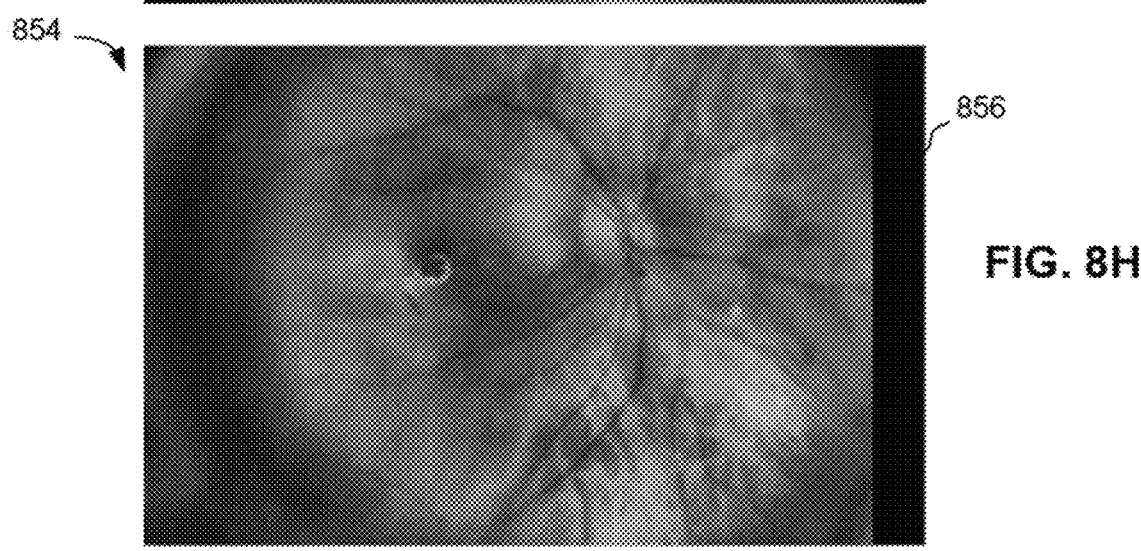
Figure 8I:
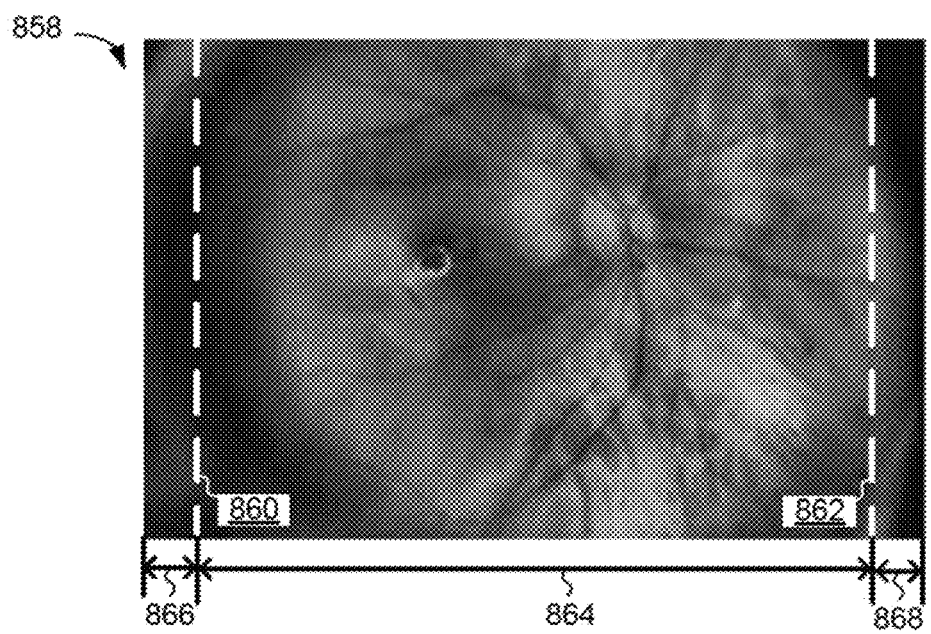

In some embodiments, the user-specific shifting may be configured during a one-time calibration process, and may be saved per user so that it is automatically implemented for subsequent uses of system 100. Optionally the surgeon may adjust the shifting characteristics during the surgical procedure. Optionally, head orientation-based shifting is performed gradually and only after a predetermined period of time in which the head orientation of the wearer of HMD 102 has not changed. This is to prevent shifting of displayed images in response to performing a head gesture for enabling other functionalities, and which may be disturbing for some users. In some cases, the displayed images may be shifted in a non-uniform manner to correct for a possible phoria dependency in the gaze direction (e.g. the vertical gaze direction). For example when the phoria depends on the vertical gaze direction, the shifting may change continuously (and not necessarily linearly) from the top of the image to the bottom. Optionally, if HMD 102 enables changing the focus of the HMD optics, the amount and direction of the shifting may depend on the focus. Note that focus-dependent shifting may be implemented also for users that do not manifest phoria. The shifting described above may also generate a binocular rivalry effect that might require correction, as described herein below. Reference is now made to FIGS. 8G-8I, which illustrate images displayed via HMD 102, after applying the shifting technique described herein. The effect of the shifting has been exaggerated for the purpose of clarity. FIG. 8G shows a 2D live image 850 acquired by camera 140A. 2D live image 850 has been shifted to the right according to the shifting technique described herein, as indicated by a black border 852 displayed on the left edge of live image 850. FIG. 8H shows a 2D live image 854 acquired by cameras 140B. 2D live image 854 that has been shifted to the left according to the technique described herein, as indicated by a black border 856 displayed on the right edge of live image 854.

When the amount of shifting executed by the shifting technique is significant, a binocular rivalry effect may arise. Referring to FIG. 8I, a representation of a 3D live image 858 is shown. Image 858 is a combination of 2D live image 850 of FIG. 8G and 2D live image 854 of FIG. 8H. Range 864 indicates the portion of image 858 created from both of images 850 and 854, and displayed by both of displays 130A and 130B, respectively. Range 866 of image 858 indicates the portion of image 858 created only from image 854 and displayed only by display 130B, and range 868 of image 858 indicates the portion of image 858 created only from image 850, and displayed only by display 130A. The brain corrects for black borders 852 and 856 of images 850 and 854, respectively, causing surgeon 120 to see a stark contrast in brightness at the area delineated by dashed lines 860 and 862, where the brightness of image 858 drops abruptly by half. Whereas the middle area of image 858 (range 864) is displayed by both displays 130A and 130B, the left edge of image 858 (range 866) is displayed only by display 130B, and the right edge of image 858 (range 868) is displayed only by display 130A. One solution is to gradually reduce the brightness of both images 850 and 854 in the areas that are near the "missing edges", i.e. 852 and 856, respectively, eliminating the stark contrast in brightness at the area delineated by lines 866 and 868. The reduction in brightness may follow a non-linear gradient, as a linear gradient may be detectable by the brain.

Figure 9:
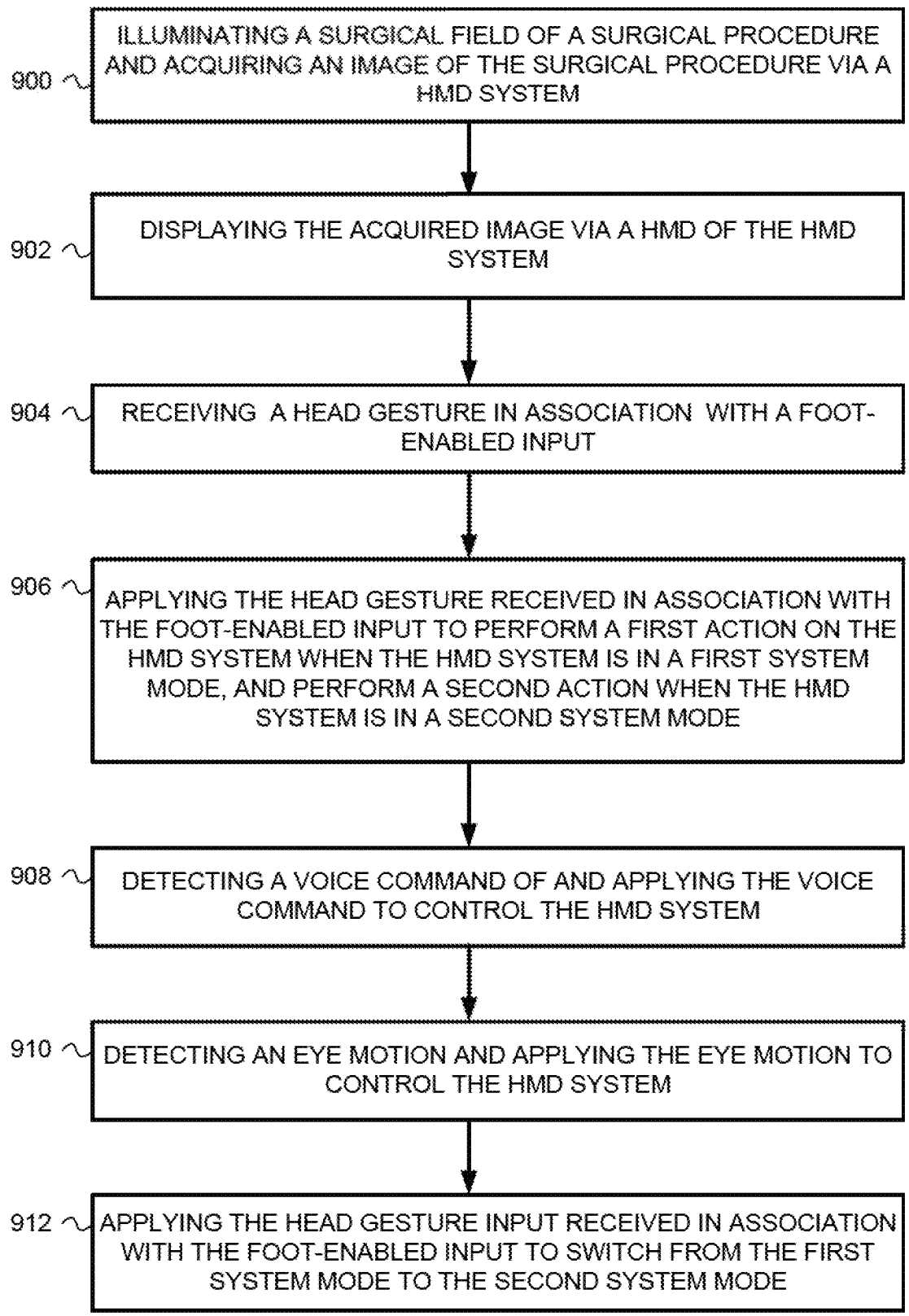
FIG. 9 is a schematic illustration of a method for controlling a heads up display system, constructed and operative in accordance with another embodiment of the disclosed technique.

Reference is now made to FIG. 9, which is a schematic illustration of a method for controlling a heads up display system, constructed and operative in accordance with another embodiment of the disclosed technique.

In procedure 900, a surgical field of a surgical procedure is illuminated, and at least one image of the illuminated surgical procedure is acquired. With reference to FIG. 1A, illumination system 114 of head mounted display system 100 illuminates surgical field 124. Camera system 112 acquires at least one image of illuminated surgical field 124.

In procedure 902, at least one image relating to the surgical procedure is displayed to a surgeon via a head mounted display. The image may be any of: the at least one image acquired via camera system 112 and displayed in real-time, a pre-operative image acquired earlier, or an image relating to UI 160, such as a menu, an overlay, and the like. With reference to FIG. 1A, the at least one image is displayed on head mounted display 102.

In procedure 904, a head gesture input is received in association with a foot motion input. With reference to FIG. 2A, head tracker 162 receives a head gesture input by surgeon 120 (FIG. 1A) and footswitch 104 receives a foot motion input from surgeon 120. Computer 118 receives the head gesture input in association with the foot motion input.

In procedure 906, the head gesture input received in association with the foot motion input are applied to perform a first action on a head mounted display system when the head mounted display system is in a first system mode, and perform a second action on the head mounted display system when the head mounted display system is in a second system mode. With reference to FIG. 2B, computer 118 applies the head gesture input received in association with the foot motion input to perform a zoom-out action 240 when the system mode is Normal, and performs a scroll action 242 when the system mode is set to Pre-op.

In some embodiments, the first said second actions comprise any of: controlling a shutter coupled to a display module of the head mounted display, where the display module is at least partially transparent where the shutter is open and the display module is substantially opaque where the shutter is closed. With reference to FIG. 1C, shutter 132 is configured with display module 130 of head mounted display 102.

In other embodiments, the first and second action comprises any of: controlling the image displayed via the head mounted display, controlling the camera system, controlling the illumination system, controlling the camera head positioner. With reference to FIG. 2A, computer 118 (FIG. 1B) applies the input received via UI-input 160A to control a component of UI-output 160B, i.e. computer 118 controls one or more of camera system 112, illumination system 114, the image displayed via HMD 102 on display module 130, and one of camera head positioner 111 or a robotic arm.

In some embodiments controlling the image displayed via the head mounted display comprises any of: selecting the image from the group consisting of: a live feed video, a VGS video, and a preoperative iOCT video, zooming in and zooming out, scrolling between at least two virtual screens, displaying a picture in picture (PIP), displaying an overlay on a live image, centering the image, displaying a menu, navigating a menu, and controlling a region of interest of the image. Properties of the image displayed via the head mounted display may be controlled according to any suitable technique, such as digitally or optically.

In some embodiments controlling the camera system comprises controlling one or more optical or electrical characteristics of the camera system. For example, a camera for acquiring the image may be selected, and a position and orientation of the camera system may be controlled. With reference to FIG. 1E, computer 118 (FIG. 1B) selects any of high resolution cameras 140A and 140B, IR camera 148, and iOCT scanner 142. With reference to FIG. 1A, computer 118 controls the position and orientation of camera system 112 via camera head positioner 111.

In some embodiments, controlling the illumination system comprises any of: electing at least one of multiple illuminators, selecting an intensity setting, selecting a filter, and controlling a position and orientation of said illumination system. With reference to FIG. 1F, computer 118 (FIG. 1B) selects any of white flood light 150, IR flood light 152, and coaxial lights 154A and 154B. With reference to FIG. 1A, computer 118 controls the position and orientation of illumination system 114 via camera head positioner 111.

In procedure 908, a voice command by the surgeon is detected. The voice command is applied to control the head mounted display system. With reference to FIG. 1D, computer 118 (FIG. 1B) receives a voice command by surgeon 120 (FIG. 1A) via microphone 138. Computer 118 applied the voice command to control head mounted display system 100.

In procedure 910, an eye motion by the surgeon is detected, and the eye motion is applied to control the head mounted display system. With reference to FIG. 1C, eye tracking components 136 track an eye motion of surgeon 120 and provide the eye motion to computer 118 (FIG. 1B) via transceivers 102B and 118B.

In procedure 912, the head gesture input is applied to switch from the first system mode to the second system mode. With reference to FIGS. 2A-2B, computer 118 applies the head gesture input received via UI-input 160A to switch to the Vital system mode 244. In some embodiments, computer 118 applies the head gesture input received in association with the foot motion input to switch modes.

In some embodiments, the image is displayed via the head mounted display in a display stabilized state when the head mounted display system is in the first system mode. The image is displayed via the head mounted display in one of multiple virtual screens in a world stabilized state when the head mounted display system is in the second system mode, and the second action scrolls between the multiple virtual screens. With reference to FIG. 5A, the display stabilized state is shown. The video displayed to surgeon 120 is unchanged as he moves his gaze from forward (500) to 30 degrees left (502). With reference to FIG. 5B, the world stabilized state is shown. The video displayed to surgeon 120 changes as he moves his gaze from 5 degrees to the right (504) to 25 degrees to the right (506). The content filling the field of view shifts, as though the virtual screens were fixed objects in the operating room.

In some embodiments, a first region of a field of view of the head mounted display corresponds to the first system mode, and a second region of the field of view of the head mounted display corresponds to the second system mode. The head gesture input applied to switch from the first system mode to the second system mode aligns a line of sight of the surgeon with the second region. With reference to FIG. 3A, region 302 in the center of the field of view corresponds to the Normal system mode, and region 306, to the left of region 302 corresponds to the Pre-op system mode. Surgeon 120 can switch the system mode by moving his line of sight from region 302 to region 306.

In some embodiments, a menu is displayed overlaid on the image displayed on the head mounted display. The menu displays a first menu item for the first system mode on a first region of a field of view of the head mounted display and displays a second menu item for the second system mode overlaid on a second region of the field of view of the head mounted display. The head gesture input applied to switch from the first system mode to the second system mode aligns a line of sight of the surgeon with said second menu item. With reference to FIGS. 4A-4C, menu 400 is shown overlaid on a video of the surgical procedure. Menu 400 includes multiple menu items 402, 404, 406, 408, 410, and 412. Surgeon 120 can switch the system mode by moving his line of sight between the menu items, e.g. from menu item 402 highlighted in FIG. 4A, to menu item 410, highlighted in FIG. 4B.

It will be appreciated by persons skilled in the art that the disclosed technique is not limited to what has been particularly shown and described hereinabove. Rather the scope of the disclosed technique is defined only by the claims, which follow.

The invention claimed is:

1. A head mounted display system, for use in a surgical application employing a camera system for providing an image of a surgical field, said head mounted display system allowing for a user to switch between different system modes using at least one head gesture, the system comprising:
a head mounted display (HMD) configured to be worn by a surgeon;
a tracker configured to track head gesture inputs by said surgeon; and
a computer coupled to said HMD, said tracker and said camera system and configured to:
receive a head gesture input from said tracker; and
apply said received head gesture input to switch a system mode of said head mounted display system from a first system mode to a second system mode, wherein at least one of said first system mode and said second system mode comprises displaying at least part of said image of said surgical field from said camera system to said surgeon via said HMD; and
wherein said at least part of said image is a magnified image of said surgical field.

2. The head mounted display system according to claim 1, wherein said first system mode and said second system mode is selected from the group consisting of:
a normal mode for displaying said at least part of said image from said camera system via said HMD;
an inverted mode for enabling said surgeon to view said surgical field in an inverted view;
a first external video mode for displaying an image of said surgical field from a first external camera, said first external camera being external to said head mounted display system and also to said camera system;
a second external video mode for displaying an image from a second external camera, said second external camera being external to an operating room wherein said surgical application is being executed;
a visor-guided surgery (VGS) mode for enabling said surgeon to see an augmented real world view of said surgical field;
a pre-operative mode for enabling said surgeon to view pre-operative data related to a surgical procedure of said surgical application;
an intraoperative mode for enabling said surgeon to view intraoperative data related to said surgical procedure from at least one first external device;
a picture-in-picture (PIP) mode for enabling said surgeon to view at least one of said at least part of said image, said pre-operative data, said image from said first external camera, said image from said second external camera, a previously acquired snapshot of said at least part of said image, vital signs and said intraoperative data from said at least one first external device in a window overlaid on a current image displayed via said HMD;
an intraoperative optical coherence tomography (OCT) mode for controlling an intraoperative OCT device;
a teaching mode for enabling said surgeon to guide a second surgeon during said surgical procedure;
a drawing mode for enabling said surgeon to draw symbols on at least one of said at least part of said image and a snapshot of said at least part of said image;
an external mode for controlling at least one second external device;
a procedure-specific mode for displaying at least one of data and overlays specific to said surgical procedure; and
a stage-specific mode for displaying at least one of data and overlays specific to a stage of said surgical procedure.

3. The head mounted display system according to claim 2, wherein each of said at least one first external device and said at least one second external device is selected from the group consisting of:
a surgical microscope;
a phacoemulsification device;
a phacovitrectomy device;
an endoscope; and
a fiber illumination source.

4. The head mounted display system according to claim 2, wherein each of said intraoperative data and said pre-operative data comprises at least one of:
an OCT image;
an MRI image;
a CT image;
an external video feed;
a patient data;
vital signs;
data from a phacoemulsification system; and
data from a phacovitrectomy system.

5. The head mounted display system according to claim 2, wherein at least one of said pre-operative data and said intraoperative data is viewable either on a full screen of said HMD, on a virtual screen or as a picture-in-picture (PIP).

6. The head mounted display system according to claim 1, wherein said tracker is configured to track said head gesture inputs by tracking said HMD.

7. The head mounted display system according to claim 1, further comprising at least one input device, coupled with said computer, configured to receive at least one enablement input from said surgeon,
wherein said at least one enablement input is for enabling said received head gesture input to switch said system mode of said head mounted display system.

8. The head mounted display system according to claim 7, wherein said at least one input device is selected from the list consisting of:
a footswitch;
an eye tracker;
a pedal;
a touch-pad;
a touchscreen;
a joystick;
a button; and
a microphone,
and wherein said at least one enablement input is selected from the list consisting of:
a foot motion input;
an eye movement;
a hand gesture input;
a touchscreen input;
an acoustic command; and
a voice command.

9. The head mounted display system according to claim 1, said head mounted display system also comprising said camera system, and
said head mounted display system further comprising: an illumination system, configured to operate with said camera system; and
a positioning mechanism, coupled with said camera system,
said positioning mechanism comprising at least one of: a camera head positioner and a robotic arm.

10. The head mounted display system according to claim 9, wherein at least one of said first system mode and said second system mode enables an action selected from the group consisting of:
controlling properties of said at least part of said image displayed on said HMD;
controlling said camera system;
controlling said illumination system; and
controlling said positioning mechanism.

11. The head mounted display system according to claim 1, wherein said at least part of said image is either a live video acquired by a single camera or a live stereoscopic video acquired by two cameras.

12. A method for interacting with a head mounted display system for use in a surgical application, said surgical application employing a camera system for providing an image of a surgical field, said head mounted display system allowing for a user to switch between different system modes using at least one head gesture, the method comprising:
displaying, to a surgeon wearing a head mounted display (HMD), at least part of said image of said surgical field from said camera system via said HMD;
receiving a head gesture input by said surgeon from a head tracker configured to track head gesture inputs by said surgeon; and
applying said received head gesture input to switch a system mode of said head mounted display system from a first system mode to a second system mode,
wherein at least one of said first system mode and said second system mode comprises displaying said at least part of said image of said surgical field from said camera system to said surgeon via said HMD,
wherein said at least part of said image is a magnified image of said surgical field.

13. The method according to claim 12, wherein said first system mode and said second system mode is selected from the group consisting of:
a normal mode for displaying said at least part of said image from said camera system via said HMD;
an inverted mode for enabling said surgeon to view said surgical field in an inverted view;
a first external video mode for displaying an image of said surgical field from a first external camera, said first external camera being external to said head mounted display system and also to said camera system;
a second external video mode for displaying an image from a second external camera, said second external camera being external to an operating room wherein a surgical application is being executed;
a visor guided surgery (VGS) mode for enabling said surgeon to see an augmented real world view of said surgical field;
a pre-operative mode for enabling said surgeon to view pre-operative data related to a surgical procedure of said surgical application;
an intraoperative mode for enabling said surgeon to view intraoperative data related to said surgical procedure from at least one first external device;
a picture-in-picture (PIP) mode for enabling said surgeon to view at least one of said at least part of said image, said pre-operative data, said image from said first external camera, said image from said second external camera, a previously acquired snapshot of said at least part of said image, vital signs and said intraoperative data from said at least one first external device in a window overlaid on a current image displayed via said HMD;
an intraoperative optical coherence tomography (OCT) mode for controlling an intraoperative OCT device;
a teaching mode for enabling said surgeon to guide a second surgeon during said surgical procedure;
a drawing mode for enabling said surgeon to draw symbols on at least one of said at least part of said image and a snapshot of said at least part of said image;
an external mode for controlling at least one second external device;
a procedure-specific mode for displaying at least one of data and overlays specific to said surgical procedure; and
a stage-specific mode for displaying at least one of data and overlays specific to a stage of said surgical procedure.

14. The method according to claim 13, wherein at least one of said pre-operative data and said intraoperative data is viewable either on a full screen of said HMD, on a virtual screen or as a picture-in-picture (PIP).

15. The method according to claim 13, wherein each of said intraoperative data and said pre-operative data comprises at least one of:
an OCT image;
an MRI image;
a CT image;
an external video feed;
a patient data;
vital signs;

data from a phacoemulsification system; and data from a phacovitrectomy system.

16. The method according to claim 12, further comprising the procedure of tracking said head gesture inputs of said surgeon by tracking said HMD.

17. The method according to claim 12, wherein said surgical application employs at least one input device configured to receive at least one enablement input from said surgeon, said method further comprising the procedure of receiving said at least one enablement input, wherein said at least one enablement input is for enabling said received head gesture input to switch said system mode of said head mounted display system.

18. The method according to claim 17, wherein said at least one enablement input is selected from the list consisting of:

a foot motion input;

an eye movement;

a hand gesture input;

a touchscreen input;

an acoustic command; and a voice command.

19. The method according to claim 12, wherein at least one of said first system mode and said second system mode enables an action selected from the group consisting of:

controlling properties of said at least part of said image displayed on said HMD;

controlling said camera system, said camera system being configured with said HMD;

controlling an illumination system configured with said HMD; and controlling a positioning mechanism for controlling a position of said camera system.

20. The method according to claim 12, wherein said at least part of said image is either a live video acquired by a single camera or a live stereoscopic video acquired by two cameras.

* * * * *